(12) United States Patent
Chen et al.

(10) Patent No.: US 12,030,941 B2
(45) Date of Patent: Jul. 9, 2024

(54) ANTI-PD-1 ANTIBODIES

(71) Applicant: Wuxi Biologics Ireland Limited, Dublin (IE)

(72) Inventors: Yunying Chen, Shanghai (CN); Jing Li, Shanghai (CN)

(73) Assignee: WUXI BIOLOGICS IRELAND LIMITED, Dundalk (IE)

( * ) Notice: Subject to any disclaimer, the term of this patent is extended or adjusted under 35 U.S.C. 154(b) by 252 days.

(21) Appl. No.: 16/981,336

(22) PCT Filed: Mar. 18, 2019

(86) PCT No.: PCT/CN2019/078515
§ 371 (c)(1),
(2) Date: Sep. 16, 2020

(87) PCT Pub. No.: WO2019/179396
PCT Pub. Date: Sep. 26, 2019

(65) Prior Publication Data
US 2021/0061912 A1 Mar. 4, 2021

(30) Foreign Application Priority Data

Mar. 20, 2018 (CN) ............................ 201810255570
Mar. 20, 2018 (WO) ................ PCT/CN2018/079631

(51) Int. Cl.
*C07K 16/28* (2006.01)
(52) U.S. Cl.
CPC ...... *C07K 16/2818* (2013.01); *C07K 2317/24* (2013.01); *C07K 2317/33* (2013.01); *C07K 2317/569* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 10,323,090 B2 * | 6/2019 | Bowman | A61K 45/06 |
| 10,493,148 B2 * | 12/2019 | Yachi | A61P 29/00 |

FOREIGN PATENT DOCUMENTS

| CN | 105061597 A | 11/2015 |
| CN | 106432494 A | 2/2017 |
| WO | WO-2017/087589 A2 | 5/2017 |
| WO | WO-2017/087589 A3 | 5/2017 |

OTHER PUBLICATIONS

Soler et al., Biomolecules 2021, 11, 163. https://doi.org/10.3390/biom11020163.*
Marabelle et al., "Intratumoral immunotherapy: using the tumor as the remedy", Annals of Oncology, 2017, 28 (Supplement 12): xii33-xii43.

* cited by examiner

*Primary Examiner* — Marianne P Allen
(74) *Attorney, Agent, or Firm* — James S. Keddie; Bozicevic, Field & Francis LLP

(57) ABSTRACT

The present invention provides novel anti-PD-1 antibodies that specifically bind to cell surface PD-1. Also provided are the nucleic acid molecules encoding the anti-PD-1 antibodies, expression vectors and host cells used for the expression of the anti-PD-1 antibodies. The invention further provides the methods for producing the anti-PD-1 antibodies and the use thereof.

12 Claims, 16 Drawing Sheets
Specification includes a Sequence Listing.

A.

B.

A.

B.

A.

B.

A.

B.

A.

B.

A.

B.

A.

B.

A.

B.

A.

B.

C.

D.

A. *Human IFN-γ Production (Auto-MLR)*

B. *Human T-cell Proliferation (Auto-MLR)*

A. *Human IFN-γ Production (Treg-MLR)*

B. *Human T-cell Proliferation (Treg-MLR)*

SEQUENCE LISTING

```
<160> NUMBER OF SEQ ID NOS: 65

<210> SEQ ID NO 1
<211> LENGTH: 10
<212> TYPE: PRT
<213> ORGANISM: Artificial Sequence
<220> FEATURE:
<223> OTHER INFORMATION: CDR1 of AP17R1-2H2 or AP17R1-2H2-Z1

<400> SEQUENCE: 1

Asp Ser Ile Asp Ser Leu Val Asn Met Gly
1               5                   10

<210> SEQ ID NO 2
<211> LENGTH: 15
<212> TYPE: PRT
<213> ORGANISM: artificial sequence
<220> FEATURE:
<223> OTHER INFORMATION: CDR2 of AP17R1-2H2 or AP17R1-2H2-Z1

<400> SEQUENCE: 2

Leu Ile Ala Asn Tyr Ile Thr His Tyr Ala Asp Phe Val Lys Gly
1               5                   10                  15

<210> SEQ ID NO 3
<211> LENGTH: 7
<212> TYPE: PRT
<213> ORGANISM: artificial sequence
<220> FEATURE:
<223> OTHER INFORMATION: CDR3 of AP17R1-2H2 or AP17R1-2H2-Z1

<400> SEQUENCE: 3

Arg Asn Ile Ile Val Asp Tyr
1               5

<210> SEQ ID NO 4
<211> LENGTH: 10
<212> TYPE: PRT
<213> ORGANISM: artificial sequence
<220> FEATURE:
<223> OTHER INFORMATION: CDR1 of AP17R1-2H2-Z1-R1-4B2

<400> SEQUENCE: 4
```

Asp Ser Ile Ser Ser Leu Val Asn Met Gly
1               5                   10

<210> SEQ ID NO 5
<211> LENGTH: 15
<212> TYPE: PRT
<213> ORGANISM: artificial sequence
<220> FEATURE:
<223> OTHER INFORMATION: CDR2 of AP17R1-2H2-Z1-R1-4B2

<400> SEQUENCE: 5

Leu Ile Ala Asn Tyr Ile Thr His Tyr Ala Asp Phe Val Lys Gly
1               5                   10                  15

<210> SEQ ID NO 6
<211> LENGTH: 7
<212> TYPE: PRT
<213> ORGANISM: artificial sequence
<220> FEATURE:
<223> OTHER INFORMATION: CDR3 of AP17R1-2H2-Z1-R1-4B2

<400> SEQUENCE: 6

Arg Asn Ile Ile Val Asp Tyr
1               5

<210> SEQ ID NO 7
<211> LENGTH: 10
<212> TYPE: PRT
<213> ORGANISM: artificial sequence
<220> FEATURE:
<223> OTHER INFORMATION: CDR1 of AP17R1-2H2-Z1-R1-4D8

<400> SEQUENCE: 7

Asp Ser Ile Gln Ser Leu Val Asn Met Gly
1               5                   10

<210> SEQ ID NO 8
<211> LENGTH: 15
<212> TYPE: PRT
<213> ORGANISM: artificial sequence
<220> FEATURE:
<223> OTHER INFORMATION: CDR2 of AP17R1-2H2-Z1-R1-4D8

<400> SEQUENCE: 8

Leu Ile Ala Asn Tyr Ile Thr His Tyr Ala Asp Phe Val Lys Gly
1               5                   10                  15

<210> SEQ ID NO 9
<211> LENGTH: 7
<212> TYPE: PRT
<213> ORGANISM: artificial sequence
<220> FEATURE:
<223> OTHER INFORMATION: CDR3 of AP17R1-2H2-Z1-R1-4D8

<400> SEQUENCE: 9

Arg Asn Ile Ile Val Asp Tyr
1               5

<210> SEQ ID NO 10
<211> LENGTH: 10
<212> TYPE: PRT
<213> ORGANISM: artificial sequence
<220> FEATURE:
<223> OTHER INFORMATION: CDR1 of AP17R1-2H2-Z1-R1-6E1

<400> SEQUENCE: 10

Asp Ser Ile Asp Ser Met Val Asn Met Gly

-continued

```
1               5                   10

<210> SEQ ID NO 11
<211> LENGTH: 15
<212> TYPE: PRT
<213> ORGANISM: artificial sequence
<220> FEATURE:
<223> OTHER INFORMATION: CDR2 of AP17R1-2H2-Z1-R1-6E1

<400> SEQUENCE: 11

Leu Ile Ala Asn Tyr Ile Thr His Tyr Ala Asp Phe Val Lys Gly
1               5                   10                  15

<210> SEQ ID NO 12
<211> LENGTH: 7
<212> TYPE: PRT
<213> ORGANISM: CDR3 of AP17R1-2H2-Z1-R1-6E1
<220> FEATURE:
<223> OTHER INFORMATION: IEC180034PCT

<400> SEQUENCE: 12

Arg Asn Ile Ile Val Asp Tyr
1               5

<210> SEQ ID NO 13
<211> LENGTH: 10
<212> TYPE: PRT
<213> ORGANISM: artificial sequence
<220> FEATURE:
<223> OTHER INFORMATION: CDR1 of AP17R1-2H2-Z1-R1-14A1

<400> SEQUENCE: 13

Asp Ser Ile Asp Ser Leu Val Asn Met Gly
1               5                   10

<210> SEQ ID NO 14
<211> LENGTH: 15
<212> TYPE: PRT
<213> ORGANISM: artificial sequence
<220> FEATURE:
<223> OTHER INFORMATION: CDR2 of AP17R1-2H2-Z1-R1-14A1

<400> SEQUENCE: 14

Leu Ile Ala Thr Tyr Ile Thr His Tyr Ala Asp Phe Val Lys Gly
1               5                   10                  15

<210> SEQ ID NO 15
<211> LENGTH: 7
<212> TYPE: PRT
<213> ORGANISM: artificial sequence
<220> FEATURE:
<223> OTHER INFORMATION: CDR3 of AP17R1-2H2-Z1-R1-14A1

<400> SEQUENCE: 15

Arg Asn Ile Ile Val Asp Tyr
1               5

<210> SEQ ID NO 16
<211> LENGTH: 10
<212> TYPE: PRT
<213> ORGANISM: artificial sequence
<220> FEATURE:
<223> OTHER INFORMATION: CDR1 of AP17R1-2H2-Z1-R1-14F1

<400> SEQUENCE: 16

Asp Ser Ile Asp Ser Leu Val Asn Met Gly
1               5                   10
```

```
<210> SEQ ID NO 17
<211> LENGTH: 15
<212> TYPE: PRT
<213> ORGANISM: artificial sequence
<220> FEATURE:
<223> OTHER INFORMATION: CDR2 of AP17R1-2H2-Z1-R1-14F1

<400> SEQUENCE: 17

Leu Ile Ala Tyr Tyr Ile Thr His Tyr Ala Asp Phe Val Lys Gly
1               5                   10                  15

<210> SEQ ID NO 18
<211> LENGTH: 7
<212> TYPE: PRT
<213> ORGANISM: artificial sequence
<220> FEATURE:
<223> OTHER INFORMATION: CDR3 of AP17R1-2H2-Z1-R1-14F1

<400> SEQUENCE: 18

Arg Asn Ile Ile Val Asp Tyr
1               5

<210> SEQ ID NO 19
<211> LENGTH: 10
<212> TYPE: PRT
<213> ORGANISM: artificial sequence
<220> FEATURE:
<223> OTHER INFORMATION: CDR1 of AP17R1-2H2-Z1-R1-14B3

<400> SEQUENCE: 19

Asp Ser Ile Asp Ser Leu Val Asn Met Gly
1               5                   10

<210> SEQ ID NO 20
<211> LENGTH: 15
<212> TYPE: PRT
<213> ORGANISM: artificial sequence
<220> FEATURE:
<223> OTHER INFORMATION: CDR2 of AP17R1-2H2-Z1-R1-14B3

<400> SEQUENCE: 20

Leu Ile Ala Arg Tyr Ile Thr His Tyr Ala Asp Phe Val Lys Gly
1               5                   10                  15

<210> SEQ ID NO 21
<211> LENGTH: 7
<212> TYPE: PRT
<213> ORGANISM: artificial sequence
<220> FEATURE:
<223> OTHER INFORMATION: CDR3 of AP17R1-2H2-Z1-R1-14B3

<400> SEQUENCE: 21

Arg Asn Ile Ile Val Asp Tyr
1               5

<210> SEQ ID NO 22
<211> LENGTH: 10
<212> TYPE: PRT
<213> ORGANISM: artificial sequence
<220> FEATURE:
<223> OTHER INFORMATION: CDR1 of AP17R1-2H2-Z1-R1-14F3

<400> SEQUENCE: 22

Asp Ser Ile Asp Ser Leu Val Asn Met Gly
1               5                   10
```

```
<210> SEQ ID NO 23
<211> LENGTH: 15
<212> TYPE: PRT
<213> ORGANISM: artificial sequence
<220> FEATURE:
<223> OTHER INFORMATION: CDR2 of AP17R1-2H2-Z1-R1-14F3

<400> SEQUENCE: 23

Leu Ile Ala Trp Tyr Ile Thr His Tyr Ala Asp Phe Val Lys Gly
1               5                   10                  15

<210> SEQ ID NO 24
<211> LENGTH: 7
<212> TYPE: PRT
<213> ORGANISM: artificial sequence
<220> FEATURE:
<223> OTHER INFORMATION: CDR3 of AP17R1-2H2-Z1-R1-14F3

<400> SEQUENCE: 24

Arg Asn Ile Ile Val Asp Tyr
1               5

<210> SEQ ID NO 25
<211> LENGTH: 10
<212> TYPE: PRT
<213> ORGANISM: artificial sequence
<220> FEATURE:
<223> OTHER INFORMATION: CDR1 of AP17R1-2H2-Z1-R1-27A2

<400> SEQUENCE: 25

Asp Ser Ile Asp Ser Leu Val Asn Met Gly
1               5                   10

<210> SEQ ID NO 26
<211> LENGTH: 15
<212> TYPE: PRT
<213> ORGANISM: artificial sequence
<220> FEATURE:
<223> OTHER INFORMATION: CDR2 of AP17R1-2H2-Z1-R1-27A2

<400> SEQUENCE: 26

Leu Ile Ala Asn Tyr Ile Thr His Tyr Ala Asp Phe Val Lys Gly
1               5                   10                  15

<210> SEQ ID NO 27
<211> LENGTH: 7
<212> TYPE: PRT
<213> ORGANISM: artificial sequence
<220> FEATURE:
<223> OTHER INFORMATION: CDR3 of AP17R1-2H2-Z1-R1-27A2

<400> SEQUENCE: 27

Arg Ser Ile Ile Val Asp Tyr
1               5

<210> SEQ ID NO 28
<211> LENGTH: 10
<212> TYPE: PRT
<213> ORGANISM: artificial sequence
<220> FEATURE:
<223> OTHER INFORMATION: CDR1 of AP17R1-2H2-Z1-R1-29B2

<400> SEQUENCE: 28

Asp Ser Ile Asp Ser Leu Val Asn Met Gly
1               5                   10
```

```
<210> SEQ ID NO 29
<211> LENGTH: 15
<212> TYPE: PRT
<213> ORGANISM: artificial sequence
<220> FEATURE:
<223> OTHER INFORMATION: CDR2 of AP17R1-2H2-Z1-R1-29B2

<400> SEQUENCE: 29

Leu Ile Ala Asn Tyr Ile Thr His Tyr Ala Asp Phe Val Lys Gly
1               5                   10                  15

<210> SEQ ID NO 30
<211> LENGTH: 7
<212> TYPE: PRT
<213> ORGANISM: artificial sequence
<220> FEATURE:
<223> OTHER INFORMATION: CDR3 of AP17R1-2H2-Z1-R1-29B2

<400> SEQUENCE: 30

Arg Asn Ile Arg Val Asp Tyr
1               5

<210> SEQ ID NO 31
<211> LENGTH: 10
<212> TYPE: PRT
<213> ORGANISM: artificial sequence
<220> FEATURE:
<223> OTHER INFORMATION: CDR1 of AP17R1-2H2-Z1-R1-29B6

<400> SEQUENCE: 31

Asp Ser Ile Asp Ser Leu Val Asn Met Gly
1               5                   10

<210> SEQ ID NO 32
<211> LENGTH: 15
<212> TYPE: PRT
<213> ORGANISM: artificial sequence
<220> FEATURE:
<223> OTHER INFORMATION: CDR2 of AP17R1-2H2-Z1-R1-29B6

<400> SEQUENCE: 32

Leu Ile Ala Asn Tyr Ile Thr His Tyr Ala Asp Phe Val Lys Gly
1               5                   10                  15

<210> SEQ ID NO 33
<211> LENGTH: 7
<212> TYPE: PRT
<213> ORGANISM: artificial sequence
<220> FEATURE:
<223> OTHER INFORMATION: CDR3 of AP17R1-2H2-Z1-R1-29B6

<400> SEQUENCE: 33

Arg Asn Ile Tyr Val Asp Tyr
1               5

<210> SEQ ID NO 34
<211> LENGTH: 10
<212> TYPE: PRT
<213> ORGANISM: artificial sequence
<220> FEATURE:
<223> OTHER INFORMATION: CDR1 of AP17R1-2H2-Z1-R1-30D3

<400> SEQUENCE: 34

Asp Ser Ile Asp Ser Leu Val Asn Met Gly
1               5                   10

<210> SEQ ID NO 35
```

```
<211> LENGTH: 15
<212> TYPE: PRT
<213> ORGANISM: artificial sequence
<220> FEATURE:
<223> OTHER INFORMATION: CDR2 of AP17R1-2H2-Z1-R1-30D3

<400> SEQUENCE: 35

Leu Ile Ala Asn Tyr Ile Thr His Tyr Ala Asp Phe Val Lys Gly
1               5                   10                  15

<210> SEQ ID NO 36
<211> LENGTH: 7
<212> TYPE: PRT
<213> ORGANISM: artificial sequence
<220> FEATURE:
<223> OTHER INFORMATION: CDR3 of AP17R1-2H2-Z1-R1-30D3

<400> SEQUENCE: 36

Arg Asn Ile Ile Glu Asp Tyr
1               5

<210> SEQ ID NO 37
<211> LENGTH: 114
<212> TYPE: PRT
<213> ORGANISM: artificial sequence
<220> FEATURE:
<223> OTHER INFORMATION: Full-length sequence of AP17R1-2H2

<400> SEQUENCE: 37

Gln Val Gln Leu Val Glu Ser Gly Gly Gly Leu Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60

Arg Phe Thr Ile Ser Arg Asp Ala Ala Lys Asn Thr Val Asn Leu Gln
65                  70                  75                  80

Met Ser Ser Leu Lys Pro Glu Asp Thr Ala Val Tyr Tyr Cys Tyr Ala
                85                  90                  95

Arg Asn Ile Ile Val Asp Tyr Trp Gly Gln Gly Thr Gln Val Thr Val
            100                 105                 110

Ser Ser

<210> SEQ ID NO 38
<211> LENGTH: 114
<212> TYPE: PRT
<213> ORGANISM: artificial sequence
<220> FEATURE:
<223> OTHER INFORMATION: Full-length sequence of AP17R1-2H2-Z1

<400> SEQUENCE: 38

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60
```

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 39
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-4B2

<400> SEQUENCE: 39

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Ser Ser Leu Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 40
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-4D8

<400> SEQUENCE: 40

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Gln Ser Leu Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 41

-continued

```
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-6E1

<400> SEQUENCE: 41

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Met Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 42
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-14A1

<400> SEQUENCE: 42

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
        35                  40                  45

Ala Leu Ile Ala Thr Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 43
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-14F1

<400> SEQUENCE: 43

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30
```

Asn Met Gly Trp Tyr Arg Gln Ala Pro Gly Lys Gln Arg Glu Leu Val
            35                  40                  45

Ala Leu Ile Ala Tyr Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 44
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-14B3

<400> SEQUENCE: 44

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
            35                  40                  45

Ala Leu Ile Ala Arg Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Val Asp Tyr Trp Gly Gln Gly Thr Leu Val Thr Val
            100                 105                 110

Ser Ser

<210> SEQ ID NO 45
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-14F3

<400> SEQUENCE: 45

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
            35                  40                  45

Ala Leu Ile Ala Trp Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

-continued

Arg Asn Ile Ile Val Asp Tyr Trp Gly Gln Gly Thr Leu Val Thr Val
                100                 105                 110
Ser Ser

<210> SEQ ID NO 46
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-27A2

<400> SEQUENCE: 46

Gln Val Gln Leu Val Glu Ser Gly Gly Gly Val Val Gln Pro Gly Gly
1               5                   10                  15
Ser Leu Arg Leu Ser Cys Ala Ala Ser Asp Ser Ile Asp Ser Leu Val
            20                  25                  30
Asn Met Gly Trp Tyr Arg Gln Ala Pro Gly Lys Gln Arg Glu Leu Val
        35                  40                  45
Ala Leu Ile Ala Asn Tyr Ile Thr His Tyr Ala Asp Phe Val Lys Gly
    50                  55                  60
Arg Phe Thr Ile Ser Arg Asp Asn Ser Lys Asn Thr Leu Tyr Leu Gln
65                  70                  75                  80
Met Asn Ser Leu Arg Ala Glu Asp Thr Ala Val Tyr Tyr Cys Tyr Ala
                85                  90                  95
Arg Ser Ile Ile Val Asp Tyr Trp Gly Gln Gly Thr Leu Val Thr Val
                100                 105                 110
Ser Ser

<210> SEQ ID NO 47
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-29B2

<400> SEQUENCE: 47

Gln Val Gln Leu Val Glu Ser Gly Gly Gly Val Val Gln Pro Gly Gly
1               5                   10                  15
Ser Leu Arg Leu Ser Cys Ala Ala Ser Asp Ser Ile Asp Ser Leu Val
            20                  25                  30
Asn Met Gly Trp Tyr Arg Gln Ala Pro Gly Lys Gln Arg Glu Leu Val
        35                  40                  45
Ala Leu Ile Ala Asn Tyr Ile Thr His Tyr Ala Asp Phe Val Lys Gly
    50                  55                  60
Arg Phe Thr Ile Ser Arg Asp Asn Ser Lys Asn Thr Leu Tyr Leu Gln
65                  70                  75                  80
Met Asn Ser Leu Arg Ala Glu Asp Thr Ala Val Tyr Tyr Cys Tyr Ala
                85                  90                  95
Arg Asn Ile Arg Val Asp Tyr Trp Gly Gln Gly Thr Leu Val Thr Val
                100                 105                 110
Ser Ser

<210> SEQ ID NO 48
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-29B6

<400> SEQUENCE: 48

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Tyr Val Asp Tyr Trp Gly Gln Gly Thr Leu Val Thr Val
            100                 105                 110

Ser Ser

<210> SEQ ID NO 49
<211> LENGTH: 114
<212> TYPE: PRT
<213> ORGANISM: artificial sequence
<220> FEATURE:
<223> OTHER INFORMATION: Full-length sequence of AP17R1-2H2-Z1-R1-30D3

<400> SEQUENCE: 49

Gln Val Gln Leu Val Glu Ser Gly Gly Gly Val Val Gln Pro Gly Gly
1               5                   10                  15

Ser Leu Arg Leu Ser Cys Ala Ala Ser Asp Ser Ile Asp Ser Leu Val
            20                  25                  30

Asn Met Gly Trp Tyr Arg Gln Ala Pro Gly Lys Gln Arg Glu Leu Val
        35                  40                  45

Ala Leu Ile Ala Asn Tyr Ile Thr His Tyr Ala Asp Phe Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Tyr Ala
                85                  90                  95

Arg Asn Ile Ile Glu Asp Tyr Trp Gly Gln Gly Thr Leu Val Thr Val
            100                 105                 110

Ser Ser

<210> SEQ ID NO 50
<211> LENGTH: 342
<212> TYPE: DNA
<213> ORGANISM: artificial sequence
<220> FEATURE:
<223> OTHER INFORMATION: Nucleotide sequence encoding AP17R1-2H2

<400> SEQUENCE: 50
caggtgcagc tcgtggagtc tgggggaggc ttggtgcagc ctggggggtc tctgagactc      60
tcctgtgcag cctctgatag catcgacagt ttggttaata tggggtggta ccgccaggct     120
ccagggaagc agcgcgagtt ggtcgcactt attgctaatt atatcacgca ctatgcggac     180
ttcgtgaagg gccgattcac catctccaga gacgccgcca agaacacggt aaatctgcaa     240
atgagcagcc tgaagccaga ggacacggcc gtctattact gttatgccag gaatattatt     300
gtagactact ggggccaggg gacccaggtc accgtctcct ca                        342

<210> SEQ ID NO 51
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1

<400> SEQUENCE: 51

```
caagttcagc tggtggaaag cggtggtggt gtggtgcagc cgggtggttc tttacgtctg      60
agctgtgccg caagcgacag cattgattct ttagtgaaca tgggctggta tcgccaagct     120
ccgggtaaac agcgcgaact ggtggcttta attgccaact acatcaccca ctacgccgat     180
ttcgtgaaag gtcgcttcac catcagccgc gacaacagca aaaacacttt atatctgcag     240
atgaattctt tacgcgccga agataccgcc gtgtattact gctatgcacg caacatcatc     300
gtggattatt ggggtcaagg tactttagtg accgtgagca gc                        342
```

<210> SEQ ID NO 52
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-4B2

<400> SEQUENCE: 52

```
caagttcagc tggtggaaag cggtggtggt gtggtgcagc cgggtggttc tttacgtctg      60
agctgtgccg caagcgacag catttcgtct ttagtgaaca tgggctggta tcgccaagct     120
ccgggtaaac agcgcgaact ggtggcttta attgccaact acatcaccca ctacgccgat     180
ttcgtgaaag gtcgcttcac catcagccgc gacaacagca aaaacacttt atatctgcag     240
atgaattctt tacgcgccga agataccgcc gtgtattact gctatgcacg caacatcatc     300
gtggattatt ggggtcaagg tactttagtg accgtgagca gc                        342
```

<210> SEQ ID NO 53
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-4D8

<400> SEQUENCE: 53

```
caagttcagc tggtggaaag cggtggtggt gtggtgcagc cgggtggttc tttacgtctg      60
agctgtgccg caagcgacag cattcagtct ttagtgaaca tgggctggta tcgccaagct     120
ccgggtaaac agcgcgaact ggtggcttta attgccaact acatcaccca ctacgccgat     180
ttcgtgaaag gtcgcttcac catcagccgc gacaacagca aaaacacttt atatctgcag     240
atgaattctt tacgcgccga agataccgcc gtgtattact gctatgcacg caacatcatc     300
gtggattatt ggggtcaagg tactttagtg accgtgagca gc                        342
```

<210> SEQ ID NO 54
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-6E1

<400> SEQUENCE: 54

```
caagttcagc tggtggaaag cggtggtggt gtggtgcagc cgggtggttc tttacgtctg    60
agctgtgccg caagcgacag cattgattct atggtgaaca tgggctggta tcgccaagct   120
ccgggtaaac agcgcgaact ggtggcttta attgccaact acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg caacatcatc   300
gtggattatt ggggtcaagg tactttagtg accgtgagca gc                      342
```

<210> SEQ ID NO 55
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      14A1

<400> SEQUENCE: 55

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgccacct acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg caacatcatc   300
gtggattatt ggggtcaagg tactttagtg accgtgagca gc                      342
```

<210> SEQ ID NO 56
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      14F1

<400> SEQUENCE: 56

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgcctact acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg caacatcatc   300
gtggattatt ggggtcaagg tactttagtg accgtgagca gc                      342
```

<210> SEQ ID NO 57
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      14B3

<400> SEQUENCE: 57

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgcccgct acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg caacatcatc   300
```

```
gtggattatt ggggtcaagg tactttagtg accgtgagca gc              342
```

<210> SEQ ID NO 58
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      14F3

<400> SEQUENCE: 58

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgcctggt acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg caacatcatc   300
gtggattatt ggggtcaagg tactttagtg accgtgagca gc                      342
```

<210> SEQ ID NO 59
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      27A2

<400> SEQUENCE: 59

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgccaact acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg ctccatcatc   300
gtggattatt ggggtcaagg tactttagtg accgtgagca gc                      342
```

<210> SEQ ID NO 60
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      29B2

<400> SEQUENCE: 60

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgccaact acatcaccca ctacgccgat   180
ttcgtgaaag gtcgcttcac catcagccgc gacaacagca aaaacacttt atatctgcag   240
atgaattctt tacgcgccga agataccgcc gtgtattact gctatgcacg caacatccgc   300
gtggattatt ggggtcaagg tactttagtg accgtgagca gc                      342
```

<210> SEQ ID NO 61
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-

29B6

<400> SEQUENCE: 61

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgccaact acatcaccca ctacgccgat   180
ttcgtgaaag gtcgcttcac catcagccgc gacaacagca aaacacttt atatctgcag    240
atgaattctt tacgcgccga agataccgcc gtgtattact gctatgcacg caacatctac   300
gtggattatt ggggtcaagg tactttagtg accgtgagca gc                      342
```

<210> SEQ ID NO 62
<211> LENGTH: 342
<212> TYPE: DNA
<213> ORGANISM: artificial sequence
<220> FEATURE:
<223> OTHER INFORMATION: Nucleotide sequence encoding AP17R1-2H2-Z1-R1-
      30D3

<400> SEQUENCE: 62

```
caagttcagc tggtggaaag cggtggtggt gtggtgcagc cgggtggttc tttacgtctg    60
agctgtgccg caagcgacag cattgattct ttagtgaaca tgggctggta tcgccaagct   120
ccgggtaaac agcgcgaact ggtggcttta attgccaact acatcaccca ctacgccgat   180
ttcgtgaaag gtcgcttcac catcagccgc gacaacagca aaacacttt atatctgcag    240
atgaattctt tacgcgccga agataccgcc gtgtattact gctatgcacg caacatcatc   300
gaggattatt ggggtcaagg tactttagtg accgtgagca gc                      342
```

<210> SEQ ID NO 63
<211> LENGTH: 10
<212> TYPE: PRT
<213> ORGANISM: Artificial Sequence
<220> FEATURE:
<223> OTHER INFORMATION: CDR1 for the VHH
<220> FEATURE:
<221> NAME/KEY: misc_feature
<222> LOCATION: (4)..(4)
<223> OTHER INFORMATION: Xaa can be Asp or Gln
<220> FEATURE:
<221> NAME/KEY: misc_feature
<222> LOCATION: (6)..(6)
<223> OTHER INFORMATION: Xaa can be Met or Leu

<400> SEQUENCE: 63

Asp Ser Ile Xaa Ser Xaa Val Asn Met Gly
1               5                   10

<210> SEQ ID NO 64
<211> LENGTH: 15
<212> TYPE: PRT
<213> ORGANISM: Artificial Sequence
<220> FEATURE:
<223> OTHER INFORMATION: CDR2 for the VHH
<220> FEATURE:
<221> NAME/KEY: misc_feature
<222> LOCATION: (4)..(4)
<223> OTHER INFORMATION: Xaa can be Asn, Thr, Tyr, Arg or Trp

<400> SEQUENCE: 64

Leu Ile Ala Xaa Tyr Ile Thr His Tyr Ala Asp Phe Val Lys Gly
1               5                   10                  15

<210> SEQ ID NO 65

```
<211> LENGTH: 7
<212> TYPE: PRT
<213> ORGANISM: Artificial Sequence
<220> FEATURE:
<223> OTHER INFORMATION: CDR3 for the VHH
<220> FEATURE:
<221> NAME/KEY: misc_feature
<222> LOCATION: (2)..(2)
<223> OTHER INFORMATION: Xaa can be Asn or Ser
<220> FEATURE:
<221> NAME/KEY: misc_feature
<222> LOCATION: (4)..(4)
<223> OTHER INFORMATION: Xaa can be Ile, Arg or Tyr
<220> FEATURE:
<221> NAME/KEY: misc_feature
<222> LOCATION: (5)..(5)
<223> OTHER INFORMATION: Xaa can be Val or Glu

<400> SEQUENCE: 65

Arg Xaa Ile Xaa Xaa Asp Tyr
1               5
```

ANTI-PD-1 ANTIBODIES

RELATED APPLICATIONS

This application is a U.S. National Phase application, filed under 35 U.S.C. § 371(c), of International Application No. PCT/CN2019/078515, filed Mar. 18, 2019, which claims priority to, and the benefit of, Chinese Application No. 201810255570.3, filed Mar. 20, 2018, and International Application No. PCT/CN2018/079631, filed Mar. 20, 2018, the entire contents of each of which are herein incorporated by reference.

INCORPORATION OF THE SEQUENCE LISTING

A Sequence Listing is provided herewith as a text file, "IEC196024PCT-sequence listing.txt" created on Dec. 20, 2022, and having a size of 31,579 bytes. The contents of the text file are incorporated by reference herein in their entirety.

FIELD OF THE INVENTION

This application generally relates to antibodies. More specifically, the application relates to single-domain antibodies that specifically bind to PD-1, a method for preparing the same, and the use thereof.

BACKGROUND OF THE INVENTION

Increasing evidences from preclinical and clinical results have shown that targeting immune checkpoints is becoming the most promising approach to treat patients with cancers. The protein Programmed Death 1 (PD-1), an inhibitory member of the immunoglobulin super-family with homology to CD28, is expressed on T cells, activated B cells, and myeloid cells (Agata et al, supra; Okazaki et al (2002) Curr. Opin. Immunol. 14: 391779-82; Bennett et al. (2003) J Immunol 170:711-8) and has a critical role in regulating stimulatory and inhibitory signals in the immune system (Okazaki, Taku et al. 2007 International Immunology 19:813-824). PD-1 was discovered through screening for differential expression in apoptotic cells (Ishida et al (1992) EMBO J 11:3887-95).

The PD-1 is a type I transmembrane protein that is part of the Ig gene superfamily (Agata et al. (1996) bit Immunol 8:765-72) and the structure of PD-1 consists of one immunoglobulin variable-like extracellular domain and a cytoplasmic domain containing an immunoreceptor tyrosine-based inhibitory motif (ITIM) and an immunoreceptor tyrosine-based switch motif (ITSM). Although structurally similar to CTLA-4, PD-1 lacks the MYPPPY motif that is critical for B7-1 and B7-2 binding. PD-1 has two known ligands, PD-L1 (B7-H1, CD274) and PD-L2 (B7-DC, CD273), which are cell surface expressed members of the B7 family (Freeman et al (2000) J Exp Med 192: 1027-34; Latchman et al (2001) Nat Immunol 2:261-8; Carter et al (2002) Eur J Immunol 32:634-43). Both PD-L1 and PD-L2 are B7 homologs that bind to PD-1, but do not bind to other CD28 family members.

PD-1, as one of the immune-checkpoint proteins, is an inhibitory member of the CD28 family expressed on activated B cells, T cells, and myeloid cells (Agata et al, supra; Okazaki et al. (2002) Curr Opin Immunol 14: 391779-82; Bennett et al. (2003) J Immunol 170:711-8), and plays a major role in limiting the activity of T cells that provide a major immune resistance mechanism by which tumor cells escaped immune surveillance. PD-1 induces a state of anergy or unresponsiveness in T cells, resulting in the cells being unable to produce optimal levels of effector cytokines. PD-1 may also induce apoptosis in T cells via its ability to inhibit survival signals. PD-1 deficient animals develop various autoimmune phenotypes, including autoimmune cardiomyopathy and a lupus-like syndrome with arthritis and nephritis (Nishimura et al. (1999) Immunity 11:141-51; Nishimura et al. (2001) Science 291:319-22). Additionally, PD-1 has been found to play a role in autoimmune encephalomyelitis, systemic lupus erythematosus, graft-versus-host disease (GVHD), type I diabetes, and rheumatoid arthritis (Salama et al. (2003) J Exp Med 198:71-78: Prokunina and Alarcon-Riquelme (2004) Hum Mol Genet 13:R143; Nielsen et al. (2004) Lupus 11:510). In a murine B cell tumor line, the ITSM of PD-1 was shown to be essential to block BCR-mediated Ca2+-flux and tyrosine phosphorylation of downstream effector molecules (Okazaki et al. (2001) PNAS 98: 13866-71).

The interaction of PD-1 expressed on activated T cells, and PD-L1 expressed on tumor cells negatively regulates immune response and damps anti-tumor immunity. PD-L1 is abundant in a variety of human cancers (Dong et al (2002) Nat. Med 8:787-9). Expression of PD-L1 on tumors is correlated with reduced survival in esophageal, pancreatic and other types of cancers, highlighting this pathway as a promising target for tumor immunotherapy. Several groups have shown that the PD-1-PD-L1 interaction exacerbates disease, resulting in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54:307-314; Konishi et al. (2004) Clin. Cancer Res. 10:5094-100). Immune suppression can be reversed by inhibiting the local interaction of PD-1 with PD-L1, and the effect is additive when the interaction of PD-1 with PD-L2 is blocked as well.

A single-domain antibody (sdAb) is an antibody consisting of a single monomeric variable antibody domain. Like a whole antibody, it is able to bind selectively to a specific antigen. Single-domain antibodies are much smaller than common antibodies which are composed of two heavy protein chains and two light chains. The first single-domain antibodies were engineered from heavy-chain antibodies found in camelids (Hamers-Casterman C, Atarhouch T, Muyldermans S, Robinson G, Hamers C, Songa E B, Bendahman N, Hamers R (1993) Naturally occurring antibodies devoid of light chains. Nature 363(6428):446-448); these are called VHH fragments. Currently, most research into single-domain antibodies is based on heavy chain variable domains.

Single-domain antibodies have many advantages. For instance, they generally display high solubility and stability and can also be readily produced in yeast, plant, and mammalian cells (Harmsen M M, De Haard H J (2007) Properties, production, and applications of camelid single-domain antibody fragments. Appl Microbiol Biotechnol 77(1):13-22). Further, they have good thermal stability and good tissue penetration. And they are also cost efficient in production. The advantages of single-domain antibodies make them suitable for various biotechnological and therapeutic applications. For instance, they are useful in the treatment of diseases, including but not limited to cancer, infectious, inflammatory and neurodegenerative diseases.

Although antibodies against PD-1 are been developed, there are still spaces for improvement for antibody against PD-1 as a therapeutic agent. Further, it is worth noting that there are few single-domain antibodies against PD-1 currently. Accordingly, there is desire in the art to develop novel anti-PD-1 antibodies, particularly single-domain antibodies against PD-1.

SUMMARY OF THE INVENTION

These and other objectives are provided for by the present invention which, in a broad sense, is directed to novel compounds, methods, compositions and articles of manufacture that provide antibodies with improved efficacy. The benefits provided by the present invention are broadly applicable in the field of antibody therapeutics and diagnostics and may be used in conjunction with antibodies that react with a variety of targets. The present invention provides anti-PD-1 antibodies, preferably single-domain antibodies. It also provides methods of preparing the antibodies, nucleic acid molecules encoding the anti-PD-1 antibodies, expression vectors and host cells used for the expression of anti-PD-1 antibodies. The antibodies of the invention provide methods for treating or preventing conditions associated with PD-1.

In some aspects, the invention is directed to a PD-1 binding molecule.

In some embodiments, the PD-1 binding molecule has one or more of the following properties:
(a) binds human PD-1 with a $K_D$ of $1\times10^{-7}$ M or less;
(b) inhibits binding of PD-L1/2 to PD-1;
(c) induces production of IFN-γ in CD4+T cells;
(d) does not substantially bind to human CD28, CTLA-4, ICOS and BTL;
(e) has no cross-reactivity with human PD-1, but has cross-reactivity with mouse PD-1; and
(f) is stable at least 60° C. as measured by DSF assay.

In some embodiments, the PD-1 binding molecule comprises at least one immunoglobulin single variable domain (for example, VHH), wherein the VHH comprises CDR1, CDR2 and CDR3, and wherein CDR1 comprises an amino acid sequence which is at least 90% identical to SEQ ID NO: 1, CDR2 comprises an amino acid sequence which is at least 90% identical to SEQ ID NO: 2, and CDR3 comprises an amino acid sequence which is at least 80% identical to SEQ ID NO: 3.

In some embodiments, the PD-1 binding molecule comprises at least one immunoglobulin single variable domain (for example, VHH), wherein the VHH comprises CDR1, CDR2 and CDR3, and wherein CDR1 differs in amino acid sequence from SEQ ID NO: 1 by an amino acid addition, deletion or substitution of not more than 2 amino acids; CDR2 differs in amino acid sequence from SEQ ID NO: 2 by an amino acid addition, deletion or substitution of not more than 2 amino acids; and/or CDR3 differs in amino acid sequence from SEQ ID NO: 3 by an amino acid addition, deletion or substitution of not more than 2 amino acids.

In some embodiments, the PD-1 binding molecule comprises at least one immunoglobulin single variable domain (for example, VHH), wherein the VHH comprises CDR1, CDR2 and CDR3, and wherein CDR1, CDR2 and CDR3 are selected from the group comprising:
(a) CDR1 which is represented by $DSIX_1SX_2VNMG$, wherein $X_1$=D or Q, and $X_2$=M or L (SEQ ID NO: 63);
(b) CDR2 which is represented by $LIAX_3YITHYADFVKG$, wherein $X_3$=N, T, Y, R or W (SEQ ID NO: 64);
(c) CDR3 which is represented by $RX_4IX_5X_6DY$, wherein $X_4$=N or S, $X_5$=I, R or Y, and $X_6$=V or E (SEQ ID NO: 65).

In some embodiments, the PD-1 binding molecule comprises at least one immunoglobulin single variable domain (for example, VHH), wherein the VHH comprises CDR1, CDR2 and CDR3, and wherein CDR1, CDR2 and CDR3 are selected from the group comprising:
(a) CDR1 with an amino acid sequence as shown in SEQ ID NO: 1, CDR2 with an amino acid sequence as shown in SEQ ID NO: 2, and CDR3 with an amino acid sequence as shown in SEQ ID NO: 3;
(b) CDR1 with an amino acid sequence as shown in SEQ ID NO: 4, CDR2 with an amino acid sequence as shown in SEQ ID NO: 5, and CDR3 with an amino acid sequence as shown in SEQ ID NO: 6;
(c) CDR1 with an amino acid sequence as shown in SEQ ID NO: 7, CDR2 with an amino acid sequence as shown in SEQ ID NO: 8, and CDR3 with an amino acid sequence as shown in SEQ ID NO: 9;
(d) CDR1 with an amino acid sequence as shown in SEQ ID NO: 10, CDR2 with an amino acid sequence as shown in SEQ ID NO: 11, and CDR3 with an amino acid sequence as shown in SEQ ID NO: 12;
(e) CDR1 with an amino acid sequence as shown in SEQ ID NO: 13, CDR2 with an amino acid sequence as shown in SEQ ID NO: 14, and CDR3 with an amino acid sequence as shown in SEQ ID NO: 15;
(f) CDR1 with an amino acid sequence as shown in SEQ ID NO: 16, CDR2 with an amino acid sequence as shown in SEQ ID NO: 17, and CDR3 with an amino acid sequence as shown in SEQ ID NO: 18;
(g) CDR1 with an amino acid sequence as shown in SEQ ID NO: 19, CDR2 with an amino acid sequence as shown in SEQ ID NO: 20, and CDR3 with an amino acid sequence as shown in SEQ ID NO: 21;
(h) CDR1 with an amino acid sequence as shown in SEQ ID NO: 22, CDR2 with an amino acid sequence as shown in SEQ ID NO: 23, and CDR3 with an amino acid sequence as shown in SEQ ID NO: 24;
(i) CDR1 with an amino acid sequence as shown in SEQ ID NO: 25, CDR2 with an amino acid sequence as shown in SEQ ID NO: 26, and CDR3 with an amino acid sequence as shown in SEQ ID NO: 27;
(j) CDR1 with an amino acid sequence as shown in SEQ ID NO: 28, CDR2 with an amino acid sequence as shown in SEQ ID NO: 29, and CDR3 with an amino acid sequence as shown in SEQ ID NO: 30;
(k) CDR1 with an amino acid sequence as shown in SEQ ID NO: 31, CDR2 with an amino acid sequence as shown in SEQ ID NO: 32, and CDR3 with an amino acid sequence as shown in SEQ ID NO: 33; and
(l) CDR1 with an amino acid sequence as shown in SEQ ID NO: 34, CDR2 with an amino acid sequence as shown in SEQ ID NO: 35, and CDR3 with an amino acid sequence as shown in SEQ ID NO: 36.

In some embodiments, the PD-1 binding molecule comprises at least one immunoglobulin single variable domain (for example, VHH), wherein the VHH comprises
(A) the amino acid sequence shown in any of SEQ ID NOs: 37-49;
(B) an amino acid sequence which is at least 85%, at least 90%, or at least 95% identical to any of SEQ ID NOs: 37-49; or
(C) an amino acid sequence with addition, deletion and/or substitution of one or more (for example, 1, 2, 3, 4, 5, 6, 7, 8, 9 or 10) amino acids compared with any of SEQ ID NOs: 37-49.

In some aspects, the invention is directed to an isolated nucleic acid molecule, comprising a nucleic acid sequence encoding PD-1 binding molecule as disclosed herein.

In some aspects, the invention is directed to an expression vector comprising the nucleic acid molecule encoding the PD-1 binding molecule as disclosed herein.

In some aspects, the invention is directed to a host cell comprising the expression vector as disclosed herein.

In some aspects, the invention is directed to a pharmaceutical composition comprising at least one PD-1 binding molecule as disclosed herein and a pharmaceutically acceptable carrier.

In some aspects, the invention is directed to a method for preparing the PD-1 binding molecule which comprises expressing the PD-1 binding molecule in the host cell and isolating the PD-1 binding molecule from the host cell.

In some aspects, the invention is directed to a method for inhibiting or blocking the binding of PD-L1 to PD-1 in a subject, comprising: administering a therapeutically effective amount of the PD-1 binding molecule as disclosed herein to the subject.

In some aspects, the invention is directed to a method for inhibiting or blocking the binding of PD-L2 to PD-1 in a subject, comprising: administering a therapeutically effective amount of the PD-1 binding molecule as disclosed herein to the subject.

In some aspects, the invention is directed to a method of treating a condition associated with PD-1 in a subject, comprising: administering a therapeutically effective amount of the PD-1 binding molecule as disclosed herein to the subject.

In some aspects, the invention is directed to a method of treating a condition in a subject that would benefit from upregulation of immune response, comprising administering a therapeutically effective amount of the PD-1 binding molecule as disclosed herein to the subject.

In some aspects, the invention is directed to the use of the PD-1 binding molecule as disclosed herein in the manufacture of a medicament for treating or preventing proliferative disorders such as cancers.

In some aspects, the invention is directed to the use of PD-1 binding molecule as disclosed herein in the manufacture of a medicament for treating or preventing a condition that would benefit from upregulation of immune response.

In some aspects, the invention is directed to kits or devices and associated methods that employ the PD-1 binding molecule as disclosed herein, and pharmaceutical compositions as disclosed herein, which are useful for the treatment of proliferative disorders such as cancer. To this end the present invention preferably provides an article of manufacture useful for treating such disorders comprising a receptacle containing the PD-1 binding molecule as disclosed herein and instructional materials for using the PD-1 binding molecule as disclosed herein to treat, ameliorate or prevent a proliferative disorder or progression or recurrence thereof. In selected embodiments, the devices and associated methods will comprise the step of contacting at least one circulating tumor cell with the PD-1 binding molecule as disclosed herein.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. Further, the contents of all references, patents and published patent applications cited throughout this application are incorporated herein in entirety by reference.

AP17R1-2H2-Z1-R1-14A1-FC(IgG4.SP) (panel B) by DSF (Differential Scanning Fluorimetry) assay.

Figure 15:
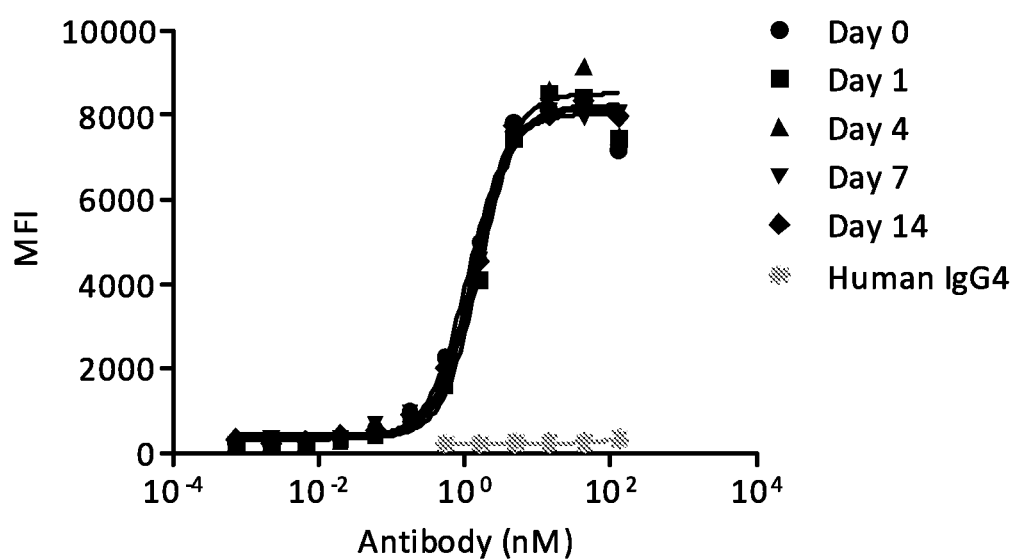

FIG. 15 shows the stability of the W3056-AP17R1-2H2-Z1-R1-14A1-FC(IgG4.SP) in human serum at 37° C. measured by target binding of serum treated samples by FACS

DETAILED DESCRIPTION OF THE INVENTION

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In this application, the use of "or" means "and/or" unless stated otherwise. Furthermore, the use of the term "comprising," as well as other forms, such as "comprises" and "comprised", is not limiting. In addition, ranges provided in the specification and appended claims include both end points and all points between the end points.

Generally, nomenclature used in connection with, and techniques of, cell and tissue culture, molecular biology, immunology, microbiology, genetics and protein and nucleic acid chemistry and hybridization described herein are well known and commonly used in the art. The methods and techniques of the present invention are generally performed according to conventional methods well known in the art and as described in various general and more specific references that are cited and discussed throughout the present specification unless otherwise indicated. See, e.g., Abbas et al., Cellular and Molecular Immunology, $6^{th}$ ed., W.B. Saunders Company (2010); Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). The nomenclature used in connection with, and the laboratory procedures and techniques of, analytical chemistry, synthetic organic chemistry, and medicinal and pharmaceutical chemistry described herein are well known and commonly used in the art. Moreover, any section headings used herein are for organizational purposes only and are not to be construed as limiting the subject matter described.

Definitions

In order to better understand the invention, the definitions and explanations of the relevant terms are provided as follows.

The term "antibody" or "Ab", as used herein, generally refers to any form of antibody that exhibits the desired biological or binding activity. It covers, but is not limited to, humanized antibodies, fully human antibodies, chimeric antibodies and single-domain antibodies. An antibody may comprise heavy chain(s) and light chain(s). Heavy chains may be classified into μ, δ, γ, α and ε, which define isotypes of an antibody as IgM, IgD, IgG, IgA and IgE, respectively. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196:901-917; Chothia et al., (1989) Nature 342:878-883. Antibodies may be of different antibody isotypes, for example, IgG (e.g., IgG1, IgG2, IgG3 or IgG4 subtype), IgA1, IgA2, IgD, IgE or IgM antibody.

The term "humanized antibody", as used herein, refers to antibodies in which CDR sequences derived from the germline of another mammalian species, such as a mouse, have been grafted onto human framework sequences. Additional framework region modifications may be made within the human framework sequences.

The term "chimeric antibody", as used herein, refers to antibodies in which the variable region sequences are derived from one species and the constant region sequences are derived from another species, such as an antibody in which the variable region sequences are derived from a mouse antibody and the constant region sequences are derived from a human antibody.

The term "PD-1", as used herein, refers programmed cell death protein, which belongs to the superfamily of immunoglobulin and functions as co-inhibitory receptor to negatively regulate the immune system. PD-1 is a member of the CD28/CTLA-4 family, and has two known ligands including PD-L1 and PD-L2. Alternative names or synonyms for PD-1 include PDCD1, PD1, CD279 and SLEB2, et al. Representative amino acid sequence of human PD-1 is disclosed under the NCBI accession number: NP_005009.2, and the representative nucleic acid sequence encoding the human PD-1 is shown under the NCBI accession number: NM_005018.2.

The term "PD-L1", as used herein, refers to programmed cell death ligand 1 (PD-L1, see, for example, Freeman et al. (2000) J. Exp. Med. 192: 1027). Alternative names or synonyms for PD-L1 include PDCD1L1, PDL1, B7H1, CD274 and B7-H, et al. Representative amino acid sequence of human PD-L1 is disclosed under the NCBI accession number: NP_054862.1, and the representative nucleic acid sequence encoding the human PD-L1 is shown under the NCBI accession number: NM_014143.3. PD-L1 is expressed in placenta, spleen, lymph nodes, thymus, heart, fetal liver, and is also found on many tumor or cancer cells. PD-L1 binds to its receptor PD-1 or B7-1, which is expressed on activated T cells, B cells and myeloid cells. The binding of PD-L1 and its receptor induces signal transduction to suppress TCR-mediated activation of cytokine production and T cell proliferation. Accordingly, PD-L1 plays a major role in suppressing immune system during particular events such as pregnancy, autoimmune diseases, tissue allografts, and is believed to allow tumor or cancer cells to circumvent the immunological checkpoint and evade the immune response.

The term "PD-L2", as used herein, refers to programmed cell death ligand 2. Alternative names or synonyms for PD-L2 include PDCD1L2, PDL2, B7-DC, Btdc and CD273, et al. Representative amino acid sequence of human PD-L2 is disclosed under the NCBI accession number: NP_079515.2.

The term "Anti-PD-1 antibody", as used herein, refers to an antibody that is capable of specific binding to PD-1 (e.g. human, monkey or monkey PD-1). It is advantage that the Anti-PD-1 antibody specifically binds to PD-1 with an affinity which is sufficient to provide for diagnostic and/or therapeutic use.

The term "Ka", as used herein, is intended to refer to the association rate of a particular antibody-antigen interaction, whereas the term "Kd" as used herein, is intended to refer to the dissociation rate of a particular antibody-antigen interaction. Kd values for antibodies can be determined using methods well established in the art. The term "$K_D$" as used herein, is intended to refer to the dissociation constant of a particular antibody-antigen interaction, which is obtained from the ratio of Kd to Ka (i.e., Kd/Ka) and is expressed as a molar concentration (M). A preferred method for determining the Kd of an antibody is by using surface plasmon resonance, preferably using a biosensor system such as a Biacore® system.

The term "specific binding" or "specifically binds" as used herein refers to a non-random binding reaction between two molecules, such as for example between an antibody and an antigen.

The ability to "inhibit binding", "block binding" or "compete for the same epitope", as used herein, refers to the ability of an antibody to inhibit the binding interaction between two molecules (e.g. human PD-1 and an anti-PD-1 antibody) to any detectable degree. In some embodiments, an antibody that blocks binding between two molecules inhibits the binding interaction between the two molecules by at least 50%. In some embodiments, this inhibition may be greater than 60%, greater than 70%, greater than 80%, or greater than 90%.

The term "high affinity" for an IgG antibody, as used herein, refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen.

The term "$EC_{50}$", as used herein, which is also termed as "half maximal effective concentration" refers to the concentration of a drug, antibody or toxicant which induces a response halfway between the baseline and maximum after a specified exposure time. In the context of the application, $EC_{50}$ is expressed in the unit of "nM".

The term "epitope", as used herein, refers to a portion on antigen that an immunoglobulin or antibody specifically binds to. "Epitope" is also known as "antigenic determinant". Epitope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein. Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. RSV fusion protein). High-throughput methods for obtaining antibodies binding to the same epitope, which are based on their cross-competition, are described in an international patent application WO 03/48731.

The term "isolated", as used herein, refers to a state obtained from natural state by artificial means. If a certain "isolated" substance or component is present in nature, it is possible because its natural environment changes, or the substance is isolated from natural environment, or both. For example, a certain un-isolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other impure substances that do not affect the activity of the isolated substance.

The term "isolated antibody", as used herein, is intended to refer to an antibody that is substantially free of other antibodies having different antigenic specificities (e.g., an isolated antibody that specifically binds a PD-1 protein is substantially free of antibodies that specifically bind antigens other than PD-1 proteins). An isolated antibody that specifically binds a human PD-1 protein may, however, have cross-reactivity to other antigens, such as PD-1 proteins from other species. Moreover, an isolated antibody can be substantially free of other cellular material and/or chemicals.

The term "vector", as used herein, refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprise multiple elements for controlling expression, including, but not limited to, a promoter sequence, a transcription initiation sequence, an enhancer sequence, a selection element and a reporter gene. In addition, a vector may comprise origin of replication.

The term "host cell", as used herein, refers to a cell into which a vector can be introduced, including, but not limited to, prokaryotic cell such as *E. coli* or *Bacillus subtilis*, fungal cell such as yeast cell or *Aspergillus*, insect cell such as S2

Drosophila cell or Sf9, and animal cell such as fibroblast, CHO cell, COS cell, NSO cell, HeLa cell, BHK cell, HEK 293 cell or human cell.

The term "T cell", as used herein, includes CD4+ T cells, CD8+ T cells, T helper 1 type T cells, T helper 2 type T cells, T helper 17 type T cells and inhibitory T cells.

The term "identity", as used herein, refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SIAMJ. Applied Math. 48:1073.

The term "immunogenicity", as used herein, refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

The term "transfection" or "transfect", as used herein, refers to the process by which nucleic acids are introduced into eukaryotic cells, particularly mammalian cells. Protocols and techniques for transfection include but not limited to lipid transfection and chemical and physical methods such as electroporation. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al, 1981, Gene 13:197.

The term "SPR" or "surface plasmon resonance", as used herein, refers to and includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "fluorescence-activated cell sorting" or "FACS", as used herein, refers to a specialized type of flow cytometry. It provides a method for sorting a heterogeneous mixture of biological cells into two or more containers, one cell at a time, based upon the specific light scattering and fluorescent characteristics of each cell (FlowMetric. "Sorting Out Fluorescence Activated Cell Sorting". Retrieved 2017-11-09). Instruments for carrying out FACS are known to those of skill in the art and are commercially available to the public. Examples of such instruments include FACS Star Plus, FACScan and FACSort instruments from Becton Dickinson (Foster City, Calif.) Epics C from Coulter Epics Division (Hialeah, Fla.) and MoFlo from Cytomation (Colorado Springs, Colo.).

The term "subject" includes any human or nonhuman animal, preferably humans.

The term "condition associated with PD-1" or "condition related to PD-1", as used herein, refers to any condition that is caused by, exacerbated by, or otherwise linked to increased or decreased expression or activities of PD-1 (e.g. a human PD-1).

The term "cancer", as used herein, refers to any or a tumor or a malignant cell growth, proliferation or metastasis-mediated, solid tumors and non-solid tumors such as leukemia and initiate a medical condition.

The term "treatment", "treating" or "treated", as used herein in the context of treating a condition, pertains generally to treatment and therapy, whether of a human or an animal, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included. For cancer, "treating" may refer to dampen or slow the tumor or malignant cell growth, proliferation, or metastasis, or some combination thereof. For tumors, "treatment" includes removal of all or part of the tumor, inhibiting or slowing tumor growth and metastasis, preventing or delaying the development of a tumor, or some combination thereof.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen. Specifically, the "therapeutically-effective amount," refers to an antibody or antigen-binding portion thereof in an amount or concentration effective to treat the human PD-1-related diseases or conditions.

The present invention in a "host cell", as used herein, refers to a cell with the introduction of exogenous polynucleotides.

The term "therapeutically effective amount" or "effective amount", as used herein, refers to a drug in an amount or concentration effective to treat the human PD-1-related diseases or conditions.

The term "pharmaceutically acceptable", as used herein, means that the vehicle, diluent, excipient and/or salts thereof, are chemically and/or physically is compatible with other ingredients in the formulation, and the physiologically compatible with the recipient.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

PD-1 Binding Molecules

In some aspects, the invention comprises PD-1 binding molecule.

The PD-1 binding molecule, in a general sense, may include any molecule that specifically binds to PD-1. In some circumstances, "PD-1 binding molecule" may include "PD-1 antagonist". "PD-1 antagonist" refers to any chemical compound or biological molecule that blocks the binding of PD-L1 to PD-1 expressed on an immune cell (T cell, B cell or NKT cell) and preferably also blocks binding of PD-L2 to the immune-cell expressed PD-1. The PD-1 binding molecule or PD-1 antagonist may be a polypeptide or a protein, for example, an antibody, more particularly, an anti-PD-1 antibody.

The antibody includes, but is not limited to, a chimeric antibody, a humanized antibody, or a single-domain antibody. In a specific embodiment, the PD-1 binding molecule is a single-domain antibody, which generally refers to an antibody consisting of a single monomeric variable antibody domain. Like a whole antibody, a single-domain antibody is able to bind selectively to a specific antigen.

More specifically, the PD-1 binding molecule is a single-domain heavy chain antibody, which is interchangeably used with the terms "VHH", "VHH antibody", "VHH domain", "VHH antibody fragment", "$V_{HH}$" or "Nanobody," et al. V molecules derived from Camelidae antibodies are among the smallest intact antigen-binding domains known (approximately 15 kDa, or 10 times smaller than a conventional IgG) and hence are well suited towards delivery to dense tissues and for accessing the limited space between macromolecules.

The single-domain antibody of the invention disclosed herein may be made by the skilled artisan according to methods known in the art or any future method. For example, VHHs may be obtained using methods known in the art such as by immunizing a camel and obtaining hybridoma's therefrom, or by cloning a library of VHHs of the invention using molecular biology techniques known in the art and subsequent selection by using phage display.

For instance, a single-domain antibody can be obtained by immunization of llamas or alpacas with the desired antigen and subsequent isolation of the mRNA coding for heavy-chain antibodies. By reverse transcription and polymerase chain reaction, a gene library of single-domain antibodies containing several million clones is produced. Screening techniques like phage display and ribosome display help to identify the clones binding the antigen. One technique is phage display in which a library of (e.g., human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., Barbas et al., *Proc. Natl. Acad. Sci. USA* 88:7978-7982 (1991)).

When the most potent clones have been identified, their DNA sequence is optimized, for example, by affinity maturation or humanization. Humanization may prevent immunological reactions of the human organism against the antibody.

Accordingly, the single-domain antibodies can be obtained (1) by isolating the VHH domain of a naturally occurring heavy chain antibody; (2) by expression of a nucleotide sequence encoding a naturally occurring VHH domain; (3) by "humanization" (as described below) of a naturally occurring VHH domain or by expression of a nucleic acid encoding a such humanized VHH domain; (4) by "camelization" of a naturally occurring VH domain from any animal species, in particular a species of mammal, such as from a human being, or by expression of a nucleic acid encoding such a camelized VH domain; (5) by "camelisation" of a "domain antibody" or "Dab" as described by Ward et al (supra), or by expression of a nucleic acid encoding such a camelized VH domain; (6) using synthetic or semi-synthetic techniques for preparing proteins, polypeptides or other amino acid sequences; (7) by preparing a nucleic acid encoding a VHH using techniques for nucleic acid synthesis, followed by expression of the nucleic acid thus obtained; and/or (8) by any combination of the foregoing. Suitable methods and techniques for performing the foregoing will be clear to the skilled person based on the disclosure herein and for example include the methods and techniques described in more detail hereinbelow.

Single-domain antibodies are usually generated by PCR cloning of variable domain repertoire from blood, lymph node, or spleen cDNA obtained from immunized animals into a phage display vector. Antigen-specific single-domain antibodies are commonly selected by panning phase libraries on immobilized antigen, e.g., antigen coated onto the plastic surface of a test tube, biotinylated antigens immobilized on Streptavidin beads, or membrane proteins expressed on the surface of cells. The affinity of adAbs can often been improved by mimicking this strategy in vitro, for instance, by site directed mutagenesis of the CDR regions and further rounds of panning on immobilized antigen under conditions of increased stringency (higher temperature, high or low salt concentration, high or low pH, and low antigen concentrations) (Wesolowski et al., Single domain antibodies: promising experimental and therapeutic tools in infection and immunity. Med Microbiol Immunol (2009) 198: 157-174).

Methods for preparing a VHH specifically binding to an antigen or epitope was described in references, for example: R. van der Linden et al., Journal of Immunological Methods, 240(2000) 185-195; Li et al., J Biol Chem., 287(2012) 13713-13721; Deffar et al., African Journal of Biotechnology Vol. 8(12), pp. 2645, 17 Jun. 2009 and WO94/04678.

In some embodiments, the VHH in the PD-1 binding molecule is fused to an Fc-domain of an antibody, for example, Fc-domain of IgG (e.g., IgG4 or IgG1). In a specific embodiment, the Fc-domain is an Fc-domain of IgG4. By fusing VHH to a Fc domain, it may be more efficient to recruit effector functions, such as ADCC and CDC. Also, the fusion of VHH to Fc domain may help the PD-1 binding molecule to form a dimer, and may also help the extension of the half life of PD-1 binding molecule in vivo.

The term "antibody-dependent cell-mediated cytotoxicity" or "ADCC", as used herein, refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. PNAS (USA) 95:652-656 (1998).

The term "complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., J. Immunol. Methods 202: 163 (1996), may be performed.

For convenience of description, the PD-1 binding molecule is described as anti-PD-1 antibody in the following sections.

Anti-PD-1 Antibodies with Certain Properties

The antibodies of the invention are characterized by particular functional features or properties of the antibodies. In some embodiments, the antibodies have one or more of the following properties:
 (a) bind human PD-1 with a $K_D$ of $1\times10^{-7}$ M or less;
 (b) inhibit or blocks binding of PD-L1 or PD-L2 to PD-1;
 (c) induce production of IFN-γ in CD4+T cells;
 (d) do not substantially bind to human CD28, CTLA-4, ICOS and/or BTL;
 (e) have no cross-reactivity with human PD-1, but have cross-reactivity with mouse PD-1; and
 (f) are stable at least 60° C.

The antibody of the invention binds to cell surface PD-1 with high affinity. The binding of an antibody of the invention to PD-1 can be assessed using one or more techniques well established in the art, for instance, ELISA. The binding specificity of an antibody of the invention can also be determined by monitoring binding of the antibody to cells expressing a PD-1 protein, e.g., flow cytometry. For example, an antibody can be tested by a flow cytometry assay in which the antibody is reacted with a cell line that expresses human PD-1, such as CHO cells that have been transfected to express PD-1 on their cell surface. Additionally or alternatively, the binding of the antibody, including the binding kinetics (e.g., Kd value) can be tested in BIAcore binding assays. Still other suitable binding assays include ELISA assays, for example using a recombinant PD-1 protein. For instance, an antibody of the invention binds to a cell surface (e.g., human PD-1) protein with a $K_D$ of $1\times10^{-7}$ M or less, $5\times10^{-8}$ M or less, $2\times10^{-8}$ M or less, $5\times10^{-9}$ M or less, $4\times10^{-9}$ M or less, $3\times10^{-9}$ M or less, $2\times10^{-9}$ M or less, $1\times10^{-9}$ M or less, $5\times10^{10}$ M or less, $1\times10^{-10}$ M or less.

In some embodiments, the antibodies of the invention bind to cynomolgus or monkey PD-1 at an $EC_{50}$ of no more than or about 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, 0.09 nM, 0.08 nM, 0.07 nM, 0.06 nM, 0.05 nM, 0.04 nM, 0.03 nM, 0.02 nM, or 0.01 nM, as measured by FACS.

In some embodiments, the antibodies of the invention inhibit the binding of human PD-1 to its ligand at an $IC_{50}$ of 0.2 nM-100 nM (e.g. 0.2 nM-50 nM, 0.2 nM-30 nM, 0.2 nM-20 nM, 0.2 nM-10 nM, or 1 nM-10 nM), as measured in a competition assay, for example by ELISA.

The anti-PD-1 antibodies of the invention are specific for PD-1. In some embodiments, the antibodies and antigen-binding fragments thereof do not bind to CD28, CTLA-4, ICOS and/or BTL. For example, the binding affinity with CD28, CTLA-4, ICOS and/or BTL is less than 15%, 10%, 9%, 8%, 7%, 6%, 5%, 4%, 3%, 2%, or 1% of the binding affinity with PD-1.

In some embodiments, the antibodies of the invention block binding of human PD-1 to its ligand and thereby providing biological activity including, for example, inducing cytokine production from the activated T cells (such as CD4+ T cells and CD8+ T cells), inducing proliferation of activated T cells (such as CD4+ T cells and CD8+ T cells), and reversing T reg's suppressive function. Exemplary cytokines include IL-2 and IFNγ. The term "IL-2" refers to interleukin 2, a type of cytokine signaling molecule in the immune system that regulates the activities of white blood cells (e.g. leukocytes). The term "Interferon gamma (IFNγ)" is a cytokine that is produced by natural killer (NK), NK T cells, CD4+ and CD8+T cells, which is a critical activator of macrophages and inducer of major histocompatibility complex (MEC) molecule expression. The cytokine production can be determined using methods known in the art, for example, by ELISA. Methods can also be used to detect proliferation of T cells, including [3H] thymidine incorporation assay.

In some embodiments, the antibodies of the invention have no cross-reactivity with human PD-1, but have cross-reactivity with mouse PD-1. Most of monoclonal antibodies against PD-1 currently tested in clinical trials are only against to human PD-1 which limits preclinical in vivo assay and diminished efficacy owing to the immunogenicity of the mouse-derived protein sequences. Humanized antibody with cross-reactivity to mouse PD-1 overcome these shortages and showed more tolerability and higher efficiency in vivo.

Anti-PD-1 Antibodies Comprising CDRs with Sequence Identity to Specific Sequences In some embodiments, the anti-PD-1 antibody of the invention comprises at least one immunoglobulin single variable domain (for example, VHH), wherein the VHH comprises CDR1, CDR2 and CDR3, and wherein CDR1 comprises an amino acid sequence which is at least 90% identical to SEQ ID NO: 1, CDR2 comprises an amino acid sequence which is at least 90% identical to SEQ ID NO: 2, and CDR3 comprises an amino acid sequence which is at least 80% identical to SEQ ID NO: 3.

The assignment of amino acids to each CDR may be in accordance with one of the numbering schemes provided by Kabat et al. (1991) *Sequences of Proteins of Immunological Interest* (5$^{th}$ Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) *Handbook of Therapeutic Antibodies*, 3$^{rd}$ Ed., Wily-VCH Verlag GmbH and Co. unless otherwise noted.

Variable regions and CDRs in an antibody sequence can be identified according to general rules that have been developed in the art (as set out above, such as, for example, the Kabat numbering system) or by aligning the sequences against a database of known variable regions. Methods for identifying these regions are described in Kontermann and Dubel, eds., Antibody Engineering, Springer, New York, NY, 2001 and Dinarello et al., Current Protocols in Immunology, John Wiley and Sons Inc., Hoboken, NJ, 2000. Exemplary databases of antibody sequences are described in, and can be accessed through, the "Abysis" website at www.bioinf.org.uk/abs (maintained by A. C. Martin in the Department of Biochemistry & Molecular Biology University College London, London, England) and the VBASE2 website at www.vbase2.org, as described in Retter et al., Nucl. Acids Res., 33 (Database issue): D671-D674 (2005). Preferably sequences are analyzed using the Abysis database, which integrates sequence data from Kabat, IMGT and the Protein Data Bank (PDB) with structural data from the PDB. See Dr. Andrew C. R. Martin's book chapter *Protein Sequence and Structure Analysis of Antibody Variable Domains*. In: *Antibody Engineering Lab Manual* (Ed.: Duebel, S. and Kontermann, R., Springer-Verlag, Heidelberg, ISBN-13: 978-3540413547, also available on the website bioinforg.uk/abs). The Abysis database website further includes general rules that have been developed for identifying CDRs which can be used in accordance with the teachings herein. Unless otherwise indicated, all CDRs set forth herein are derived according to the Abysis database website as per Kabat.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al, (1997) Nucleic Acids Res. 25(17):3389-3402. When utilizing BLAST and Gapped BLAST programs, the default parameters of the respective programs {e.g., XBLAST and NBLAST) can be used. See www.ncbi.nlm.nih.gov.

In other embodiments, the CDR amino acid sequences can be at least 90%, 91%, 92%, 93%, 94%, 95%, 96%, 97%, 98% or 99% identical to the respective sequences set forth above.

Anti-PD-1 Antibodies Comprising CDRs with Amino Acid Addition, Deletion or Substitution In some embodiments, the anti-PD-1 antibody of the invention comprises at least one immunoglobulin single variable domain (for example, VHH), wherein the VHH comprises CDR1, CDR2 and CDR3, and wherein CDR1 differs in amino acid sequence from SEQ ID NO: 1 by an amino acid addition, deletion or substitution of not more than 2 amino acids; CDR2 differs in amino acid sequence from SEQ ID NO: 2 by an amino acid addition, deletion or substitution of not more than 2 amino acids; and/or CDR3 differs in amino acid sequence from SEQ ID NO: 3 by an amino acid addition, deletion or substitution of not more than 2 amino acids. For examples, the CDR1, CDR2 and CDR3 differs from amino acid sequences set forth in SEQ ID NOs: 1-3 by an amino acid addition, deletion or substitution of only one amino acid, respectively.

In some embodiments, the anti-PD-1 antibody of the invention comprises at least one immunoglobulin single variable domain (for example, VHH), wherein the VHH comprises CDR1, CDR2 and CDR3, and wherein CDR1, CDR2 and CDR3 are selected from the group comprising:
  (a) CDR1 which is represented by $DSIX_1SX_2VNMG$, wherein $X_1$=D or Q, and $X_2$=M or L;
  (b) CDR2 which is represented by $LIAX_3YITHYADFVKG$, wherein $X_3$=N, T, Y, R or W;
  (c) CDR3 which is represented by $RX_4IX_5X_6DY$, wherein $X_4$=N or S, $X_5$=I, R or Y, and $X_6$=V or E.

Preferably, the CDRs of the isolated antibody or the antigen-binding portion thereof contain a conservative substitution of not more than 2 amino acids, or not more than 1 amino acid. The term "conservative substitution", as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Anti-PD-1 Antibodies Comprising CDRs

In some embodiments, at least one immunoglobulin single variable domain (for example, VHH), wherein the VHH comprises CDR1, CDR2 and CDR3, and wherein CDR1, CDR2 and CDR3 are selected from the group comprising:
- (a) CDR1 comprising or consisting of an amino acid sequence as shown in SEQ ID NO: 1, CDR2 comprising or consisting of an amino acid sequence as shown in SEQ ID NO: 2, and CDR3 comprising or consisting of an amino acid sequence as shown in SEQ ID NO: 3;
- (b) CDR1 comprising or consisting of an amino acid sequence as shown in SEQ ID NO: 4, CDR2 comprising or consisting of an amino acid sequence as shown in SEQ ID NO: 5, and CDR3 comprising or consisting of an amino acid sequence as shown in SEQ ID NO: 6;
- (c) CDR1 comprising or consisting of an amino acid sequence as shown in SEQ ID NO: 7, CDR2 comprising or consisting of an amino acid sequence as shown in SEQ ID NO: 8, and CDR3 comprising or consisting of an amino acid sequence as shown in SEQ ID NO: 9;
- (d) CDR1 comprising or consisting of an amino acid sequence as shown in SEQ ID NO: 10, CDR2 comprising or consisting of an amino acid sequence as shown in SEQ ID NO: 11, and CDR3 comprising or consisting of an amino acid sequence as shown in SEQ ID NO: 12;
- (e) CDR1 comprising or consisting of an amino acid sequence as shown in SEQ ID NO: 13, CDR2 comprising or consisting of an amino acid sequence as shown in SEQ ID NO: 14, and CDR3 comprising or consisting of an amino acid sequence as shown in SEQ ID NO: 15;
- (f) CDR1 comprising or consisting of an amino acid sequence as shown in SEQ ID NO: 16, CDR2 comprising or consisting of an amino acid sequence as shown in SEQ ID NO: 17, and CDR3 comprising or consisting of an amino acid sequence as shown in SEQ ID NO: 18;
- (g) CDR1 comprising or consisting of an amino acid sequence as shown in SEQ ID NO: 19, CDR2 comprising or consisting of an amino acid sequence as shown in SEQ ID NO: 20, and CDR3 comprising or consisting of an amino acid sequence as shown in SEQ ID NO: 21;
- (h) CDR1 comprising or consisting of an amino acid sequence as shown in SEQ ID NO: 22, CDR2 comprising or consisting of an amino acid sequence as shown in SEQ ID NO: 23, and CDR3 comprising or consisting of an amino acid sequence as shown in SEQ ID NO: 24;
- (i) CDR1 comprising or consisting of an amino acid sequence as shown in SEQ ID NO: 25, CDR2 comprising or consisting of an amino acid sequence as shown in SEQ ID NO: 26, and CDR3 comprising or consisting of an amino acid sequence as shown in SEQ ID NO: 27;
- (j) CDR1 comprising or consisting of an amino acid sequence as shown in SEQ ID NO: 28, CDR2 comprising or consisting of an amino acid sequence as shown in SEQ ID NO: 29, and CDR3 comprising or consisting of an amino acid sequence as shown in SEQ ID NO: 30;
- (k) CDR1 comprising or consisting of an amino acid sequence as shown in SEQ ID NO: 31, CDR2 comprising or consisting of an amino acid sequence as shown in SEQ ID NO: 32, and CDR3 comprising or consisting of an amino acid sequence as shown in SEQ ID NO: 33; and
- (l) CDR1 comprising or consisting of an amino acid sequence as shown in SEQ ID NO: 34, CDR2 comprising or consisting of an amino acid sequence as shown in SEQ ID NO: 35, and CDR3 comprising or consisting of an amino acid sequence as shown in SEQ ID NO: 36.

In some embodiments, at least one immunoglobulin single variable domain (for example, VHH), wherein the VHH comprises CDR1, CDR2 and CDR3, and wherein CDR1, CDR2 and CDR3 are selected from the group comprising:
- (a) CDR1 with an amino acid sequence as shown in SEQ ID NO: 1, CDR2 with an amino acid sequence as shown in SEQ ID NO: 2, and CDR3 with an amino acid sequence as shown in SEQ ID NO: 3;
- (b) CDR1 with an amino acid sequence as shown in SEQ ID NO: 4, CDR2 with an amino acid sequence as shown in SEQ ID NO: 5, and CDR3 with an amino acid sequence as shown in SEQ ID NO: 6;
- (c) CDR1 with an amino acid sequence as shown in SEQ ID NO: 7, CDR2 with an amino acid sequence as shown in SEQ ID NO: 8, and CDR3 with an amino acid sequence as shown in SEQ ID NO: 9;
- (d) CDR1 with an amino acid sequence as shown in SEQ ID NO: 10, CDR2 with an amino acid sequence as shown in SEQ ID NO: 11, and CDR3 with an amino acid sequence as shown in SEQ ID NO: 12;
- (e) CDR1 with an amino acid sequence as shown in SEQ ID NO: 13, CDR2 with an amino acid sequence as shown in SEQ ID NO: 14, and CDR3 with an amino acid sequence as shown in SEQ ID NO: 15;
- (f) CDR1 with an amino acid sequence as shown in SEQ ID NO: 16, CDR2 with an amino acid sequence as shown in SEQ ID NO: 17, and CDR3 with an amino acid sequence as shown in SEQ ID NO: 18;
- (g) CDR1 with an amino acid sequence as shown in SEQ ID NO: 19, CDR2 with an amino acid sequence as shown in SEQ ID NO: 20, and CDR3 with an amino acid sequence as shown in SEQ ID NO: 21;
- (h) CDR1 with an amino acid sequence as shown in SEQ ID NO: 22, CDR2 with an amino acid sequence as shown in SEQ ID NO: 23, and CDR3 with an amino acid sequence as shown in SEQ ID NO: 24;
- (i) CDR1 with an amino acid sequence as shown in SEQ ID NO: 25, CDR2 with an amino acid sequence as shown in SEQ ID NO: 26, and CDR3 with an amino acid sequence as shown in SEQ ID NO: 27;
- (j) CDR1 with an amino acid sequence as shown in SEQ ID NO: 28, CDR2 with an amino acid sequence as shown in SEQ ID NO: 29, and CDR3 with an amino acid sequence as shown in SEQ ID NO: 30;
- (k) CDR1 with an amino acid sequence as shown in SEQ ID NO: 31, CDR2 with an amino acid sequence as shown in SEQ ID NO: 32, and CDR3 with an amino acid sequence as shown in SEQ ID NO: 33; and
- (l) CDR1 with an amino acid sequence as shown in SEQ ID NO: 34, CDR2 with an amino acid sequence as shown in SEQ ID NO: 35, and CDR3 with an amino acid sequence as shown in SEQ ID NO: 36.

Anti-PD-1 Antibodies Defined via the Sequence of VHH

In some embodiments, the anti-PD-1 antibodies comprises at least one immunoglobulin single variable domain (for example, VHH), wherein the VHH comprises or consists of:
- (A) the amino acid sequence shown in any of SEQ ID NOs: 37-49;
- (B) an amino acid sequence which is at least 85%, at least 90%, or at least 95% identical to any of SEQ ID NOs: 37-49; or
- (C) an amino acid sequence with addition, deletion and/or substitution of one or more (for example, 1, 2, 3, 4, 5, 6, 7, 8, 9 or 10) amino acids compared with any of SEQ ID NOs: 37-49.

In other embodiments, the amino acid sequences of VHH can be at least 85%, 86%, 87%, 88%, 89%, 90%, 91%, 92%, 93%, 94%, 95%, 96%, 97%, 98% or 99% identical to the respective sequences set forth above. As an illustrative example, the antibody may comprise a VHH with at least 85%, 86%, 87%, 88%, 89%, 90%, 91%, 92%, 93%, 94%, 95%, 96%, 97%, 98% or 99% sequence identity to SEQ ID NO: 37.

In some further embodiments, the anti-PD-1 antibodies may contain conservative substitution or modification of amino acids in the variable regions of the heavy chain and/or light chain. It is understood in the art that certain conservative sequence modification can be made which do not remove antigen binding. See, e.g., Brummell et al. (1993) Biochem 32:1180-8; de Wildt et al. (1997) Prot. Eng. 10:835-41; Komissarov et al. (1997) J. Biol. Chem. 272: 26864-26870; Hall et al. (1992) J. Immunol. 149:1605-12; Kelley and O'Connell (1993) Biochem. 32:6862-35; Adib-Conquy et al. (1998) Int. Immunol. 10:341-6 and Beers et al. (2000) Clin. Can. Res. 6:2835-43.

As described above, the term "conservative substitution", as used herein, refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

Binning and Epitope Mapping

It will further be appreciated the disclosed antibodies will associate with, or bind to, discrete epitopes or immunogenic determinants presented by the selected target or fragment thereof. In some embodiments, epitope or immunogenic determinants include chemically active surface groupings of molecules such as amino acids, sugar side chains, phosphoryl groups, or sulfonyl groups. In some embodiments, epitopes may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In some embodiments, an antibody is said to specifically bind (or immune-specifically bind or react) an antigen when it preferentially recognizes its target antigen in a complex mixture of proteins and/or macromolecules. In some embodiments, an antibody is said to specifically bind an antigen when the equilibrium dissociation constant ($K_D$) is less than or equal to $10^{-6}$M or less than or equal to $10^{-7}$M, more preferably when the e $K_D$ is less than or equal to $10^{-8}$M, and even more preferably when the $K_D$ is less than or equal to $10^{-9}$M.

Epitopes formed from contiguous amino acids (sometimes referred to as "linear" or "continuous" epitopes) are typically retained upon protein denaturing, whereas epitopes formed by tertiary folding are typically lost upon protein denaturing. In any event an antibody epitope typically includes at least 3, and more usually, at least 5 or 8-10 amino acids in a unique spatial conformation.

In this respect, it will be appreciated that, in some embodiments, an epitope may be associated with, or reside in, one or more regions, domains or motifs of, for example, the PD-1 protein. Similarly, the art-recognized term "motif" will be used in accordance with its common meaning and shall generally refer to a short, conserved region of a protein that is typically ten to twenty contiguous amino acid residues.

In any event once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising antibody competition or antigen fragment expression on yeast are well known in the art.

As used herein, the term "binning" refers to methods used to group or classify antibodies based on their antigen binding characteristics and competition. While the techniques are useful for defining and categorizing the antibodies of the instant invention, the bins do not always directly correlate with epitopes and such initial determinations of epitope binding may be further refined and confirmed by other art-recognized methodology in the art and as described herein. However, it will be appreciated that empirical assignment of the antibodies to individual bins provides information that may be indicative of the therapeutic potential of the disclosed antibodies.

More specifically, one can determine whether a selected reference antibody (or fragment thereof) binds to the same epitope or cross competes for binding with a second test antibody (i.e., is in the same bin) by using methods known in the art and set forth in the Examples herein.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety).

Nucleic Acid Molecules Encoding Antibodies of the Invention

In some aspects, the invention is directed to an isolated nucleic acid molecule, comprising a nucleic acid sequence encoding VHHs as disclosed herein.

Nucleic acids of the invention can be obtained using standard molecular biology techniques. For antibodies obtained from an immunoglobulin gene library (e.g., using phage display techniques), a nucleic acid encoding such antibodies can be recovered from the gene library.

Exemplary nucleic acids molecules of the invention are those set forth SEQ ID Nos: 50-62, respectively. In some embodiments, the nucleic acids share an at least 80% (e.g. at least 85%, 86%, 87%, 88%, 89%, 90%, 91%, 92%, 93%, 94%, 95%, 96%, 97%, 98%, or 99%) sequence identity to SEQ ID NOs: 17-20, respectively. In some embodiments, the percentage of identity is derived from the degeneracy of the genetic code, and the encoded protein sequences remain unchanged.

The nucleic acid molecules that encodes the anti-PD-1 antibodies can be inserted into a vector for further cloning (amplification of the DNA) or for expression, using recombinant techniques known in the art. In another embodiment, the antibody may be produced by homologous recombination known in the art. DNA encoding the monoclonal antibody is readily isolated and sequenced using conventional procedures (e.g., by using oligonucleotide probes that are capable of binding specifically to genes encoding the heavy chain of the antibody). Many vectors are available. The vector components generally include, but are not limited to, one or more of the following: a signal sequence, an origin of replication, one or more marker genes, an enhancer element, a promoter (e.g. SV40, CMV, EF-1α), and a transcription termination sequence. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Selectable marker genes may include the dihydrofolate reductase (DHFR) gene (for use in dhfr-host cells with methotrexate selection/amplification) and the neo gene (for G418 selection).

In some embodiments, the vector system includes mammalian, bacterial, yeast systems, etc, and comprises plasmids such as, but not limited to, pALTER, pBAD, pcDNA, pCal, pL, pET, pGEMEX, pGEX, pCI, pCMV, pEGFP, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS420, pLexA, pACT2.2 etc, and other laboratory and commercially available vectors. Suitable vectors may include, plasmid, or viral vectors (e.g., replication defective retroviruses, adenoviruses and adeno-associated viruses). In one embodiment of the invention, the vector may be pET, for instance, pETbac containing genes of hexa-histidine- and c-Myc-tag.

Vectors comprising the nucleic acid sequence encoding the PD-1 binding molecule can be introduced to a host cell for cloning or gene expression. Suitable host cells for cloning or expressing the DNA in the vectors herein are the prokaryote, yeast, or higher eukaryote cells. Suitable prokaryotes for this purpose include eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*.

In addition to prokaryotes, eukaryotic microbes such as filamentous fungi or yeast are suitable cloning or expression hosts for anti-PD-1 antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Other suitable host cells for the expression of the anti-PD-1 antibodies provided here are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Host cells are transformed with the above-described expression or cloning vectors for anti-PD-1 antibody production and cultured in conventional nutrient media modified as appropriate for inducing promoters, selecting transformants, or amplifying the genes encoding the desired sequences.

The host cells used to produce the anti-PD-1 antibodies provided herein may be cultured in a variety of media. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the host cells. In addition, any of the media described in Ham et al., Meth. Enz. 58: 44 (1979), Barnes et al., Anal. Biochem. 102: 255 (1980), U.S. Pat. No. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody prepared from the cells can be purified using, for example, hydroxylapatite chromatography, gel electrophoresis, dialysis, DEAE-cellulose ion exchange chromatography, ammonium sulfate precipitation, salting out, and affinity chromatography, with affinity chromatography being the preferred purification technique.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Pharmaceutical Compositions

In some aspects, the invention is directed to a pharmaceutical composition comprising at least one PD-1 binding molecule as disclosed herein and a pharmaceutically acceptable carrier.

Components of the Compositions

The pharmaceutical composition may optionally contain one or more additional pharmaceutically active ingredients, such as another antibody or a drug. The pharmaceutical compositions of the invention also can be administered in a combination therapy with, for example, another immune-stimulatory agent, anti-cancer agent, an antiviral agent, or a vaccine, such that the anti-PD-1 antibody enhances the immune response against the vaccine. A pharmaceutically acceptable carrier can include, for example, a pharmaceutically acceptable liquid, gel or solid carriers, an aqueous medium, a non-aqueous medium, an anti-microbial agent, isotonic agents, buffers, antioxidants, anesthetics, suspending/dispersing agent, a chelating agent, a diluent, adjuvant, excipient or a nontoxic auxiliary substance, other known in the art various combinations of components or more.

Suitable components may include, for example, antioxidants, fillers, binders, disintegrating agents, buffers, preservatives, lubricants, flavorings, thickening agents, coloring agents, emulsifiers or stabilizers such as sugars and cyclodextrin. Suitable anti-oxidants may include, for example, methionine, ascorbic acid, EDTA, sodium thiosulfate, platinum, catalase, citric acid, cysteine, mercapto glycerol, thioglycolic acid, Mercapto sorbitol, butyl methyl anisole, butylated hydroxy toluene and/or propylgalacte. As disclosed in the present invention, in a solvent containing an antibody or an antigen-binding fragment of the present invention discloses compositions include one or more anti-oxidants such as methionine, reducing antibody or antigen binding fragment thereof may be oxidized. The oxidation reduction may prevent or reduce a decrease in binding affinity, thereby enhancing antibody stability and extended shelf life. Thus, in some embodiments, the present invention provides a composition comprising one or more antibodies or antigen binding fragment thereof and one or more anti-oxidants such as methionine. The present invention further provides a variety of methods, wherein an antibody or antigen binding fragment thereof is mixed with one or more anti-oxidants, such as methionine, so that the antibody or antigen binding fragment thereof can be prevented from oxidation, to extend their shelf life and/or increased activity.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

Administration, Formulation and Dosage

The pharmaceutical composition of the invention may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms;

including, but not limited to, tablets, capsules, powders, granules, ointments, solutions, suppositories, enemas, injections, inhalants, and aerosols. The appropriate formulation and route of administration may be selected according to the intended application and therapeutic regimen.

Suitable formulations for enteral administration include hard or soft gelatin capsules, pills, tablets, including coated tablets, elixirs, suspensions, syrups or inhalations and controlled release forms thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Similarly, the particular dosage regimen, i.e., dose, timing and repetition, will depend on the particular individual and that individual's medical history, as well as empirical considerations such as pharmacokinetics (e.g., half-life, clearance rate, etc.).

Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In some embodiments, the dosage administered may be adjusted or attenuated to manage potential side effects and/or toxicity. Alternatively, sustained continuous release formulations of a subject therapeutic composition may be appropriate.

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action that achieve the desired effect without causing substantial harmful or deleterious side-effects.

In general, the PD-1 binding molecules may be administered in various ranges. In some embodiments, the PD-1 binding molecules as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

In any event, the antibody or the antigen binding portion thereof of the invention is preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like.

In certain preferred embodiments, the course of treatment involving the antibody or the antigen-binding portion thereof of the instant invention will comprise multiple doses of the selected drug product over a period of weeks or months. More specifically, the antibody or the antigen-binding portion thereof of the instant invention may be administered once every day, every two days, every four days, every week, every ten days, every two weeks, every three weeks, every month, every six weeks, every two months, every ten weeks or every three months. In this regard, it will be appreciated that the dosages may be altered or the interval may be adjusted based on patient response and clinical practices.

Dosages and regimens may also be determined empirically for the disclosed therapeutic compositions in individuals who have been given one or more administration(s). For example, individuals may be given incremental dosages of a therapeutic composition produced as described herein. In selected embodiments, the dosage may be gradually increased or reduced or attenuated based respectively on empirically determined or observed side effects or toxicity. To assess efficacy of the selected composition, a marker of the specific disease, disorder or condition can be followed as described previously. For cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or a tumorigenic antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

Compatible formulations for parenteral administration (e.g., intravenous injection) may comprise the PD-1 binding molecules as provided herein in concentrations of from about 10 µg/ml to about 100 mg/ml. In some embodiments, the concentrations of the PD-1 binding molecule may comprise 20 µg/ml, 40 µg/ml, 60 µg/ml, 80 µg/ml, 100 µg/ml, 200 µg/ml, 300, µg/ml, 400 µg/ml, 500 µg/ml, 600 µg/ml, 700 µg/ml, 800 µg/ml, 900 µg/ml or 1 mg/ml. In other preferred embodiments, the concentration of the PD-1 binding molecule comprise 2 mg/ml, 3 mg/ml, 4 mg/ml, 5 mg/ml, 6 mg/ml, 8 mg/ml, 10 mg/ml, 12 mg/ml, 14 mg/ml, 16 mg/ml, 18 mg/ml, 20 mg/ml, 25 mg/ml, 30 mg/ml, 35 mg/ml, 40 mg/ml, 45 mg/ml, 50 mg/ml, 60 mg/ml, 70 mg/ml, 80 mg/ml, 90 mg/ml or 100 mg/ml.

Applications of the Invention

The PD-1 binding molecules of the present invention have numerous in vitro and in vivo utilities. For example, these molecules can be administered to cells in culture, in vitro or ex vivo, or to human subjects, e.g., in vivo, to enhance immunity in a variety of situations. The immune response can be augmented, stimulated or up-regulated.

Preferred subjects include human patients in need of enhancement of an immune response. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, the anti-PD-1 antibodies can be administered together with an antigen of interest or the antigen may already be present in the subject to be treated (e.g., a tumor-bearing or virus-bearing subject). When anti-PD-1 antibodies are administered together with another agent, the two can be administered in either order or simultaneously.

The invention further provides methods for detecting the presence of PD-1 antigen in a sample, or measuring the amount of human PD-1 antigen, comprising contacting the sample, and a control sample, with the PD-1 binding molecules, under conditions that allow for formation of a complex between the PD-1 binding molecule and PD-1. The formation of a complex is then detected, wherein a difference complex formation between the sample compared to the control sample is indicative of the presence of PD-1 antigen in the sample. Moreover, the PD-1 binding molecules of the invention can be used to purify human PD-1 via immunoaffinity purification.

Treatment of Cancers

Conditions and disorders associated with PD-1 can be an immunity-related disease or disorder. In some embodiments, the PD-1 associated conditions and disorders include tumors and cancers, for example, non-small cell lung cancer, small cell lung cancer, renal cell cancer, colorectal cancer, ovarian cancer, breast cancer, pancreatic cancer, gastric carcinoma, bladder cancer, esophageal cancer, mesothelioma, melanoma, head and neck cancer, thyroid cancer, sarcoma, prostate cancer, glioblastoma, cervical cancer, thymic carcinoma, leukemia, lymphomas, myelomas, mycoses fungoids, merkel cell cancer, and other hematologic malignancies, such as classical Hodgkin lymphoma (CHL), primary mediastinal large B-cell lymphoma, T-cell/histiocyte-rich B-cell lymphoma, EBV-positive and -negative PTLD, and EBV-associated diffuse large B-cell lymphoma (DLBCL), plasmablastic lymphoma, extranodal NK/T-cell lymphoma, nasopharyngeal carcinoma, and HHV8-associated primary effusion lymphoma, Hodgkin's lymphoma, neoplasm of the central nervous system (CNS), such as primary CNS lymphoma, spinal axis tumor, brain stem glioma. In certain embodiments, the tumors and cancers are metastatic, especially metastatic tumors expressing PD-L1. In certain embodiments, the PD-1 associated conditions and disorders include autoimmune diseases, such as systemic lupus erythematosus (SLE), psoriasis, systemic scleroderma, autoimmune diabetes and the like. In certain embodiments, the PD-1 associated conditions and disorders include infectious disease such as chronic viral infection, for example, viral infection of hepatitis B, hepatitis C, herpes virus, Epstein-Barr virus, HIV, cytomegalovirus, herpes simplex virus type I, herpes simplex virus type 2, human papilloma virus, adenovirus, Kaposi West sarcoma associated herpes virus epidemics, thin ring virus (Torquetenovirus), JC virus or BK virus.

The antibody or the antigen-binding portion thereof may be used in combination with chemical therapies or radiotherapies.

Combined use with Chemotherapies

The antibody or the antigen-binding portion thereof may be used in combination with an anti-cancer agent, a cytotoxic agent or chemotherapeutic agent.

The term "anti-cancer agent" or "anti-proliferative agent" means any agent that can be used to treat a cell proliferative disorder such as cancer, and includes, but is not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with the disclosed site-specific antibodies prior to administration. More specifically, In some embodiments selected anti-cancer agents will be linked to the unpaired cysteines of the engineered antibodies to provide engineered conjugates as set forth herein. Accordingly, such engineered conjugates are expressly contemplated as being within the scope of the instant invention. In other embodiments, the disclosed anti-cancer agents will be given in combination with site-specific conjugates comprising a different therapeutic agent as set forth above.

As used herein the term "cytotoxic agent" means a substance that is toxic to the cells and decreases or inhibits the function of cells and/or causes destruction of cells. In some embodiments, the substance is a naturally occurring molecule derived from a living organism. Examples of cytotoxic agents include, but are not limited to, small molecule toxins or enzymatically active toxins of bacteria (e.g., Diptheria toxin, Pseudomonas endotoxin and exotoxin, Staphylococcal enterotoxin A), fungal (e.g., α-sarcin, restrictocin), plants (e.g., abrin, ricin, modeccin, viscumin, pokeweed antiviral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *Saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant invention a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI.

Examples of anti-cancer agents that may be used in combination with the site-specific constructs of the present invention (either as a component of a site specific conjugate or in an unconjugated state) include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, erlotinib, vemurafenib, crizotinib, sorafenib, ibrutinib, enzalutamide, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, OR), razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatraxate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LURTOTECAN® topoisomerase 1 inhibitor; ABARELIX® rmRH; Vinorelbine and Esperamicins and pharmaceutically acceptable salts, acids or derivatives of any of the above.

Combined use with Radiotherapies

The present invention also provides for the combination of the antibody or the antigen-binding portion thereof with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and the disclosed conjugates may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

Diagnosis

The invention provides in vitro and in vivo methods for detecting, diagnosing or monitoring proliferative disorders and methods of screening cells from a patient to identify tumor cells including tumorigenic cells. Such methods include identifying an individual having cancer for treatment or monitoring progression of a cancer, comprising contacting the patient or a sample obtained from a patient (either in vivo or in vitro) with an antibody as described herein and detecting presence or absence, or level of association, of the antibody to bound or free target molecules in the sample. In some embodiments, the antibody will comprise a detectable label or reporter molecule as described herein.

In some embodiments, the association of the antibody with particular cells in the sample can denote that the sample may contain tumorigenic cells, thereby indicating that the individual having cancer may be effectively treated with an antibody as described herein.

Samples can be analyzed by numerous assays, for example, radioimmunoassays, enzyme immunoassays (e.g. ELISA), competitive-binding assays, fluorescent immunoassays, immunoblot assays, Western Blot analysis and flow cytometry assays. Compatible in vivo theragnostic or diagnostic assays can comprise art recognized imaging or monitoring techniques, for example, magnetic resonance imaging, computerized tomography (e.g. CAT scan), positron tomography (e.g., PET scan), radiography, ultrasound, etc., as would be known by those skilled in the art.

Pharmaceutical Packs and Kits

Pharmaceutical packs and kits comprising one or more containers, comprising one or more doses of the antibody or the antigen-binding portion thereof are also provided. In some embodiments, a unit dosage is provided wherein the unit dosage contains a predetermined amount of a composition comprising, for example, the antibody or the antigen-binding portion thereof, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, In some embodiments, the conjugate composition may be provided as a lyophilized powder that may be reconstituted upon addition of an appropriate liquid, for example, sterile water or saline solution. In certain preferred embodiments, the composition comprises one or more substances that inhibit protein aggregation, including, but not limited to, sucrose and arginine. Any label on, or associated with, the container(s) indicates that the enclosed conjugate composition is used for treating the neoplastic disease condition of choice.

The present invention also provides kits for producing single-dose or multi-dose administration units of site-specific conjugates and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed conjugates in a conjugated or unconjugated form. In other preferred embodiments, the container(s) comprise a sterile access port (for example the container may be an intravenous solution bag or a vial having a stopper pierceable by a hypodermic injection needle). Such kits will generally contain in a suitable container a pharmaceutically acceptable formulation of the engineered conjugate and, optionally, one or more anti-cancer agents in the same or different containers. The kits may also contain other pharmaceutically acceptable formulations, either for diagnosis or combined therapy. For example, in addition to the antibody or the antigen-binding portion thereof of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents.

More specifically the kits may have a single container that contains the disclosed the antibody or the antigen-binding portion thereof, with or without additional components, or they may have distinct containers for each desired agent. Where combined therapeutics are provided for conjugation, a single solution may be pre-mixed, either in a molar equivalent combination, or with one component in excess of the other. Alternatively, the conjugates and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous or saline solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody or the antigen-binding portion thereof and any optional components to a patient, e.g., one or more needles, I.V. bags or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained.

Sequence Listing Summary

Appended to the instant application is a sequence listing comprising a number of nucleic acid and amino acid sequences. The following Table A provides a summary of the included sequences.

TABLE A

| SEQ ID NO. | Description |
|---|---|
| 1 | CDR1 of AP17R1-2H2 or AP17R1-2H2-Z1 |
| 2 | CDR2 of AP17R1-2H2 or AP17R1-2H2-Z1 |
| 3 | CDR3 of AP17R1-2H2 or AP17R1-2H2-Z1 |
| 4 | CDR1 of AP17R1-2H2-Z1-R1-4B2 |
| 5 | CDR2 of AP17R1-2H2-Z1-R1-4B2 |
| 6 | CDR3 of AP17R1-2H2-Z1-R1-4B2 |
| 7 | CDR1 of AP17R1-2H2-Z1-R1-4D8 |
| 8 | CDR2 of AP17R1-2H2-Z1-R1-4D8 |
| 9 | CDR3 of AP17R1-2H2-Z1-R1-4D8 |
| 10 | CDR1 of AP17R1-2H2-Z1-R1-6E1 |
| 11 | CDR2 of AP17R1-2H2-Z1-R1-6E1 |
| 12 | CDR3 of AP17R1-2H2-Z1-R1-6E1 |
| 13 | CDR1 of AP17R1-2H2-Z1-R1-14A1 |
| 14 | CDR2 of AP17R1-2H2-Z1-R1-14A1 |
| 15 | CDR3 of AP17R1-2H2-Z1-R1-14A1 |
| 16 | CDR1 of AP17R1-2H2-Z1-R1-14F1 |
| 17 | CDR2 of AP17R1-2H2-Z1-R1-14F1 |
| 18 | CDR3 of AP17R1-2H2-Z1-R1-14F1 |
| 19 | CDR1 of AP17R1-2H2-Z1-R1-14B3 |
| 20 | CDR2 of AP17R1-2H2-Z1-R1-14B3 |
| 21 | CDR3 of AP17R1-2H2-Z1-R1-14B3 |
| 22 | CDR1 of AP17R1-2H2-Z1-R1-14F3 |
| 23 | CDR2 of AP17R1-2H2-Z1-R1-14F3 |
| 24 | CDR3 of AP17R1-2H2-Z1-R1-14F3 |
| 25 | CDR1 of AP17R1-2H2-Z1-R1-27A2 |
| 26 | CDR2 of AP17R1-2H2-Z1-R1-27A2 |
| 27 | CDR3 of AP17R1-2H2-Z1-R1-27A2 |
| 28 | CDR1 of AP17R1-2H2-Z1-R1-29B2 |
| 29 | CDR2 of AP17R1-2H2-Z1-R1-29B2 |
| 30 | CDR3 of AP17R1-2H2-Z1-R1-29B2 |
| 31 | CDR1 of AP17R1-2H2-Z1-R1-29B6 |
| 32 | CDR2 of AP17R1-2H2-Z1-R1-29B6 |
| 33 | CDR3 of AP17R1-2H2-Z1-R1-29B6 |
| 34 | CDR1 of AP17R1-2H2-Z1-R1-30D3 |
| 35 | CDR2 of AP17R1-2H2-Z1-R1-30D3 |
| 36 | CDR3 of AP17R1-2H2-Z1-R1-30D3 |
| 37 | Full-length sequence of AP17R1-2H2 |
| 38 | Full-length sequence of AP17R1-2H2-Z1 |
| 39 | Full-length sequence of AP17R1-2H2-Z1-R1-4B2 |
| 40 | Full-length sequence of AP17R1-2H2-Z1-R1-4D8 |
| 41 | Full-length sequence of AP17R1-2H2-Z1-R1-6E1 |
| 42 | Full-length sequence of AP17R1-2H2-Z1-R1-14A1 |
| 43 | Full-length sequence of AP17R1-2H2-Z1-R1-14F1 |
| 44 | Full-length sequence of AP17R1-2H2-Z1-R1-14B3 |
| 45 | Full-length sequence of AP17R1-2H2-Z1-R1-14F3 |
| 46 | Full-length sequence of AP17R1-2H2-Z1-R1-27A2 |
| 47 | Full-length sequence of AP17R1-2H2-Z1-R1-29B2 |
| 48 | Full-length sequence of AP17R1-2H2-Z1-R1-29B6 |
| 49 | Full-length sequence of AP17R1-2H2-Z1-R1-30D3 |
| 50 | Nucleotide sequence encoding AP17R1-2H2 |
| 51 | Nucleotide sequence encoding AP17R1-2H2-Z1 |
| 52 | Nucleotide sequence encoding AP17R1-2H2-Z1-R1-4B2 |
| 53 | Nucleotide sequence encoding AP17R1-2H2-Z1-R1-4D8 |
| 54 | Nucleotide sequence encoding AP17R1-2H2-Z1-R1-6E1 |
| 55 | Nucleotide sequence encoding AP17R1-2H2-Z1-R1-14A1 |
| 56 | Nucleotide sequence encoding AP17R1-2H2-Z1-R1-14F1 |
| 57 | Nucleotide sequence encoding AP17R1-2H2-Z1-R1-14B3 |
| 58 | Nucleotide sequence encoding AP17R1-2H2-Z1-R1-14F3 |
| 59 | Nucleotide sequence encoding AP17R1-2H2-Z1-R1-27A2 |
| 60 | Nucleotide sequence encoding AP17R1-2H2-Z1-R1-29B2 |
| 61 | Nucleotide sequence encoding AP17R1-2H2-Z1-R1-29B6 |
| 62 | Nucleotide sequence encoding AP17R1-2H2-Z1-R1-30D3 |

EXAMPLES

The present invention, thus generally described, will be understood more readily by reference to the following Examples, which are provided by way of illustration and are not intended to be limiting of the instant invention. The Examples are not intended to represent that the experiments below are all or the only experiments performed.

Example 1

Preparation of Materials

1. Preparation of Materials
1.1 Commercial Materials
Information on the commercially available materials used in the examples are provided in Table 1.

TABLE 1

Commercial materials

| Materials | Vendor | Cat. |
|---|---|---|
| FITC mouse anti-human CD279 Ab | eBioscience | Cat. #11-9969-42 |
| FITC goat anti-human IgG Fc | Bethlyl | Cat. #A80-204F |
| PE goat anti-mouse IgG Fc | Abcam | Cat. #ab98742 |
| R-PE goat anti-human IgG Fc | Jackson Immuno Research | Cat. #109-115-098 |
| PE goat anti-mouse IgG Fc | Abcam | Cat. #Ab98742 |
| SA-PE | eBioscience | Cat. #12-4317 |
| HRP goat anti-human IgG Fc | Bethyl | Cat. #A80-304P |
| Streptavidin-HRP | Invitrogen | Cat. #SNN1004 |
| Ficoll-Paque™ PLUS | GE Healthcare | Cat. #17-1440-02 |
| Human Monocyte Enrichment kit | STEMCELL | Cat. #19059 |
| Human CD4+ T Cell Enrichment kit | STEMCELL | Cat. #19052 |
| Recombinant human GM-CSF | Amoytop Biotech | Cat. #S10980039 |
| Recombinant human IL-4 | R&D | Cat. #204-IL-010 |
| Standard recombinant human IFN-γ | PeproTech | Cat. #300-02 |
| Human IFN-γ capture antibody | Pierce | Cat. #M700A |
| Human IFN-γ detection antibody | Pierce | Cat. #M701B |
| SA-HRP | Invitrogen | Cat. #SNN1004 |
| Human PD-1, His tag | Sino Biological | Cat. #10377-H08H |
| Cynomolgus PD-1, His tag | AcrobioSystem | Cat. #PDl-C5223 |
| Cynomolgus PD-1, hFc tag | Sino Biological | Cat. #90311-C02H |
| Mouse PD-1, His tag | Sino Biological | Cat. #50124-M08H |
| Human PD-L2, His tag | Sino Biological | Cat. #10292-H08H |
| Human BTLA, His tag | AcrobioSystems | Cat. #BTA-H52E0 |
| Cynomolgus PD-1, His tag | R&D Systems | Cat. #85509-PD |

1.2 Material Code

The codes or abbreviation for the materials including benchmark antibodies, the extracellular domains and the cells are summarized in Table 2.

TABLE 2

Material Code

| Material Name | Code or Abbreviation |
|---|---|
| Benchmark antibody 1 (Opdivo ®, Nivolumab) | BMK1, BMK1.IgG4, W305-BMK1.IgG4 or W305-BMK1.hIgG4 |
| Benchmark antibody 3 | BMK3 or BMK3.IgG4, W305-BMK3.hIgG4, or W305-BMK3.hIgG4K |
| Human IgG4 isotype control | hIgG4 Isotype, Isotype, human IgG4 |
| Human PD-1 extracellular domain, mFc tag | hPro1.ECD.mFc |
| Mouse PD-1 extracellular domain, mFc tag | mPro1.ECD.mFc |
| Human PD-L1 extracellular domain, mFc tag | hProL1.ECD.mFc |
| Mouse PD-L1 extracellular domain, mFc tag | mProL1.ECD.mFc |
| Human CD28 extracellular domain, mFc tag | hCD28.ECD.mFc |
| Human CTLA-4 extracellular domain, His tag | hCTLA-4.ECD.His |
| Human ICOS extracellular domain, mFc tag | hICOS.ECD.mFc |
| Human PD-1 extracellular domain, His tag | hPro1.ECD.His |
| Mouse PD-1 extracellular domain, His tag | mPro1.ECD.His |
| Human PD-L2 extracellular domain, His tag | hPro1L2.ECD.His |
| Cynomolgus PD-1 extracellular domain, hFc tag | cynoPro1.ECD.hFc |
| Cynomolgus PD-L1 extracellular domain, hFc tag | cynoProL1.ECD.hFc |
| Cynomolgus PD-1 extracellular domain, His tag | cynoPro1.ECD.His |
| Human BTLA extracellular domain, His | hBTLA.ECD.His |
| Human PD-1-expressing CHO-S cell | CHO-S.hPro1.C6 |
| Mouse PD-1-expressing 293F cell | 293F.mPro1.B4 |
| W3056 lead antibody (VHH-Fc(hIgG4) fusion) | W3056-AP17R1-2H2-Z1-R1-14A1-FC(IgG4.SP) |
| W3056 lead parental antibody (VHH) | AP17R1-2H2 |
| W3056 lead parental antibody (VHH-Fc(hIgG4) fusion) | AP17R1-2H2-Fc(IgG4), AP17R1-2H2-FC(IgG4.SP), W3056-AP17R1-2H2-FC(IgG4.SP) |

2. Production of Antigens

DNA sequences encoding the antigens hPro1.ECD (Genbank Accession No. NP_005009.2), hProL1.ECD (Genbank Accession No. NP_054862.1), hCTLA-4.ECD (Genbank Accession No. NP_005205.2), hCD28.ECD (Genbank Accession No. NP_006130.1), hICOS.ECD (Genbank Accession No. NP_036224.1) and mPro1ECD (Genbank Accession No. NP_032824.1), mProL1.ECD (Genbank Accession No. NP_068693.1) were synthesized in Sangon Biotech (Shanghai, China), and then subcloned into modified pcDNA3.3 expression vectors with different tag (such as 6×his, human Fc, or mouse Fc) at C-terminus. The resultant expression vectors were further purified. Expi293 cells (Invitrogen-A14527) were transfected with the purified expression vectors. The transfected cells were cultured for 5 days and supernatant was collected for protein purification using Ni-NTA column (GE Healthcare, 175248) or Protein A column (GE Healthcare, 175438) or Protein G column (GE Healthcare, 170618). The obtained antigens were quality controlled by SDS-PAGE and SEC size exclusion chromatography, and then stored at −80° C.

3. Production of Benchmark Antibodies

DNA sequences encoding the variable region of ant-PD-1 antibodies were synthesized in Sangon Biotech (Shanghai, China), and then subcloned into modified pcDNA3.3 expression vectors with constant region of human IgG4 (S228P). The heavy and light chain variable region sequences of BMK1 are the same as the approved anti-PD-1 antibody Opdivo (the sequence of clone 5C4 in PCT application WO2006/121168A1). The heavy and light chain variable region sequences of BMK3 antibody are the same as the sequence of clone 1B8 in US Patent No. US8168757B2.

Plasmids containing the DNA sequences encoding the heavy chain and light chain regions of the respective anti-PD-1 antibodies were co-transfected into Expi293 cells. The transfected cells were cultured for 5 days and supernatant was collected for protein purification using Protein A column (GE Healthcare, 175438) or Protein G column (GE Healthcare, 170618). The obtained antibodies were analyzed by SDS-PAGE and SEC, and then stored at −80° C.

3. Establishment of Stable Cell Lines

Using Lipofectamine 2000, CHO-S or 293F cells were transfected with the expression vector containing gene encoding full length human PD-1 or mouse PD-1. Cells were cultured in medium containing proper selection pressure. Human PD-1 high expression stable cell line (WBP305.CHO-S.hPro1.C6) and mouse PD-1 high expression stable cell line (WBP305.293F.mPro1.B4) were obtained by limiting dilution.

EXAMPLE 2

Production of VHH and Chimeric VHH-Fc (hIgG4) Protein

1. Immunization

To induce a humoral immune response directed towards PD-1 in camelid animals, the animals were subcutaneously injected with human and/or mouse PD-1 ECD proteins for 7 to 9 doses at 1 to 3 week intervals. The dose ranged from 50 ug to 200 ug per injection.

2. Serum Titer Detection

After immunization, the anti-PD-1 specific antibody serum titer was determined by ELISA. For ELISA test, ELISA plates (Nunc, Rochester, MN, USA) were coated with 1 µg/ml of recombinant his tagged human PD-1 ECD protein and mouse PD-1 ECD protein, respectively, and incubated overnight at 4° C. After blocking and washing, serial dilutions of pre-immune and immune sera were added and incubated at room temperature for 2 h, then followed by goat anti-Llama IgG-HRP (Novas Biologicals, Littleton, CO, USA) at room temperature for 1 h. After washing, TMB substrate (Invitrogen, Carlsbad, CA, USA) was added and the reaction was stopped by 2M HCl. The absorbance at 450 nm was read using a microplate reader (Molecular Device, Sunnyvale, CA, USA).

3. Phage Library Construction 50 ml blood samples were collected at 6-7 days after the last two injections, respectively. Peripheral blood mononuclear cells (PBMCs) were purified by density gradient centrifugation on Ficoll-Paque PLUS (GE Healthcare, Little Chalfont, UK), resulting in the isolation of approximately $8 \times 10^7$ PBMCs. Total RNA was extracted from the PBMCs and transcribed into cDNA using an oligo-dT primer and SuperScript III First-Strand Synthesis SuperMix System (Invitrogen, Carlsbad, CA, USA) according to the manufacturers' recommendations.

The cDNA was purified and then used as template to amplify the repertoire of Ig heavy chain-encoding gene segments with the use of signal peptide domain specific primers and CH2 domain specific primers. This amplification resulted in PCR fragments of approximately 900 bp (representing conventional IgGs) and 700 bp (representing heavy-chain IgGs that lack a CH1 domain). The two classes of heavy chain encoding genes were then size-separated on agarose gels and the genes encoding heavy-chain only IgG were purified by QIAquick Gel Extraction Kit (Qiagen, Hilden, Germany). The purified fragments were used as template to amplify the VHH repertoire with the use of framework1 (FR1) and framework4 (FR4) specific primer pairs. This amplification procedure introduced Sfi I restriction site at the 5' end of FR1 and a Not I restriction site at the 3' end of FR4. The repertoire of PCR-amplified VHH genes of about 300-400 bp was loaded on agarose gels and purified by QIAquick Gel Extraction Kit. The purified fragments were then cut with Sfi I and Not I and purified by QIAquick PCR Purification Kit (Qiagen, Hilden, Germany). The VHH gene fragments were finally ligated in phagemid vector pFL249 and electrotransformed into *E. coli* TG1. After transformation, the TG1 cells were cultured in SOC medium with shaking at 200 rpm for 1 h, then the *E. coli* TG1 were plated onto plates containing solid 2YT medium supplemented with 100 µg/mL Cab and 1% (w/v) glucose, and cultured at 37° C. overnight. The next day, the colonies were scraped into liquid 2YT medium supplemented with 1/3 (v/v) of 80% glycerol and were stored at −80° C.

4. Phage Display Selection of Anti-PD-1 Specific VIM Fragments

To select VHH fragments that would effectively bind to PD-1, the methods of protein panning and cell panning were employed.

For the protein panning, 20 µg of recombinant his tagged human and mouse PD-1 ECD protein were immobilized in 5 ml immune tube (Nunc, Rochester, MN, USA) overnight at 4° C. with shaking at 400 rpm, respectively. On the next day, after washing away unbound protein, the tube was blocked with 10% skim milk for 1 h at 25° C. Approximately $10^{12}$ cfu phages from the immune phage libraries added into non-coated immune tube blocked with 10% skim milk to deplete the non-specifically bound phage, then the treated phages were added into the tube and incubated at 25° C. for 2 h. After extensive washing with PBST, the nonspecifically adsorbed phages were discarded and the target specifically bound phages were eluted by Glycine-HCl (pH2.2) and then neutralized by 1M Tris-HCl (pH8.0) for infection of exponentially growing TG1 cells.

The infected TG1 cells were plated on 2YT agar plates containing 2% (w/v) glucose and 100 µg/ml ampicillin and cultured overnight at 37° C. On the next day, the colonies were scraped off the plate with 3 ml 2YT and frozen at −80° C. by adding in 1/3 (v/v) 80% glycerol. The scraped bacteria libraries were inoculated into 2YT-Carb containing 100 µg/ml ampicillin, and were infected with helper phage M13Ko7 in 2YT medium with 50 µg/ml kanamycin and 1 mM IPTG for phage rescue and used as input for the next round of panning.

For the cell panning, pre-incubation of $10^{12}$ cfu phages with $2\times10^6$-$1\times10^7$ CHO-S or 293F cells was performed for depletion of non-specific bound phage particles. Then the treated phages were incubated with $2\times10^6$-$1\times10^7$ PD-1 transfected CHO-S or 293F cells at 4° C. for 1 h with tumbling at 12 rpm. The cells were washed with ice cold 5% FBS-PBS and the cell bound phage particles were eluted as described above. For panning by Dynabeads, about $10^{12}$ cfu phages were first incubated with 200 µl Dynabeads M-280 Streptavidin (Invitrogen, Carlsbad, CA, USA) for depletion of non-specific bound phage particles, then the treated phages were incubated with another 200 µDynabeads saturated with 20 µg biotinylated PD-1 ECD proteins at RT for 1 h with gentle mixing. After intensive washing, the phage that bound to beads were eluted as described above.

5. VIM Protein Expression and Screening

After desired panning steps, phage infected TG1 cell colonies grown on the plates were scraped and pFL249 phagemid containing VHH fragments were extracted. The VHH fragments were cloned by digestion of pFL249 plasmids with Sfi I and Not I and then ligated into expression vector pETbac containing genes of hexa-histidine- and c-Myc-tag. The ligation products were transformed into E. coli BL21 (DE3) competent cells and then cultured in ZYM-5052 medium at 25° C. for 48 h with shaking at 230 rpm. Then the bacterial culture supernatants were collected for ELISA or FACS tests.

ELISA was used as the first screening method to test the binding of VHH to human PD-1 ECD protein. Briefly, 96-well plates (Nunc, Rochester, MN, USA) were coated with recombinant his tagged human and mouse PD-1 ECD protein overnight at 4° C. After blocking and washing, the BL21 E. coli supernatants were transferred to the coated plates and incubated at room temperature for 1 h. The plates were then washed and subsequently incubated with secondary antibody Goat Anti-c-Myc-HRP (Bethyl, Montgomery, TX, USA) for 1 h. After washing, TMB substrate was added and the reaction was stopped by 2M HCl. The absorbance at 450 nm was read using a microplate reader (Molecular Device, Sunnyvale, CA, USA).

In order to confirm the native binding of anti-PD-1 VHH on conformational PD-1 molecules expressed on cell membrane, flow cytometry analysis was performed with human PD-1 transfected CHO-S cells and mouse PD-1 transfected 293F cells. The parental CHO-S or 293F cell line were used as negative control. The cells were firstly incubated with the E. coli culture supernatant samples in 96-well U-bottom plates (BD, Franklin Lakes, NJ, USA) at a density of $1\times10^5$ cells/well at 4° C. for 1 h, then with a secondary antibody Goat Anti-c-Myc-PE (Bethyl, Montgomery, TX, USA) at 4° C. for 30 min. 2 times of washings were applied between each steps and the cells were resuspended in 1×PBS/1% BSA for flow cytometery analysis (IntelliCyt, Albuquerque, NM, USA).

6. Sequencing

The positive E. coli clones selected by ELISA and FACS screening were sent to Biosune (Shanghai, China) for nucleotide sequencing of VHH gene. The sequencing results were analyzed using CLC Main Workbench (Qiagen, Hilden, Germany).

One lead antibody was VHH named "AP17R1-2H2". The sequence information thereof is provided in Table A and the sequence listing. This antibody also served as the "parent" for optimization (including humanization and affinity maturation). The humanization and affinity maturation will be described in more details in Example 3 below.

7. VIM Production

The BL21 E. coli clones harboring VHH gene were cultured in 40 ml of ZYM-5052 medium at 25° C. for 48 h with shaking at 230 rpm. The expression of his- and c-Myc-tag fused VHH protein in BL21 supernatant was confirmed by SDS-PAGE, and then purified using Ni-NTA column. The purity of VHH was determined by SEC-HPLC. For low supernatant expression clones, ultrasonic (Scientz, Ningbo, China) breaking E. coli cells was used to release soluble VHH proteins.

8. Chimeric (hIgG4) Protein Production

The clones of interest were converted to VHH-Fc (hIgG4) fusion antibodies. Briefly, the VHH genes were PCR amplified from the pET-bac vectors using VHH-specific cloning primers containing appropriate restriction sites then cloned by fusion into a modified expression pcDNA3.3 vector containing Fc of human hIgG4. S228P to create corresponding clones of VHH-Fc (hIgG4. SP) chimeric antibody. 293F or Expi293 cells were transiently transfected with the vector for antibody expression. The cell culture supernatants containing antibodies were harvested and purified using Protein A chromatography.

EXAMPLE 3

Antibody Optimization

1. Humanization

VHHs with high affinity and specificity to PD-1 were selected for humanization. "Best Fit" approach was used to humanize VHH chains.

Amino acid sequences of VHH framework regions were blasted against human germline V-gene database, and humanized VHH sequences were generated by replacing human CDR sequences in the top hit with VHH CDR sequences using Kabat CDR definition. Certain residues in the framework region were back-mutated to VHH in order to maintain the affinity. Humanized genes were back-translated, codon optimized for mammalian expression, and synthesized by GENEWIZ. These genes were re-amplified with cloning primers containing appropriate restriction sites and cloned into a modified pcDNA3.3 vector to express humanized VHH-Fc (hIgG4.SP). After testing on PD-1 binding using SPR, the variants with proper affinity were selected as humanized antibody leads. The VHH-Fc (hIgG4) form for the parental antibody "AP17R1-2H2" is named as "AP17R1-2H2-Fc(IgG4)" or "W3056-AP17R1-2H2-FC (IgG4. SP)."

2. Affinity Maturation

Each amino acid of three complementary-determining regions (CDR1, CDR2, and CDR3) of parental clone was individually mutated to other 20 amino acids using a site-directed mutagenesis method. DNA primers containing a NNS codon encoding twenty amino acids were used to introduce mutation to each targeted CDR position. The individual degenerate primers of phosphorylated were used in site-directed mutagenesis reactions. 200 ng of the reaction products was electroporated into BL21 and expressed.

The mutant clones were screened by using competitive ELISA assay. Briefly, 96-well Maxisorp Immunopla was coated with 0.5 ug/ml anti-c-Myc antibody in coating buffer (200 mM Na2CO3/NaHCO3) at pH 9.2 overnight at 4° C. The next day, the plate was blocked with Casein for 1 h at room temperature. After blocking, *E. coli* supernatants of above mutant clones and parental VHH (i.e., AP17R1-2H2) clone were added to the plate and incubated at room temperature for 1 h. After washing the plate, the pre-mixture of hPro1.hFc-biotin (0.25 ug/ml) and AP17R1-2H2-FC (IgG4.sp) (0.25 ug/ml) were added to the well and incubated for 1 h at room temperature. This was followed by incubation with Streptavidin-HRP conjugate for 1 h at room temperature. HRP activity was detected with TMB substrate and the reaction was stopped with 2 M HCl. Plates were read at 450 nm. The clones exhibiting an optical density (OD) signal at 450 nm greater than 1.5-fold of that of the parental VHH (i.e., AP17R1-2H2) clone were picked and sequenced. These mutant clones were re-expressed in BL21 and purified. Surface plasmon resonance (SPR) was used for detecting the affinity of the mutants. Upon humanization and affinity maturation, a series of variants were obtained.

3. $K_D$ Ranking by SPR

To screen WBP3056 VHH antibodies from affinity maturation, koff to hPro1.ECD.hFc, mPro1.ECD.hFc and cynoPro1.ECD.hFc (AcrobioSystems) was detected by SPR assay using Biacore 8K. hPro1.ECD.hFc, mPro1.ECD.hFc or cynoPro1.ECD.hFc (AcrobioSystems) was captured on an anti-human IgG Fc antibody immobilized CMS sensor chip. Each VHH antibody was injected over the sensor chip at a flow rate of 30 uL/min for an association phase of 120 s, followed by 150 s dissociation. The association and dissociation curve was fit to a 1:1 model using Langmuir analysis. The results are shown in Table 3.

EXAMPLE 4

In Vitro Characterization Binding to Human, Mouse, and Cynomolgus Monkey PD-1 as Measured by FACS 1.1 Human PD-1 Binding The cells CHO-S.hPro1.C6 ($2 \times 10^5$ cells/well) were incubated with various concentrations of anti-PD-1 antibodies (4-fold serially diluted from 133.3 nM to 0.008 nM) at 4° C. for 1 hour. After washing with 1×PBS/1% BSA, the secondary antibody PE-labeled goat anti-human IgG was applied and incubated with cells at 4° C. for 1 hour. Anti-human PD-1 antibodies BMK1 and BMK3 were used as positive control. Human IgG4 isotype antibody was used as negative control. The cells were then washed and resuspended in 1×PBS/1% BSA. MFI of the cells was measured by a flow cytometer (BD) and analyzed by FlowJo (version 7.6.1). Data were shown in FIG. 1 and Table 4.

TABLE 4

| Binding $EC_{50}$ of to human PD-1 by FACS | |
|---|---|
| Antibody | $EC_{50}$ (nM) |
| W3056-AP17R1-2H2-FC(IgG4.SP) | 1.872 |
| W3056-AP17R1-2H2-Z1-R1-14A1-FC(IgG4.SP) | 0.612 |
| WBP305-BMK1.hIgG4 | 0.409-0.749 |
| WBP305-BMK3.hIgG4 | 3.103 |

Figure 1:
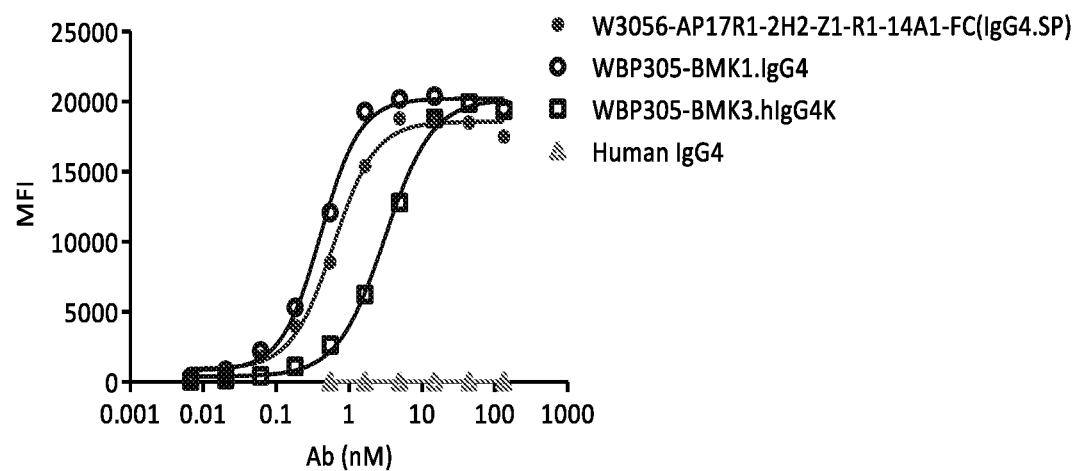
FIG. 1 shows the binding of anti-PD-1 antibodies to cell surface human PD-1, expressed by MFI (Median Fluorescence Intensity) and measured by FACS. Panel A shows data for antibody W3056-AP17R1-2H2-Z1-R1-14A1-FC (IgG4.SP). Panel B shows data for antibody AP17R1-2H2-FC(IgG4).
Figure 1:
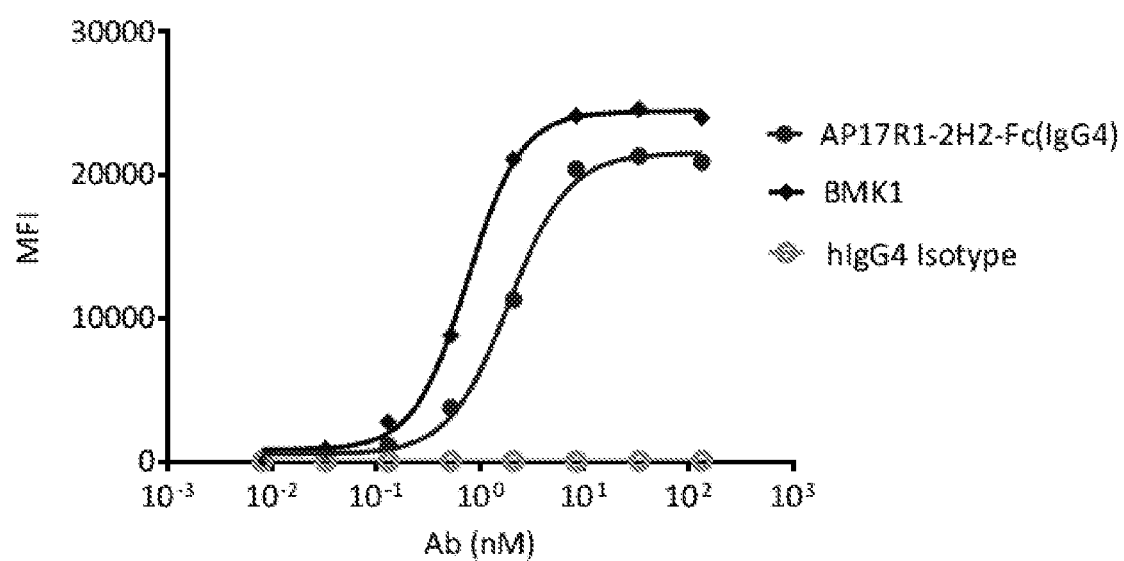

As shown in FIG. 1 and Table 4, W3056 antibodies including the antibody W3056-AP17R1-2H2-Z1-R1-14A1-FC(IgG4. SP) and the antibody AP17R1-2H2-FC(IgG4) effectively bound to cell surface human PD-1 in a dose-dependent manner.

1.2 Mouse PD-1 Binding

The cells 293F.mPro1.B4 ($2 \times 10^5$ cells/well) were incubated with various concentrations of anti-PD-1 antibodies (3-fold serially diluted from 133.3 nM to 0.008 nM) at 4° C.

TABLE 3

| | hPro1.ECD.hFc | | | mPro1.ECD.hFc | | | cynoPro1.ECD.hFc | | |
|---|---|---|---|---|---|---|---|---|---|
| Analyte (VHH protein) | ka (1/Ms) | kd (1/s) | KD (M) | ka (1/Ms) | kd (1/s) | KD (M) | ka (1/Ms) | kd (1/s) | KD (M) |
| AP17R1-2H2-Z1-R1-4B2 | $4.50 \times 10^5$ | $4.13 \times 10^{-3}$ | $9.19 \times 10^{-9}$ | $2.92 \times 10^5$ | $1.01 \times 10^{-2}$ | $3.46 \times 10^{-8}$ | $3.45 \times 10^5$ | $8.79 \times 10^{-3}$ | $2.55 \times 10^{-8}$ |
| AP17R1-2H2-Z1-R1-4D8 | $4.17 \times 10^5$ | $3.96 \times 10^{-3}$ | $9.49 \times 10^{-9}$ | $2.84 \times 10^5$ | $9.55 \times 10^{-3}$ | $3.37 \times 10^{-8}$ | $3.20 \times 10^5$ | $8.33 \times 10^{-3}$ | $2.60 \times 10^{-8}$ |
| AP17R1-2H2-Z1-R1-6E1 | $4.39 \times 10^5$ | $3.28 \times 10^{-3}$ | $7.48 \times 10^{-9}$ | $2.87 \times 10^5$ | $1.46 \times 10^{-2}$ | $5.08 \times 10^{-8}$ | $3.41 \times 10^5$ | $7.54 \times 10^{-3}$ | $2.21 \times 10^{-8}$ |
| AP17R1-2H2-Z1-R1-14A1 | $5.43 \times 10^5$ | $1.12 \times 10^{-3}$ | $2.06 \times 10^{-9}$ | $3.81 \times 10^5$ | $4.70 \times 10^{-3}$ | $1.23 \times 10^{-8}$ | $4.24 \times 10^5$ | $2.13 \times 10^{-3}$ | $5.04 \times 10^{-9}$ |
| AP17R1-2H2-Z1-R1-14F1 | $4.11 \times 10^5$ | $1.35 \times 10^{-3}$ | $3.28 \times 10^{-9}$ | $2.80 \times 10^5$ | $2.18 \times 10^{-3}$ | $7.80 \times 10^{-9}$ | $3.09 \times 10^5$ | $2.77 \times 10^{-3}$ | $8.98 \times 10^{-9}$ |
| AP17R1-2H2-Z1-R1-14B3 | $4.89 \times 10^5$ | $2.49 \times 10^{-3}$ | $5.09 \times 10^{-9}$ | $3.44 \times 10^5$ | $5.96 \times 10^{-3}$ | $1.73 \times 10^{-8}$ | $3.66 \times 10^5$ | $4.84 \times 10^{-3}$ | $1.32 \times 10^{-8}$ |
| AP17R1-2H2-Z1-R1-14F3 | $4.65 \times 10^5$ | $1.09 \times 10^{-3}$ | $2.35 \times 10^{-9}$ | $2.70 \times 10^5$ | $7.32 \times 10^{-3}$ | $2.71 \times 10^{-8}$ | $3.44 \times 10^5$ | $2.47 \times 10^{-3}$ | $7.18 \times 10^{-9}$ |
| AP17R1-2H2-Z1-R1-27A2 | $3.87 \times 10^5$ | $3.31 \times 10^{-3}$ | $8.56 \times 10^{-9}$ | $2.65 \times 10^5$ | $8.94 \times 10^{-3}$ | $3.37 \times 10^{-8}$ | $3.02 \times 10^5$ | $7.45 \times 10^{-3}$ | $2.46 \times 10^{-8}$ |
| AP17R1-2H2-Z1-R1-29B2 | $4.06 \times 10^5$ | $3.47 \times 10^{-3}$ | $8.54 \times 10^{-9}$ | $2.64 \times 10^5$ | $1.48 \times 10^{-2}$ | $5.58 \times 10^{-8}$ | $3.18 \times 10^5$ | $8.17 \times 10^{-3}$ | $2.57 \times 10^{-8}$ |
| AP17R1-2H2-Z1-R1-29B6 | $4.25 \times 10^5$ | $2.98 \times 10^{-3}$ | $7.01 \times 10^{-9}$ | $2.77 \times 10^5$ | $1.08 \times 10^{-2}$ | $3.91 \times 10^{-8}$ | $3.23 \times 10^5$ | $6.46 \times 10^{-3}$ | $2.00 \times 10^{-8}$ |
| AP17R1-2H2-Z1-R1-30D3 | $4.16 \times 10^5$ | $2.82 \times 10^{-3}$ | $6.79 \times 10^{-9}$ | $2.77 \times 10^5$ | $1.18 \times 10^{-2}$ | $4.25 \times 10^{-8}$ | $3.25 \times 10^5$ | $6.24 \times 10^{-3}$ | $1.92 \times 10^{-8}$ |
| AP17R1-2H2-Z1 | $3.07 \times 10^5$ | $3.92 \times 10^{-3}$ | $1.27 \times 10^{-8}$ | $2.05 \times 10^5$ | $1.36 \times 10^{-2}$ | $6.62 \times 10^{-8}$ | $2.37 \times 10^5$ | $8.63 \times 10^{-3}$ | $3.64 \times 10^{-8}$ |

In Table 3, it is demonstrated that, after affinity maturation, the affinity maturated VHHs bind to hPro1.ECD.hFc, mPro1.ECD.hFc, and cynoPro1.ECD.hFc, respectively, with better affinities than that before affinity maturation (e.g. AP17R1-2H2-z1, the humanized AP17R1-2H2).

Sequence information on the VHH proteins listed in Table 3 are provided in above Table A and the accompanying sequence listing.

for 1 hour. After washing with 1×PBS/1% BSA, the secondary antibody PE-labeled goat anti-human IgG was applied and incubated with cells at 4° C. for 1 hour. Human IgG4 isotype antibody was used as negative control. The cells were then washed and re-suspended in 1×PBS/1% BSA. MFI of the cells was measured by a flow cytometer and analyzed by FlowJo (version 7.6.1). Data were shown in FIG. 2 and Table 5.

TABLE 5

Binding EC50 to mouse PD-1 by FACS

| Antibody | $EC_{50}$ (nM) |
|---|---|
| W3056-AP17R1-2H2-FC (IgG4.SP) | 4.77 |
| W3056-AP17R1-2H2-Z1-R1-14A1-FC(IgG4.SP) | 4.257 |
| WBP305-BMK1.hIgG4 | NA |
| WBP305-BMK3.hIgG4 | NA |

Figure 2:
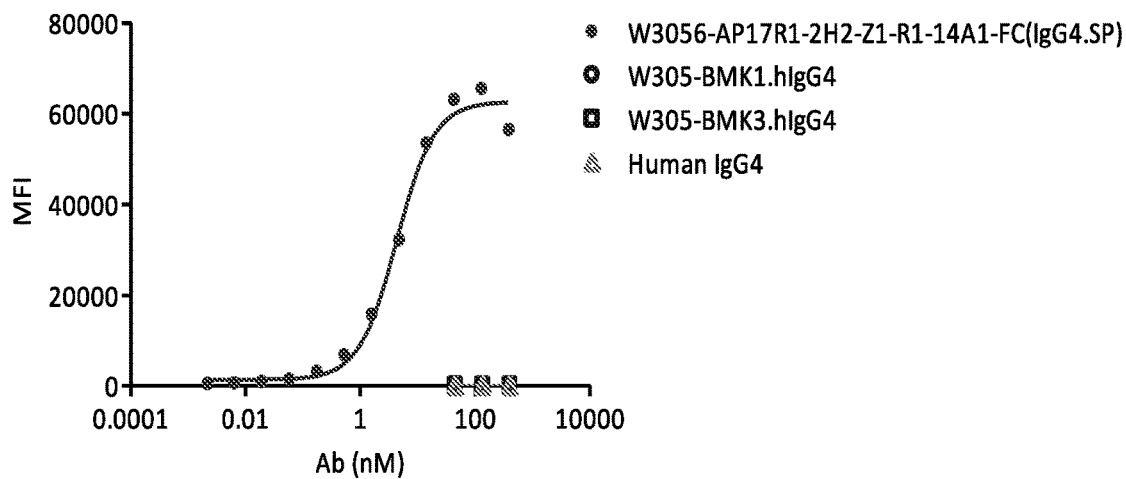
FIG. 2 shows the binding of anti-PD-1 antibodies to cell surface mouse PD-1, expressed by MFI and measured by FACS. Panel A shows data for antibody W3056-AP17R1-2H2-Z1-R1-14A1-FC(IgG4.SP). Panel B shows data for antibody AP17R1-2H2-FC(IgG4).
Figure 2:
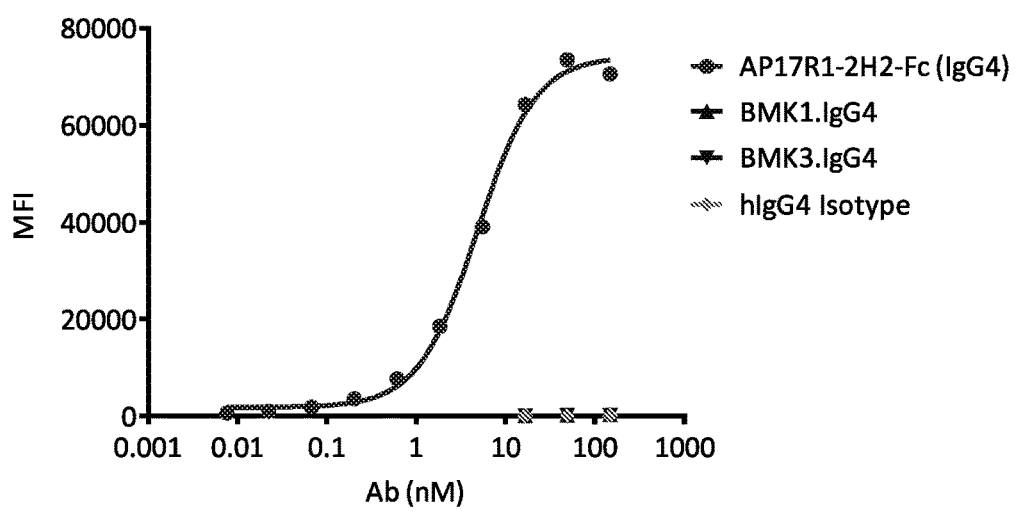

As shown in FIG. 2 and Table 5, W3056 antibodies including the antibody W3056-AP17R1-2H2-Z1-R1-14A1-FC(IgG4.SP) and the antibody AP17R1-2H2-FC(IgG4) effectively bound to cell surface mouse PD-1 in a dose-dependent manner.

1.3 Cynomolgus Monkey PD-1 Binding

Cynomolgus monkey PD-1 (GenBank Accession No. NP_001271065.1) transient transfected 293F cells ($2\times10^5$ cells/well) were incubated with various concentrations of anti-PD-1 antibodies (3-fold serially diluted from 133.4 nM to 0.008 nM) at 4° C. for 1 hour. After washing with 1×PBS/1% BSA, the secondary antibody PE-labeled goat anti-human IgG was applied and incubated with cells at 4° C. for 1 hour. Anti-human PD-1 antibodies BMK1 and BMK3 were used as positive control. Human IgG4 isotype antibody was used as negative control. The cells were then washed and re-suspended in 1×PBS/1% BSA. MFI of the cells was measured by a flow cytometer and analyzed by FlowJo (version 7.6.1). Data were shown in FIG. 3 and Table 6.

TABLE 6

Binding EC50 to cyno PD-1 by FACS in two separated experiments

| Antibody | $EC_{50}$ (nM) (experiment 1) | $EC_{50}$ (nM) (experiment 2) |
|---|---|---|
| W3056-AP17R1-2H2-FC (IgGASP) | 0.98 | / |
| W3056-AP17R1-2H2-Z1-R1-14A1-FC(IgG4.SP) | / | 1.975 |
| W305-BMK1.hIgG4 | 0.55 | 1.981 |
| W305-BMK3.hIgG4 | 1.03 | 2.293 |

Figure 3:
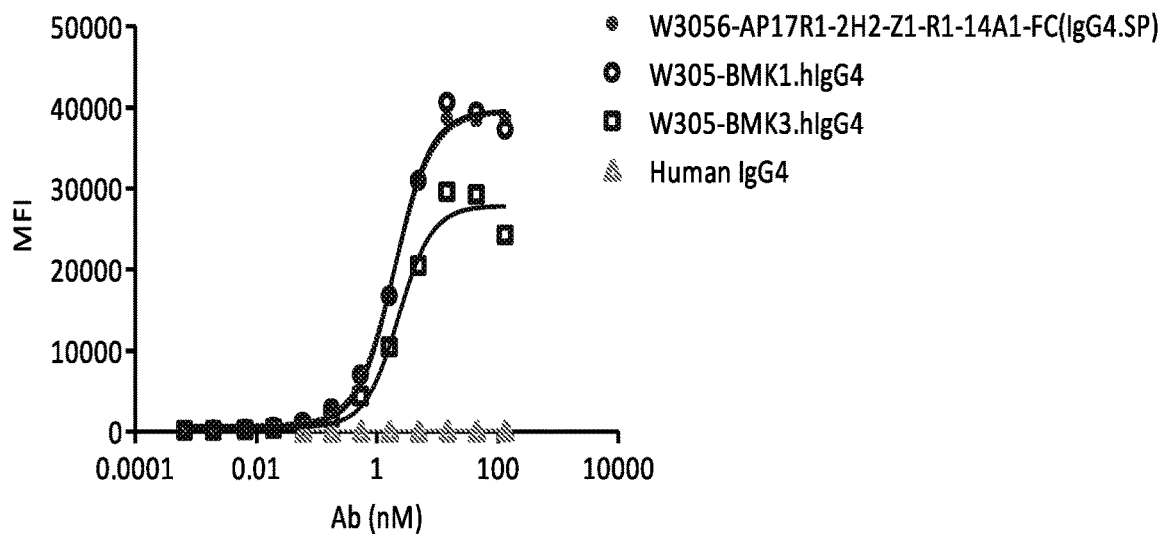
FIG. 3 shows the binding of anti-PD-1 antibodies to cell surface cynomolgus PD-1, expressed by MFI and measured by FACS. Panel A shows data for antibody W3056-AP17R1-2H2-Z1-R1-14A1-FC(IgG4.SP). Panel B shows data for antibody AP17R1-2H2-FC(IgG4).
Figure 3:
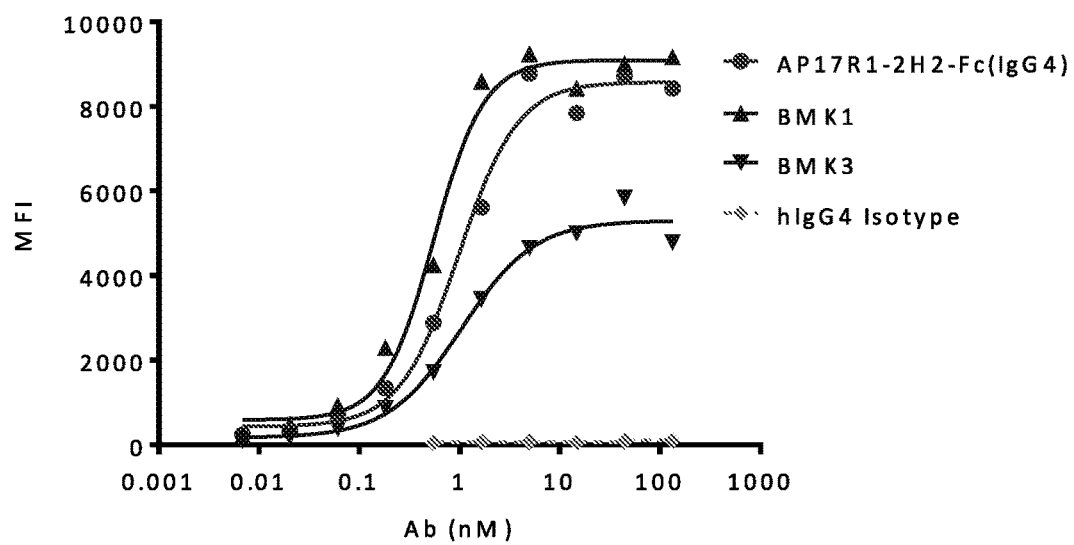

As shown in FIG. 3 and Table 6, W3056 antibodies including the antibody W3056-AP17R1-2H2-Z1-R1-14A1-FC(IgG4.SP) and the antibody AP17R1-2H2-FC(IgG4) effectively bound to cell surface cynomolgus PD-1 in a dose-dependent manner.

2. Blocking of PD-L1 or PD-L2 Binding to PD1

2.1 Human PD-1/PD-L1 Blocking as Measured by FACS

The human PD-1 transfected CHO-S.hPro1.C6 cells were transferred into 96-well U-bottom plates at a density of $2\times10^5$ cells/well. Various concentrations of antibodies (4-fold serially diluted from 133.3 nM to 0.008 nM) and constant concentration of mouse Fc tagged PD-L1 ECD protein (hProL1.ECD.mFc) (5 μg/mL) were pre-mixed and incubated with cells at 4° C. for 1 hour. After washing with 1×PBS/1% BSA, the secondary antibody PE-labeled goat anti-mouse IgG was applied and incubated with cells at 4° C. for 1 hour. The cells were then washed and resuspended in 1×PBS/1% BSA. MFI of the cells was measured by a flow cytometer and analyzed by FlowJo (version 7.6.1). Data were shown in FIG. 4 and Table 7.

TABLE 7

Blocking human PD-L1 binding to cell surface human PD-1

| Antibody | IC50 (nM) |
|---|---|
| W3056-AP17R1-2H2-Fc (IgG4.SP) | 1.000 |
| W3056-AP17R1-2H2-Z1-R1-14A1-FC(IgG4.SP) | 0.655 |
| WBP305-BMK1.hIgG4 | 0.544 |
| WBP305-BMK3.hIgG4K | 1.763 |

Figure 4:
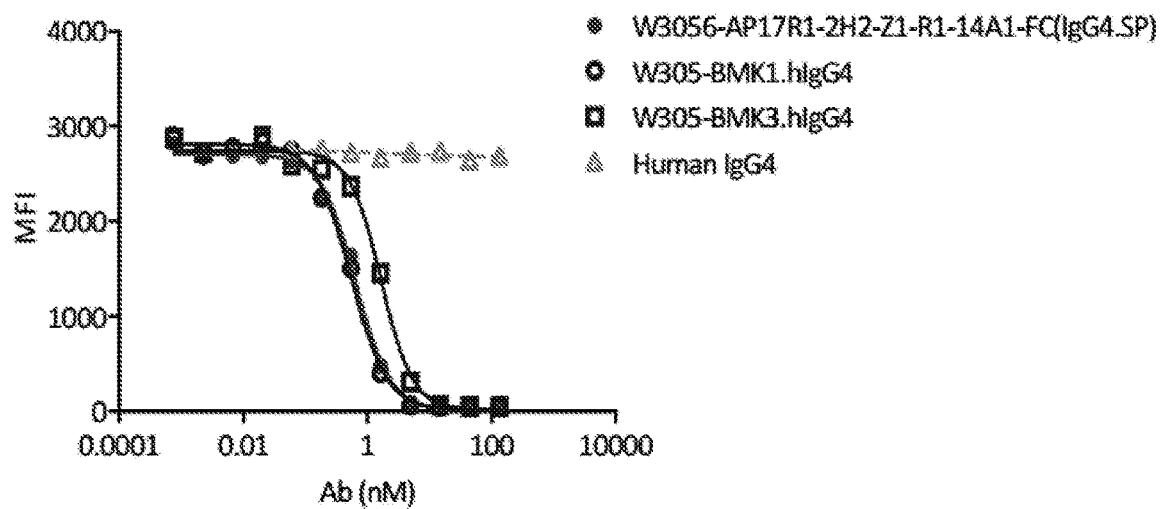
FIG. 4 shows the human PD1/PD-L1 blocking as measured by FACS. Panel A shows data for antibody W3056-AP17R1-2H2-Z1-R1-14A1-FC(IgG4.SP). Panel B shows data for antibody AP17R1-2H2-FC(IgG4).
Figure 4:
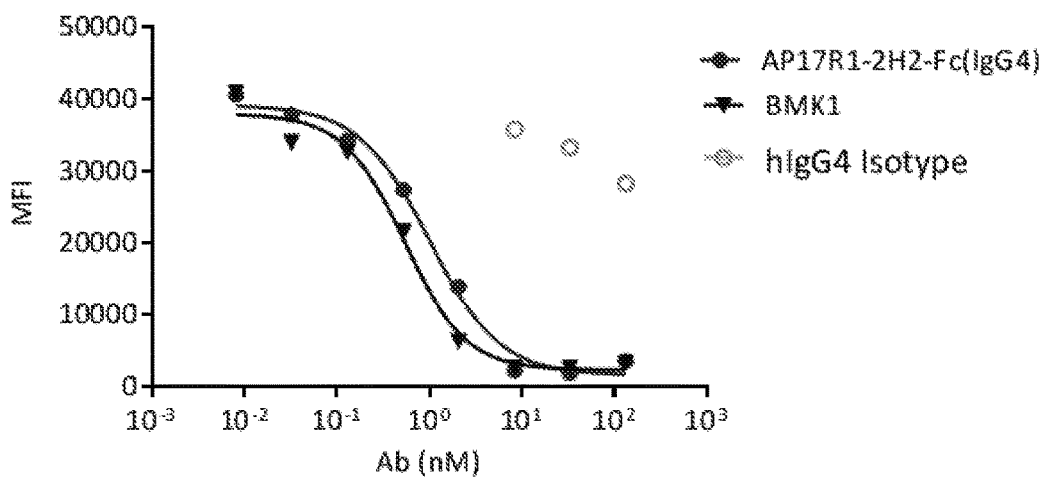

As shown in FIG. 4 and Table 7, W3056 antibodies including the antibody W3056-AP17R1-2H2-Z1-R1-14A1-FC(IgG4. SP) and the antibody AP17R1-2H2-FC(IgG4) are effective at blocking the binding of human PD-L1 to cell surface human PD-1 in a dose-dependent manner.

2.2. Mouse PD-1/PD-L1 Blocking as Measured by FACS

The mouse PD-1 transfected 293F.mPro1.B4 cells were transferred into 96-well U-bottom plates at a density of $2\times10^5$ cells/well. Various concentrations of anti-PD-1 antibodies (3-fold serially diluted from 1334 nM to 0.07 nM) and constant concentration of mouse Fc tagged mouse PD-L1 ECD protein (mProL1.ECD.mFc) (5 μg/mL) were pre-mixed and incubated with cells at 4° C. for 1 hour. After washing with 1×PBS/1% BSA, the secondary antibody PE-labeled goat anti-mouse IgG was applied and incubated with cells at 4° C. for 1 hour. The cells were then washed and resuspended in 1×PBS/1% BSA. MFI of the cells was measured by a flow cytometer and analyzed by FlowJo (version 7.6.1). Data were shown in FIG. 5 and Table 8.

TABLE 8

Blocking mouse PD-L1 binding to cell surface mouse PD-1

| Antibody | IC50 (nM) |
|---|---|
| W3056-AP17R1-2H2-FC(IgG4.SP) | 22.09 |
| W3056-AP17R1-2H2-Z1-R1-14A1-FC(IgG4.SP) | 10.19 |
| WBP305-BMK1.hIgG4 | NA |
| WBP305-BMK3.hIgG4K | NA |

Figure 5:
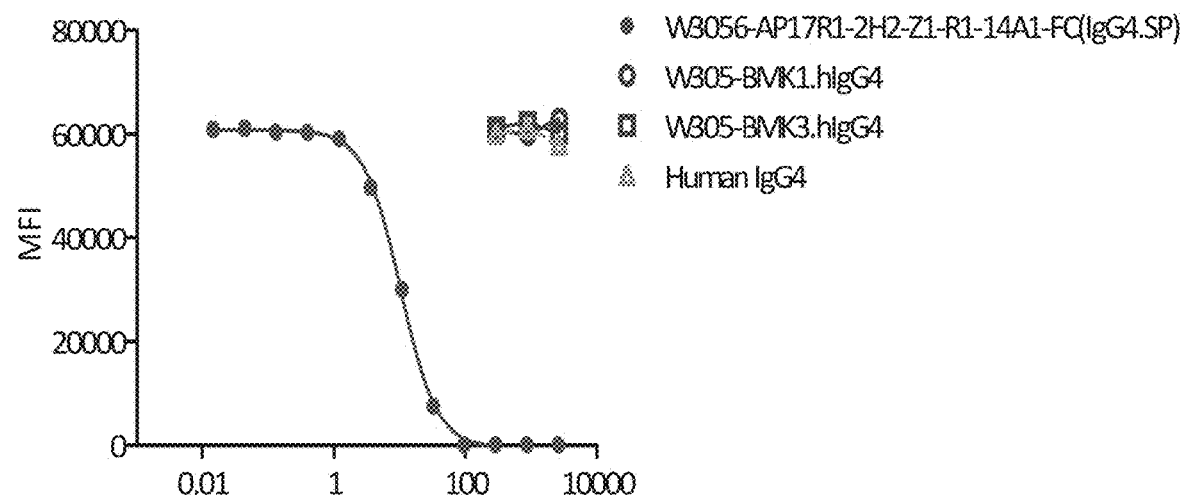
FIG. 5 shows the mouse PD1/PD-L1 blocking as measured by FACS. Panel A shows data for antibody W3056-AP17R1-2H2-Z1-R1-14A1-FC(IgG4.SP). Panel B shows data for antibody AP17R1-2H2-FC(IgG4).
Figure 5:
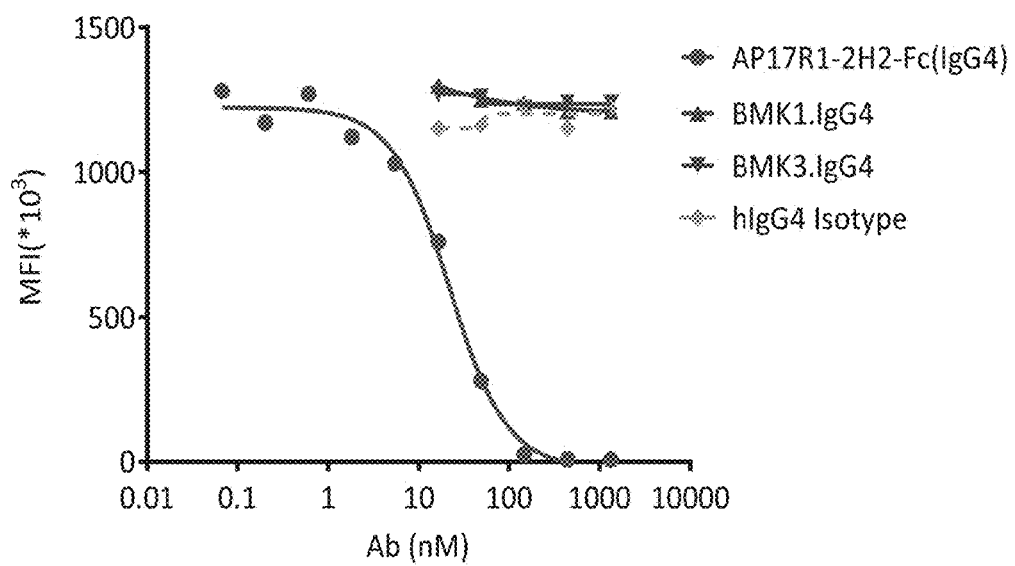

As shown in FIG. 5 and Table 8, W3056 antibodies including the antibody W3056-AP17R1-2H2-Z1-R1-14A1-FC(IgG4. SP) and the antibody AP17R1-2H2-FC(IgG4) are effective at blocking the binding of mouse PD-L1 to cell surface PD-1 in a dose-dependent manner.

2.3 Human PD-1/PD-L2 Blocking as Measured by ELISA

Plates were pre-coated with 1 μg/mL, 100 μL per well of human PD-1 ECD (hPro1.ECD.mFc) at 4° C. overnight. After 1-hour blocking using 200 μL of 1×PBS/2% BSA, constant concentration of his tagged human PD-L2 ECD (hPro1L2.ECD.His) and various concentrations of testing antibodies (3-fold serially diluted from 66.7 nM to 0.003 nM) were pre-mixed and added to the plates. After 2-hour incubation at ambient temperature, the binding of the ligand to the immobilized protein was detected by HRP-labeled goat anti-His antibody. The color was developed by dispensing 100 μL of TMB substrate, and then stopped by 100 μL of 2N HCl. The absorbance was read at 450 nm and 540 nm using a microplate spectrophotometer. Data were shown in FIG. 6 and Table 9.

TABLE 9

Blocking human PD-L2 binding to immobilized human PD-1 in two separated experiments

| Antibody | IC50 (nM) (experiment 1) | IC50 (nM) (experiment 2) |
| --- | --- | --- |
| W3056-AP17R1-2H2-FC(IgG4.SP) | 2.02 | / |
| W3056-AP17R1-2H2-Z1-R1-14A1-FC(IgG4.SP) | / | 0.8856 |
| WBP305-BMK1.hIgG4 | 0.95 | 0.5338 |
| WBP305-BMK3.hIgG4K | 2.19 | 1.499 |

Figure 6:
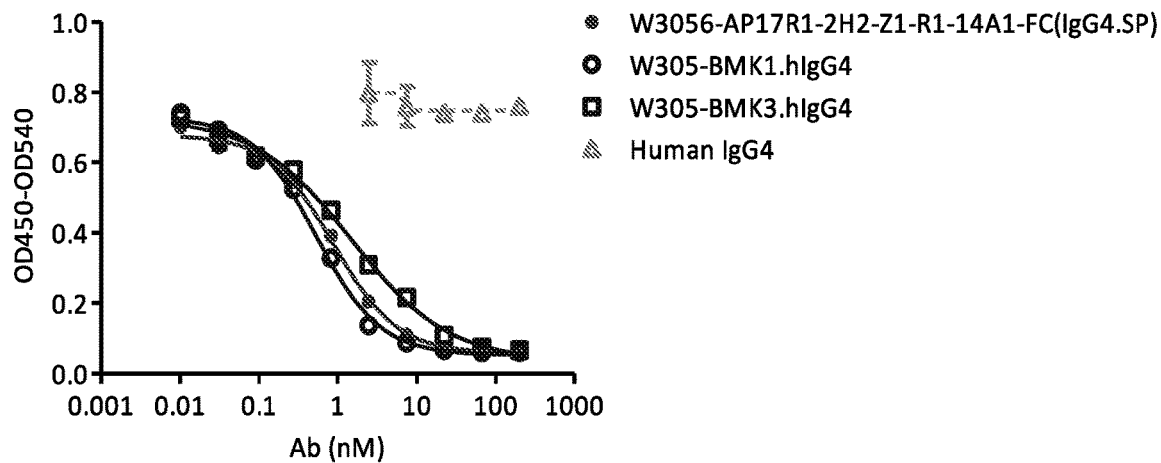
FIG. 6 shows the human PD1/PD-L2 blocking as measured by ELISA. Panel A shows data for antibody W3056-AP17R1-2H2-Z1-R1-14A1-FC(IgG4.SP). Panel B shows data for antibody AP17R1-2H2-FC(IgG4).
Figure 6:
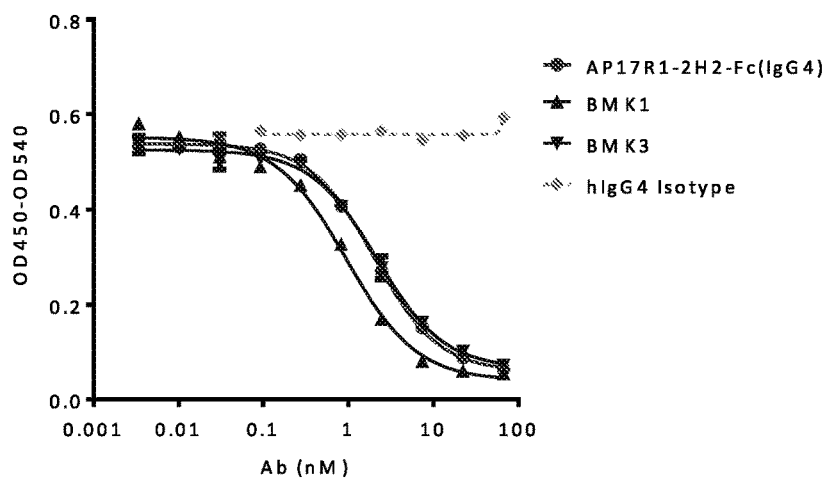

As shown in FIG. 6 and Table 9, W3056 antibodies including the antibody W3056-AP17R1-2H2-Z1-R1-14A1-FC(IgG4. SP) and the antibody AP17R1-2H2-FC(IgG4) are effective at blocking the binding of human PD-L2 to immobilized PD-1 in a dose-dependent manner.

2.4 Cynomolgus Monkey PD-1/PD-L1 Blocking as Measured by ELISA

Plates were pre-coated with 1 µg/mL, 100 µL per well of cyno PD-1 ECD protein (cynoPro1.ECD.hFc) at 4° C. overnight. After 1-hour blocking using 200 µL of 1×PBS/2% BSA, constant concentration of biotinylated cyno PD-L1 (cynoProL1.ECD.hFc.biotin) (2.5 µg/mL) and various concentrations of testing antibody, positive and negative control (3-fold serially diluted from 133.4 nM to 0.007 nM) were pre-mixed and added to the plates. The plates were incubated at ambient temperature for 1 hour. The binding of ligand to the immobilized protein was detected by streptavidin-HRP. The color was developed by dispensing 100 µL of TMB substrate, and then stopped by 100 µL of 2M HCl. The absorbance was read at 450 nm and 540 nm using a microplate spectrophotometer. Data were shown in FIG. 7 and Table 10.

TABLE 10

Blocking cyno PD-L1 binding to immobilized cyno PD-1 in two separated experiments

| Antibody | IC50 (nM) (experiment 1) | IC50 (nM) (experiment 2) |
| --- | --- | --- |
| W3056-AP17R1-2H2-FC(IgG4.SP) | 1.30 | / |
| W3056-AP17R1-2H2-Z1-R1-14A1-FC(IgG4.SP) | / | 0.8534 |
| WBP305-BMK1.hIgG4 | 0.47 | 0.5848 |
| WBP305-BMK3.hIgG4K | 14.21 | 14.59 |

Figure 7:
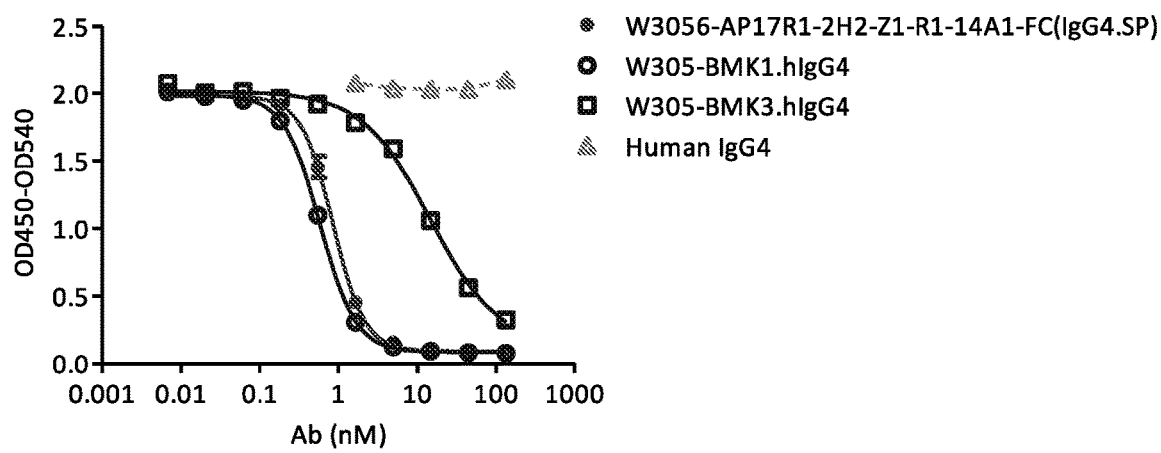
FIG. 7 shows the cynomolgus PD1/PD-L1 blocking as measured by ELISA. Panel A shows data for antibody W3056-AP17R1-2H2-Z1-R1-14A1-FC(IgG4.SP). Panel B shows data for antibody AP17R1-2H2-FC(IgG4).
Figure 7:
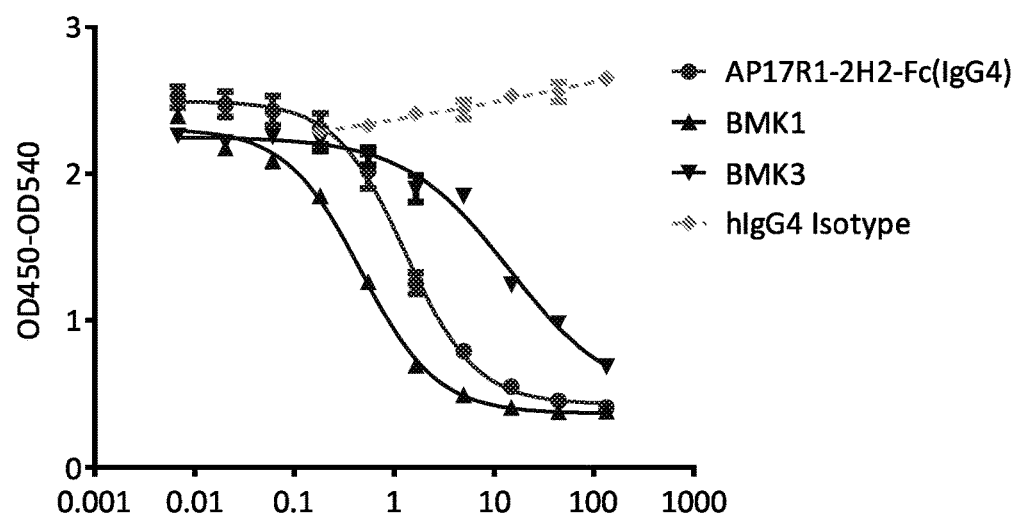

As shown in FIG. 7 and Table 10, W3056 antibodies including the antibody W3056-AP17R1-2H2-Z1-R1-14A1-FC(IgG4. SP) and the antibody AP17R1-2H2-FC(IgG4) are effective at blocking the binding of cyno PD-L1 to immobilized cyno PD-1 in a dose-dependent manner.

3. Cross-Family Protein Binding Assay as Measured by ELISA

Plates were pre-coated with 1 µg/mL, 100 µL per well of hPD-1.ECD.mFc, hCD28.ECD.mFc, hCTLA-4.ECD.His, hICOS.ECD.mFc or hBTLA.ECD.His at 4° C. overnight. After 1-hour blocking using 200 µL of 1×PBS/2% BSA, testing antibodies were added to the plates at a concentration of 100 nM. The plates were incubated at ambient temperature for 1 hour. The binding of the antibodies to the immobilized proteins was detected by HRP-labeled goat anti-human IgG antibody. The color was developed by dispensing 100 µL of TMB substrate, and then stopped by 100 µL of 2N HCl. The absorbance was read at 450 nm and 540 nm using a microplate spectrophotometer. Data were shown in FIG. 8.

Figure 8:
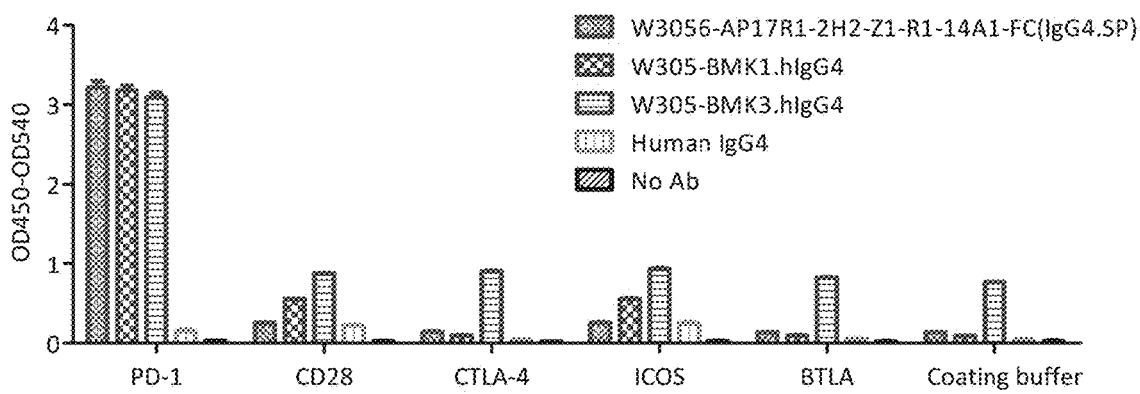
FIG. 8 shows cross-reactivity to human PD-1, CD28, CTLA-4, ICOS and BTLA as measured by ELISA. Panel A shows data for antibody W3056-AP17R1-2H2-Z1-R1-14A1-FC(IgG4.SP). Panel B shows data for antibody AP17R1-2H2-FC(IgG4).
Figure 8:
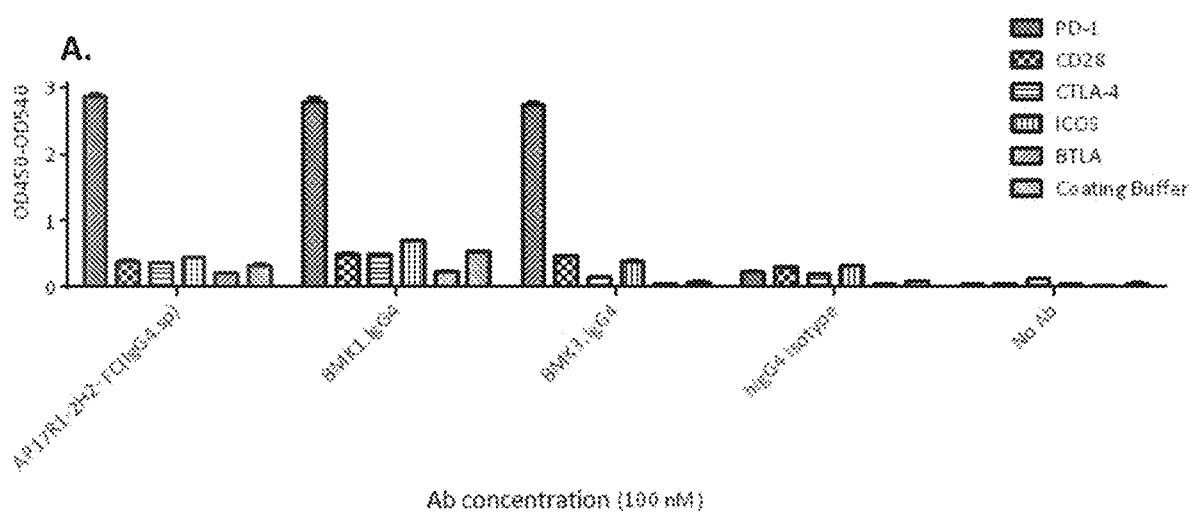

As shown in FIG. 8, W3056 antibodies including the antibody W3056-AP17R1-2H2-Z1-R1-14A1-FC(IgG4.SP) and the antibody AP17R1-2H2-FC(IgG4) specifically bound to immobilized human PD-1 and did not cross-react to human CD28, CTLA-4, ICOS and BTLA.

4. Epitope Binning by FACS

The human PD-1 transfected cells CHO-S.hPro1.C6 were transferred into 96-well U-bottom plates at a density of 1-2×10$^5$ cells/well. Serial dilutions of testing antibodies (4-fold serially diluted from 133.3 nM to 0.008 nM) were mixed with constant concentration of biotinylated BMK1 (1 µg/mL) or biotinylated BMK3 (1 µg/mL), respectively. Then the mixture was added to the cells in 96-well plates and incubated at 4° C. for 1 hour. After washing with 1×PBS/1% BSA, the secondary antibody SA-PE was applied and incubated with cells at 4° C. for 1 hour. The cells were then washed and resuspended in 1×PBS/1% BSA. MFI of the cells was measured by a flow cytometer and analyzed by FlowJo. Data were shown FIG. 9.

Figure 9:
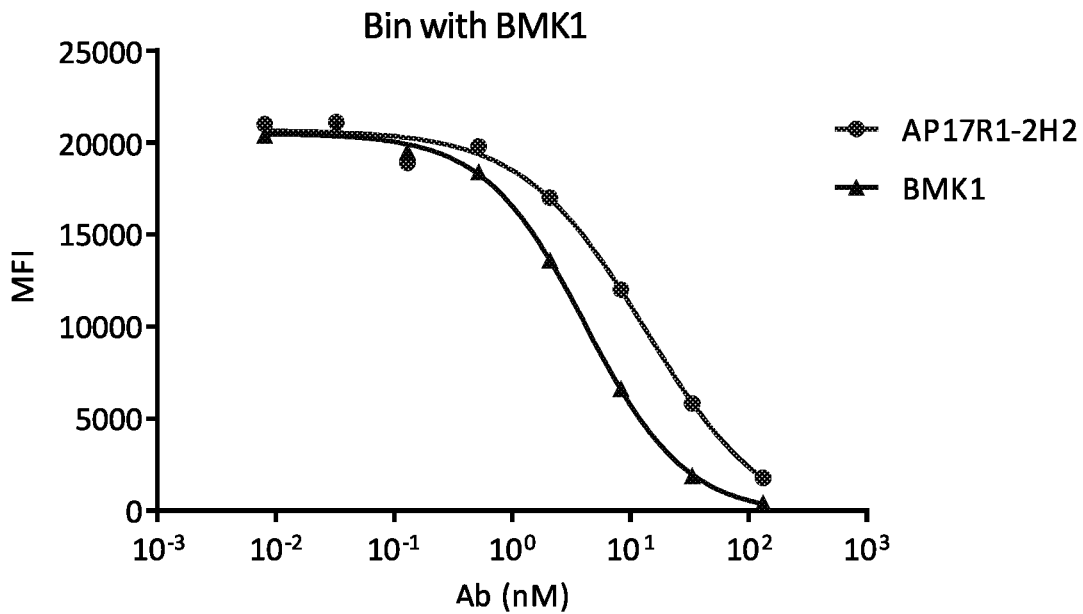
FIG. 9 shows epitope binning of the antibody AP17R1-2H2 (FIGS. 9A and 9B) and the antibody W3056-AP17R1-2H2-Z1-R1-14A1-FC(IgG4. SP) (FIGS. 9C and 9D) against benchmark antibodies BMK1 and BMK3, respectively.
Figure 9:
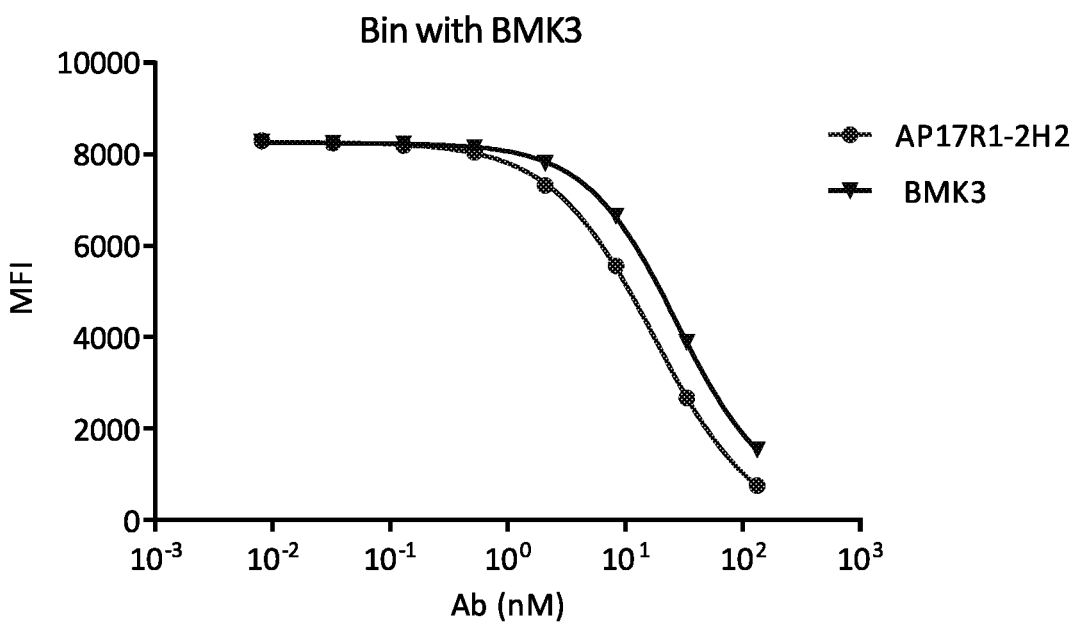
Figure 9:
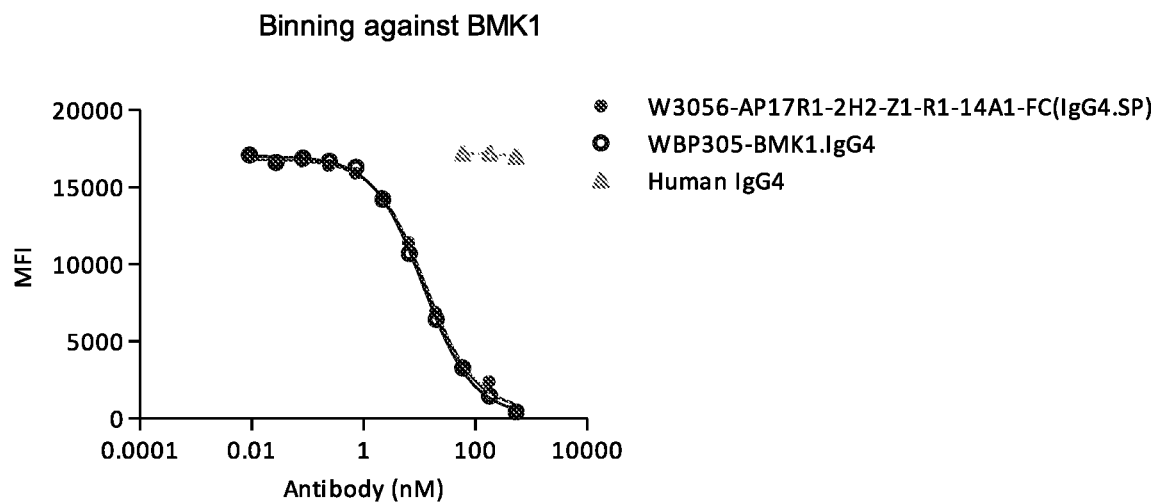
Figure 9:
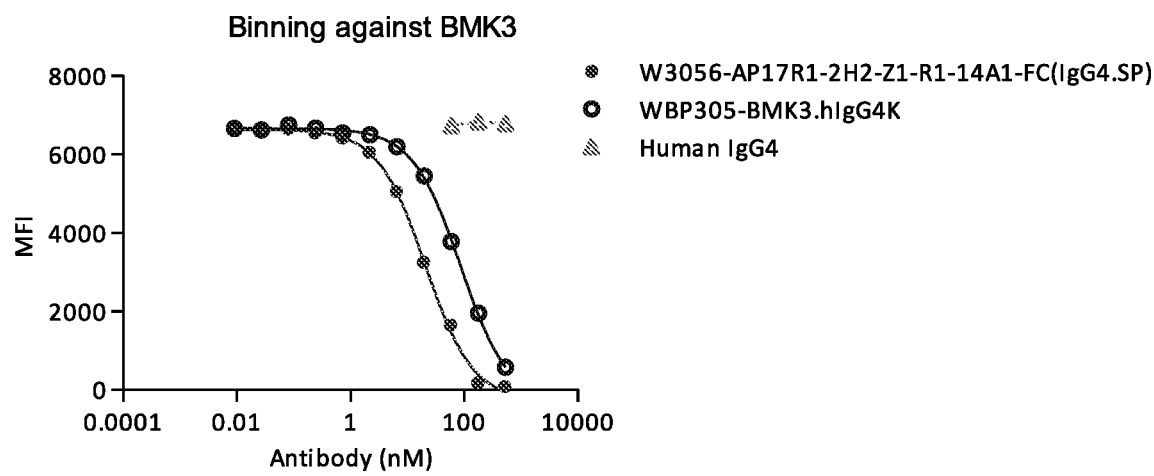

As shown in FIG. 9, W3056 antibodies W3056-AP17R1-2H2-Z1-R1-14A1-FC (IgG4.SP) and AP17R1-2H2 share similar epitope bin with BMK1 and BMK3.

5. Human Cell Based Functional Assays

One-way mixed lymphocyte reaction (one-way MLR) was used to test the agonistic effect of PD-1 antibodies on cytokine secretion of human CD4$^+$ T cells.

i) Cell isolation, cell culture and induction

Human PBMCs were freshly isolated from healthy donors using Ficoll-Paque PLUS gradient centrifugation. Isolated PBMCs were cultured in complete RPMI-1640 (containing 10% FBS and 1% PS) supplemented with 100 U/mL recombinant human IL-2.

Human monocytes were isolated using Human Monocyte Enrichment Kit according to the manufacturer's instructions. Cell concentration was adjusted to 2×10$^6$ cells/mL in complete RPMI-1640 medium supplemented with recombinant human GM-CSF at 800 U/mL and IL-4 at 50 ng/mL. Cell suspension was seeded at 2.5 mL/well in 6-well plate. Cells were cultured for 5 to 7 days to differentiate into dendritic cells (DCs). Cytokines were replenished every 2-3 days by replacing half of the media with fresh media supplemented with cytokines.

Human CD4$^+$ T cells were isolated using Human CD4$^+$ T cell Enrichment kit according to the manufacturer's protocol.

ii) Mixed Lymphocyte Reaction

For human allogeneic MLR, purified CD4$^+$ T cells were co-cultured with allogeneic immature DCs (iDCs). For human autologous MLR, PBMCs were treated with CMV peptide for 5 days before CD4+ T cell isolation. On the day of assay, DCs were treated with CMV peptide for one hour, and then co-cultured with autologous human CD4$^+$ T cells.

MLR was set up in 96-well round bottom plates using complete RPMI-1640 medium. CD4$^+$ T cells, various concentrations of antibodies and allogeneic DCs were added to the plates at an appropriate ratio. The plates were incubated at 37° C., 5% CO$_2$. After incubation for 3-5 days, the cytokine production or cell proliferation was detected.

iii) Cytokine Detection

Human IL-2 and IFN-γ release were measured by ELISA using matched antibody pairs. Recombinant human IL-2 and IFN-γ were used as standards. The serial concentrations of IL-2 was 2 ng/ml, 1 ng/ml, 0.5 ng/ml, 0.25 ng/ml, 0.125 ng/ml, 0.063 ng/ml, 0.031 ng/ml, 0.016 ng/ml, 0.008 ng/ml, and that of IFN-γ was 8 ng/ml, 4 ng/ml, 2 ng/ml, 1 ng/ml, 0.5 ng/ml, 0.25 ng/ml, 0.125 ng/ml, 0.063 ng/ml, 0.031 ng/ml. The plates were pre-coated with capture antibody specific for human IL-2 or IFN-γ, respectively. After blocking, 100 μL of standards or samples were pipetted into each well and incubated for 2 hours at ambient temperature. Following removal of the unbound substances, the biotin-conjugated detecting antibody was added to the wells and incubated for one hour. Streptavidin-HRP was then added to the wells for 30 minutes at ambient temperature. The color was developed by dispensing 100 μL of TMB substrate, and then stopped by 100 μL of 2N HCl. The absorbance was read at 450 nm using a microplate spectrophotometer. The concentration of cytokine in supernatant was calculated from the standard curve.

iv) Proliferation Detection

The number of viable cells in culture were determined by CellTiter-Glo Luminescent Cell Viability Assay according to the manufacture's instruction.

Figure 10:
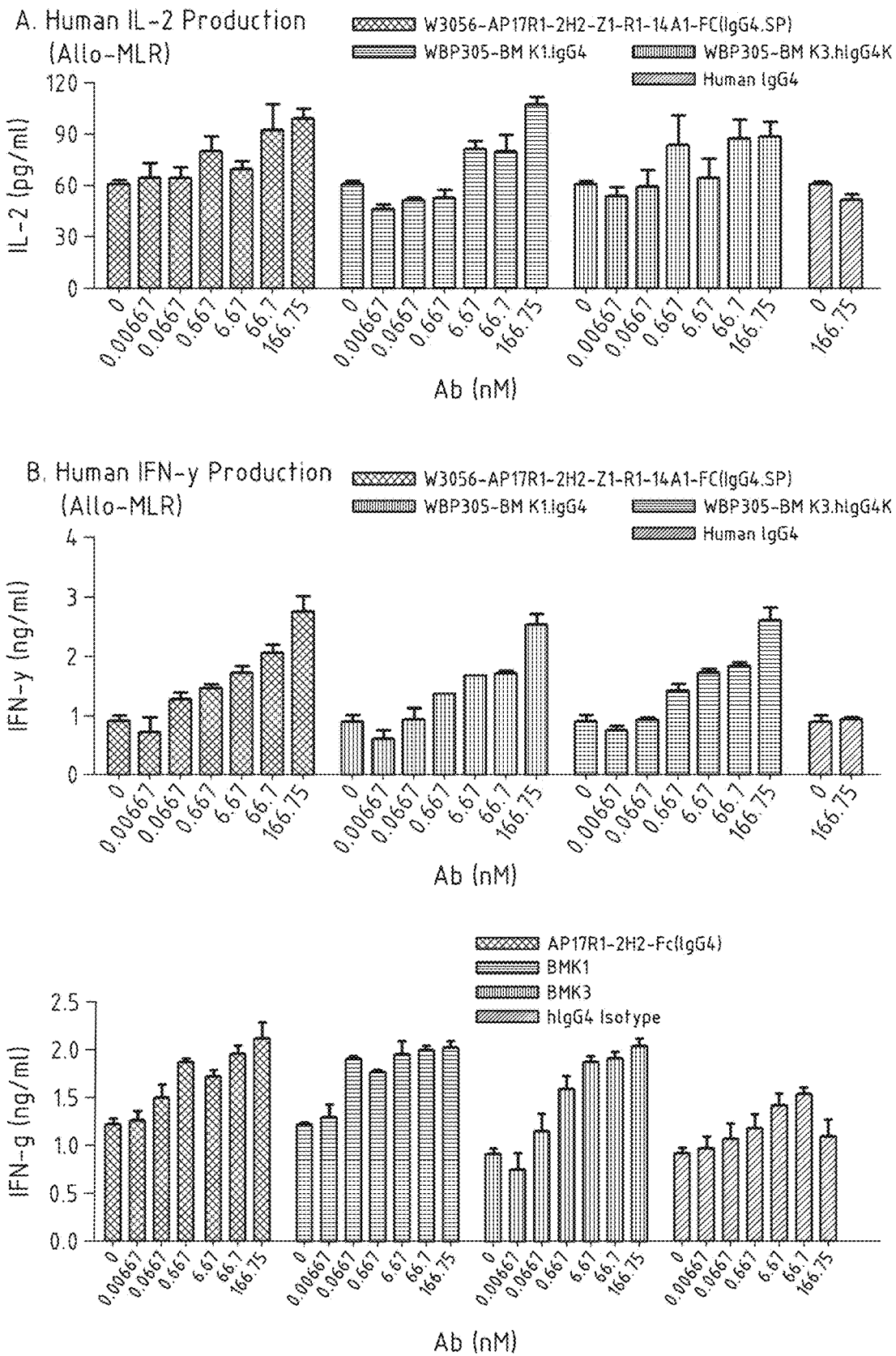
FIG. 10 shows the effects of anti-PD-1 antibodies on human allogeneic mixed lymphocyte reaction (Allo-MLR), as measured by ELISA and reflected by the level of IL-2 (FIG. 10A) and IFN-γ (FIG. 10B).
Figure 11:
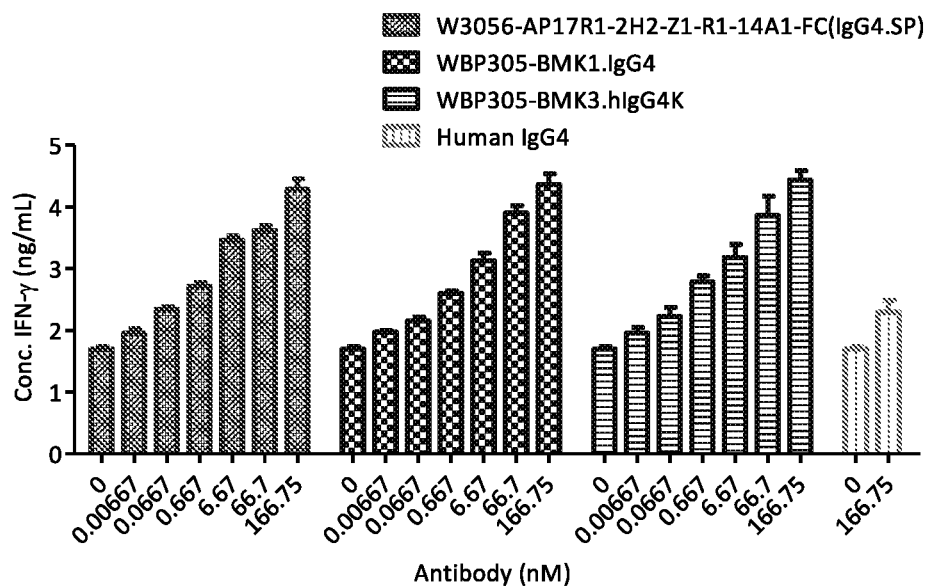
FIG. 11 shows that the effects of anti-PD-1 antibodies on human autologous MLR (Auto-MLR), as reflected by the level of IFN-γ production (FIG. 11A) and T cell proliferation (FIG. 11B).
Figure 11:
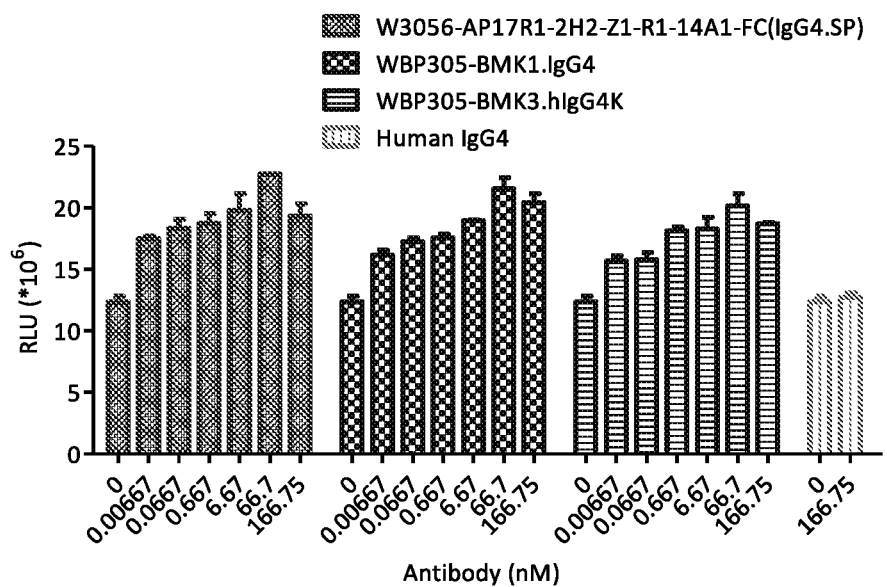

As shown in FIGS. 10A and 10B W3056 antibodies including W3056-AP17R1-2H2-Z1-R1-14A1-FC(IgG4.SP) and AP17R14-2H2-Fc(IgG4) promoted IL-2 and IFN-γ production in a dose-dependent manner in human allo-MLR reaction. FIGS. 11A and 11B show that W3056 antibody AP17R1-2H2-Z1-R1-14A1-FC (IgG4.SP) promoted IFN-γ production and T cell proliferation in auto-MLR reaction.

v) Suppressive Treg Inhibition Assay

Human CD4$^+$ T lymphocytes were enriched from PBMC of one healthy donor, and human monocytes were isolated from another healthy donor. Regulatory T cells (Tregs) were isolated from human CD4$^+$ T cells using Human CD4$^+$ CD25$^{HIGH}$ T Cell Isolation kit, and the remaining T lymphocytes were CD4$^+$CD25$^-$ T cells. DCs were induced from monocyte as described above.

Ten thousand immature DCs, 1×10$^5$ CD4$^+$CD25$^-$ T effector cells, 1×10$^5$ CD4$^+$CD25$^+$ Treg cells and 166.7 nM anti-PD-1 antibodies were incubated in a total volume of 200 μL in 96-well plates. The plates were kept at 37° C. in a 5% CO$_2$ incubator for 5 days. IFN-γ release and T cells proliferation were examined. BMK1 and BMK3 were used as positive control, and human IgG4 isotype antibody was used as negative control. Wells without Treg cells or anti-PD-1 antibody were also included as controls.

Figure 12:
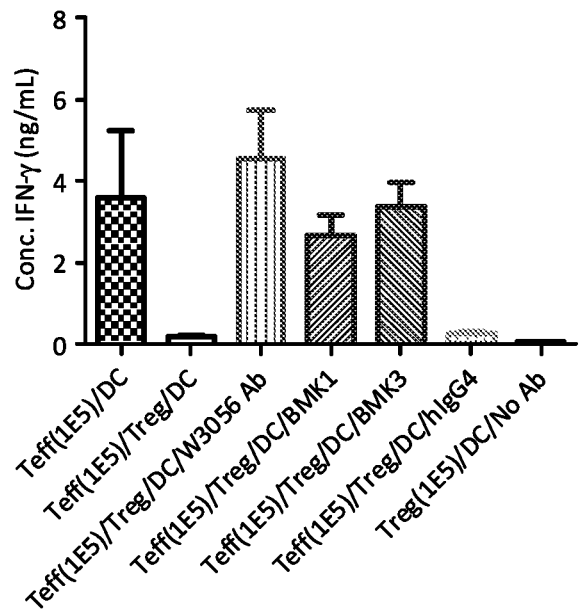
FIG. 12 shows the effects of anti-PD-1 antibodies on human Treg MLR, as reflected by the level of IFN-γ production (FIG. 12A) and T cell proliferation (FIG. 12B).
Figure 12:
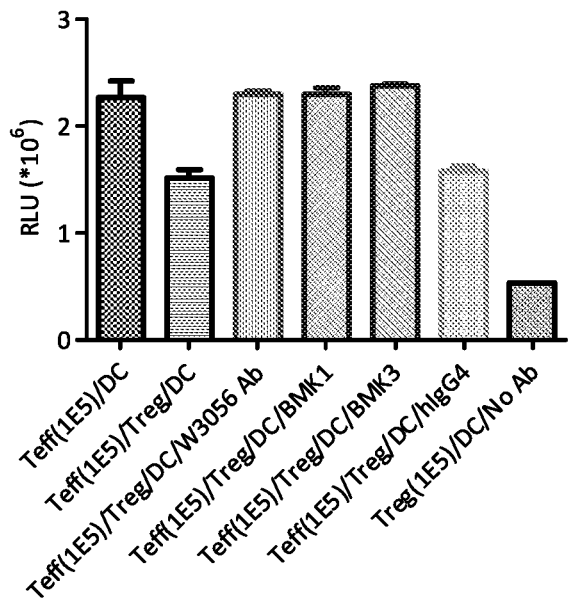

As shown in FIG. 12, the W3056 antibody W3056-AP17R1-2H2-Z1-R1-14A1-FC(IgG4.SP), can reverse human Treg induced T effector cell suppression, measured by IFN-γ production (FIG. 12A) and T cell proliferation (FIG. 12B)

vi). Antibody-Dependent Cell-Mediated Cytotoxicity (ADCC)

Figure 13:
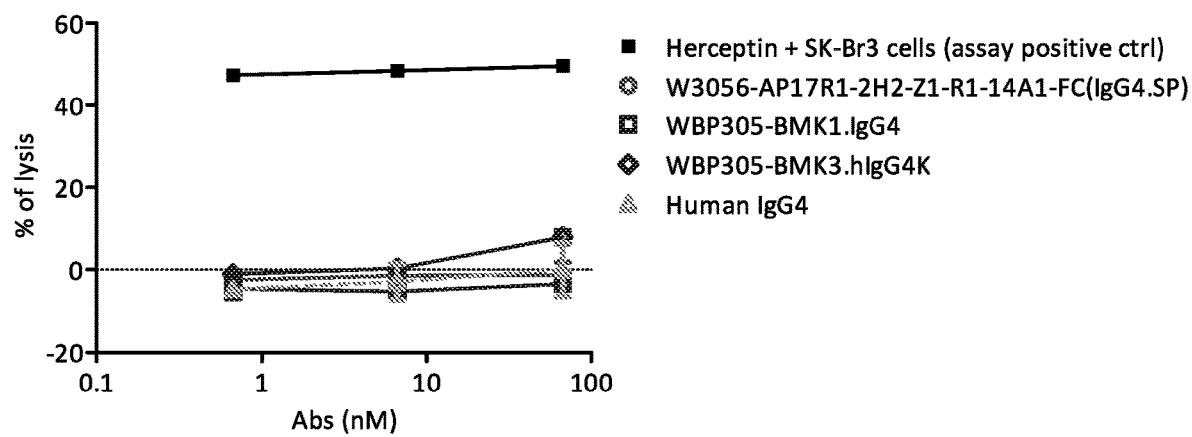
FIG. 13 shows the ADCC assays of the anti-PD-1 antibodies.

The human PD-1 transfected cell line WBP305-CHO-S.hPro1.C6 cells and various concentrations of testing antibodies were mixed in 96-well plate, and PBMCs were added at the effector/target ratio of 50:1. The plate was kept at 37° C. in a 5% CO$_2$ incubator for 4-6 hours. Target cell lysis was determined by LDH-based cytotoxicity detection kit. Herceptin induced ADCC effect on SK-Br-3 cells was used as positive control. The results indicated that W3056 antibody W3056-AP17R1-2H2-Z1-R1-14A1-FC (IgG4.SP) did not induce ADCC effects on human PD-1 transfected cells, as shown in FIG. 13.

16. Affinity to Human, Mouse and Cyno PD-1 by Surface Plasmon Resonance (SPR)

Antibody binding affinity to human, mouse and cynomolgus PD-1 was detected using Biacore 8K. W3056-AP17R1-2H2-Z1-R1-14A1-FC (IgG4.SP) was captured on an anti-human Fc IgG antibody immobilized CM5 sensor chip (GE). Human, mouse and cynomolgus PD-1 at different concentrations were injected over the sensor chip at a flow rate of 30 uL/min for an association phase of 120 s, followed by 150 s dissociation. The chip was then regenerated by 10 mM Glycine pH 1.5 after each binding cycle.

The sensorgrams of blank surface and buffer channel were subtracted from the test sensorgrams. The experimental data was fitted by 1:1 model using Langmiur analysis. Molecular weight of 40, 45 and 40 kDa was used to calculate the molar concentration of analyte human, mouse and cynomolgus PD-1 respectively. The SPR results show that the affinities of W3056-AP17R1-2H2-Z1-R1-14A1-FC(IgG4.SP) to human, cyno and mouse PD-1 were 3.45E-09M, 8.53E-09M and 2.87E-08M, respectively (Table 11).

TABLE 11

| | Binding kinetic affinity tested by surface plasmon resonance (SPR) | | | | | | | | |
|---|---|---|---|---|---|---|---|---|---|
| | Binding to human PD-1 | | | Binding to cyno PD-1 | | | Binding to mouse PD-1 | | |
| Ligand | ka (1/Ms) | kd (1/s) | KD (M) | ka (1/Ms) | kd (1/s) | KD (M) | ka (1/Ms) | kd (1/s) | KD (M) |
| W3056-AP17R1-2H2-Z1-R1-14A1-FC(IgG4.SP) | 2.48E+05 | 8.57E-04 | 3.45E-09 | 2.08E+05 | 1.77E-03 | 8.53E-09 | 1.47E+05 | 4.22E-03 | 2.87E-08 |
| WBP305-BMK1.IgG4 | 4.05E+05 | 1.16E-03 | 2.87E-09 | 3.01E+05 | 6.72E-04 | 2.23E-09 | No/weak binding | | |
| WBP305-BMK3.hIgG4K | 1.77E+05 | 6.63E-04 | 3.74E-09 | 1.84E+05 | 5.17E-02 | 2.81E-07 | | | |

7. Thermal Stability by DSF Assay

Figure 14:
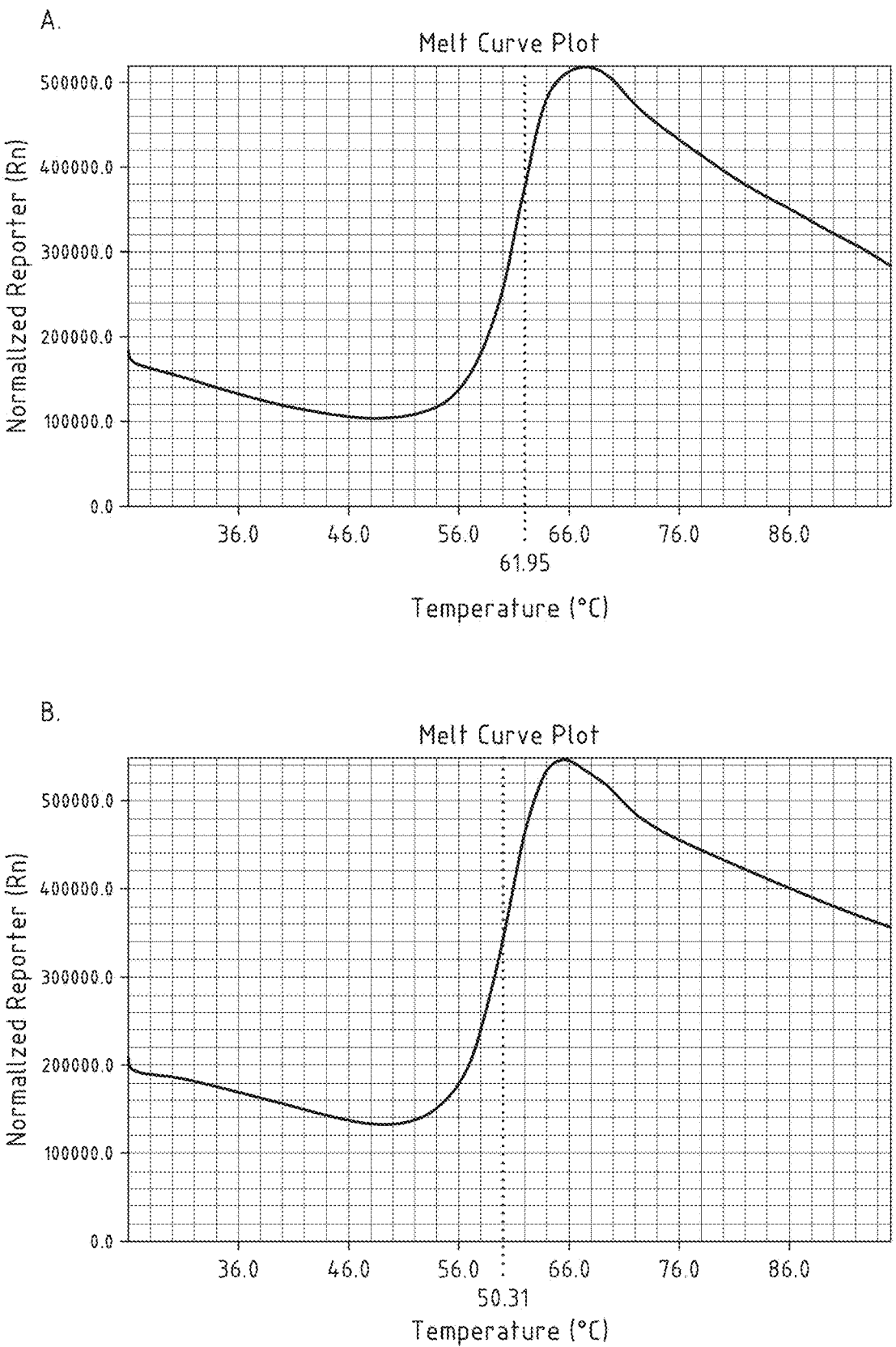
FIG. 14 shows the results of thermal stability test of W3056-AP17R1-2H2-Fc(IgG4.SP) (panel A) and W3056-

The DSF assay was performed using Real-Time Fluorescent Quantitative PCR (QuantStudio 7 Flex, Thermo Fisher Scientific). Briefly, 19 μL of antibody solution was mixed with 1 μL of 62.5× SYPRO Orange solution (Invitrogen) and added to a 96-well plate (Biosystems). The plate was heated from 26° C. to 95° C. at a rate of 2° C./min, and the resulting fluorescence data were collected. The negative derivatives of the fluorescence changes with respect to different temperatures were calculated, and the maximal value was defined as melting temperature Tm. If a protein has multiple unfolding transitions, the first two Tm were reported, named as Tm1 and Tm2. Tm1 is always interpreted as the formal melting temperature Tm to facilitate comparisons between different proteins. Data collection and Tm calculation were conducted automatically by its operation software. Once the plot of negative derivatives of different temperatures was reported by the software (QuantStudio Real-Time PCR PCR Software v1.3). The DST result is shown in table 12 and DSF profile is shown in FIG. 14. W3056 antibodies have normal DSF profiles and the Tm values are 60.3~62° C.

TABLE 12

Thermal stability result by DSF

| Protein Name | W3056-AP17R1-2H2-Fc(IgG4.SP) | W3056-AP17R1-2H2-Z1-R1-14A1-FC(IgG4.SP) |
|---|---|---|
| Isotype | hIgG4 | hIgG4 |
| pI | 6.4 | 6.4 |
| Buffer | PBS | PBS |
| Concentration (mg/ml) | 2.8 | 3.5 |
| Tm(° C.) | 62.0 | 60.3 |

8. Human Serum Stability Assay

Human serum was freshly isolated from a healthy donor by centrifugation. The antibody was 10-fold diluted in human serum. Five aliquots of the sample were incubated at 37° C. Sample at day 0, day 1, day 4, day 7 and day 14 were collected and frozen in liquid nitrogen, respectively.

The human PD-1 transfected cell line WBP305-CHO-S.hPro1.C6 cells ($1 \times 10^5$ cells/well) were incubated with various concentrations of serum treated W3056 anti-PD-1 antibodies (3-fold serially diluted from 129.9 nM to 0.0007 nM) at 4° C. for 1 hour. After washing with 1×PBS/1% BSA, the secondary antibody PE-labeled goat anti-human IgG was applied and incubated with cells at 4° C. for 1 hour. Human IgG4 isotype antibody was used as negative control. The cells were then washed and resuspended in 1×PBS/1% BSA. MFI of the cells was measured by a flow cytometer (BD) and analyzed by FlowJo.

The results shown in FIG. 15 indicate that W3056 antibody W3056-AP17R1-2H2-Z1-R1-14A1-FC(IgG4.SP) was stable in human serum for at least 14 days.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments that have been described in detail herein. Rather, reference should be made to the appended claims as indicative of the scope and content of the invention.

The invention claimed is:

1. A Programmed Death 1 (PD-1) binding VHH molecule, wherein the VHH molecule comprises a CDR1, a CDR2 and a CDR3, and wherein:
   the CDR1 comprises the amino acid sequence of SEQ ID NO: 13, the CDR2 comprises the amino acid sequence of SEQ ID NO: 14, and the CDR3 comprises the amino acid sequence of SEQ ID NO: 15.

2. The VHH molecule of claim 1, wherein the VHH molecule comprises
   (A) the amino acid sequence of SEQ ID NO: 42;
   (B) an amino acid sequence which is at least 85%, at least 90%, or at least 95% identical to SEQ ID NO: 42; or
   (C) an amino acid sequence with addition, deletion and/or substitution of 1, 2, 3, 4, 5, 6, 7, 8, 9 or 10 amino acids compared with SEQ ID NO: 42.

3. An isolated nucleic acid molecule comprising a nucleic acid sequence encoding the VHH molecule as defined in claim 1.

4. The isolated nucleic acid molecule of claim 3, comprising or consisting of the nucleic acid sequence of SEQ ID NO: 55.

5. An expression vector comprising the isolated nucleic acid molecule of claim 3.

6. A host cell comprising the expression vector of claim 5, wherein the host cell is a bacterial cell, a fungal cell or a mammalian cell.

7. A pharmaceutical composition comprising at least one VHH molecule as defined in claim 1 and a pharmaceutically acceptable carrier.

8. A method for preparing a PD-1 binding VHH molecule comprising the steps of:
   expressing the PD-1 binding VHH molecule as defined in claim 1 in a bacterial cell, fungal cell, or a mammalian cell; and
   isolating the PD-1 binding VHH molecule from the host cell.

9. A method for inhibiting or blocking the binding of PD-L1 or PD-L2 to PD-1 in a human subject, comprising:
   administering a therapeutically effective amount of the PD-1 binding VHH molecule as defined in claim 1 to the subject.

10. A method of treatment, comprising: administering a therapeutically effective amount of the PD-1 binding VHH molecule as defined in claim 1 to a human subject that has a tumor or cancer that expresses PD-L1, wherein the binding of PD-L1 to PD-1 in said human is inhibited.

11. A kit for treating or diagnosing proliferative disorders or cancers, comprising a container comprising the VHH molecule as defined in claim 1.

12. The VHH molecule of claim 1, wherein the VHH molecule is fused to a Fc domain of an immunoglobin, a fluorescent protein or a second VHH.

* * * * *